(12) United States Patent
Krauss et al.

(10) Patent No.: US 10,544,412 B2
(45) Date of Patent: Jan. 28, 2020

(54) DIRECTED EVOLUTION OF MULTIVALENT GLYCOPEPTIDES THAT TIGHTLY BIND TO TARGET PROTEINS

(71) Applicants: Brandeis University, Waltham, MA (US); The General Hospital Corporation, Boston, MA (US)

(72) Inventors: Isaac J. Krauss, Waltham, MA (US); Satoru Horiya, Waltham, MA (US); Yollete V. Guillen Schlippe, Boston, MA (US)

(73) Assignees: Brandeis University, Waltham, MA (US); The General Hospital Corporation, Boston, MA (US)

( * ) Notice: Subject to any disclaimer, the term of this patent is extended or adjusted under 35 U.S.C. 154(b) by 910 days.

(21) Appl. No.: 15/101,248

(22) PCT Filed: Dec. 2, 2014

(86) PCT No.: PCT/US2014/068186
§ 371 (c)(1),
(2) Date: Jun. 2, 2016

(87) PCT Pub. No.: WO2015/084861
PCT Pub. Date: Jun. 11, 2015

(65) Prior Publication Data
US 2016/0304858 A1    Oct. 20, 2016

Related U.S. Application Data

(60) Provisional application No. 61/910,710, filed on Dec. 2, 2013.

(51) Int. Cl.
| | |
|---|---|
| *C12N 15/10* | (2006.01) |
| *G01N 33/68* | (2006.01) |
| *C07K 19/00* | (2006.01) |
| *A61K 39/21* | (2006.01) |
| *C07K 16/10* | (2006.01) |
| *A61K 39/00* | (2006.01) |

(52) U.S. Cl.
CPC .......... *C12N 15/1058* (2013.01); *A61K 39/21* (2013.01); *C07K 16/1063* (2013.01); *C07K 19/00* (2013.01); *C12N 15/1062* (2013.01); *G01N 33/6845* (2013.01); *A61K 2039/575* (2013.01); *C07K 2317/76* (2013.01); *C07K 2317/92* (2013.01); *C07K 2319/91* (2013.01); *C12N 2740/16122* (2013.01); *C12N 2740/16134* (2013.01)

(58) Field of Classification Search
None
See application file for complete search history.

(56) References Cited

U.S. PATENT DOCUMENTS

| | | |
|---|---|---|
| 2004/0091955 A1 | 5/2004 | Forster et al. |
| 2013/0116417 A1 | 5/2013 | Krauss et al. |

FOREIGN PATENT DOCUMENTS

WO    2014/189768 A1    11/2014

OTHER PUBLICATIONS

International Search Report and Written Opinion for corresponding application No. PCT/US2014/068186, filed Dec. 2, 2014 (dated Mar. 5, 2015).
Ng et al., "Quantitative Synthesis of Genetically Encoded Glycopeptide Libraries Displayed on M13 Phage," ACS Chem. Biol. 7(9):1482-1487 (2012).
Usui et al., "A Designed Glycopeptide Array for Characterization of Sugar-Binding Proteins Toward a Glycopepide Chip Technology," Nanobiotechnol. 1(2):191-199 (2005).

*Primary Examiner* — Christopher M Gross
(74) *Attorney, Agent, or Firm* — Pepper Hamilton LLP

(57) ABSTRACT

The invention relates to a method for selecting a glycopolypeptide that binds to a target protein, the method including the steps of providing a pool of glycopolypeptides fused via puromycin linker to an encoding mRNA-cDNA duplex; combining the pool with a target protein to form a mixture; incubating the mixture for a period of time sufficient to allow any target protein to bind to one or more of the glycopolypeptides, thereby forming glycopolypeptide-target protein complexes; and isolating from the mixture the glycopolypeptide-target protein complexes, thereby identifying a plurality of selected glycopolypeptides.

20 Claims, 15 Drawing Sheets
Specification includes a Sequence Listing.

```
8E    mREWQRKmTQKEYTRKTCKPTRCWLDKSDRTSK
12G   mYKNIPSTTmNLYSKPmATVTTLKCKLNGNRIS
```

6E        mQTACPSPAFLmLSRSAHYFHAmHPTSAAPDIS
12G      mYKNIPSTTmNLYSKPmATVTTLKCKLNGNRIS

DIRECTED EVOLUTION OF MULTIVALENT GLYCOPEPTIDES THAT TIGHTLY BIND TO TARGET PROTEINS

This application is a national stage application under 35 U.S.C. § 371 of PCT Application No. PCT/US2014/068186, filed Dec. 2, 2014, which claims the benefit of U.S. Provisional Patent Application Ser. No. 61/910,710, filed Dec. 2, 2013, which is hereby incorporated by reference in its entirety.

This invention was made with government support from the National Institutes of Health under grant R01 AI090745. The U.S. government has certain rights in this invention.

FIELD OF THE INVENTION

The present invention relates to a method for in vitro selection of multivalent glycopeptides that mimic native glycosylated epitopes.

BACKGROUND OF THE INVENTION

Antibody 2G12, isolated from an HIV positive individual, binds and neutralizes a broad range of HIV strains (Trkola et al., *J. Virol.* 70:1100-1108 (1996) and Binley et al., *J. Virol.* 78:13232-13252 (2004)) and provides sterilizing immunity against SHIV challenge in macaque models of infection (Mascola et al., *Nat. Med.* 6:207-210 (2000); Hessell et al., *Nat. Med.* 15:951-954 (2009); and Hessel et al., *PLoS Pathog.* 5:e1000433 (2009)). 2G12 recognizes an epitope comprised of 2-4 high mannose ($Man_9GlcNAc_2$) glycans on the surface of HIV envelope protein gp120 (Scanlan et al., *J. Virol.* 76:7306-7321 (2002); Calarese et al., *Science* 300:2065-2071 (2003); and Calarese et al. *Proc. Natl. Acad. Sci. U.S.A.* 102:13372-13377 (2005)) and glycopeptides which precisely mimic this glycan clustering and presentation may be useful as vaccines to "re-elicit" 2G12-like antibodies in vivo (Scanlan et al., *Nature* 446:1038-1045 (2007)). Glycans clustered on carbohydrate scaffolds (Ni et al., *Bioconjugate Chem.* 17:493-500 (2006)), peptide scaffolds (Joyce et al., *Proc. Natl. Acad. Sci. U.S.A.* 105:15684-15689 (2008)), and protein scaffolds (Astronomo et al., *J. Virol.* 82:6359-6368 (2008)) as well as phage particles (Astronomo et al., *Chem. Biol.* 17:357-370 (2010)) and yeast (Luallen et al., *J. Virol.* 82:6447-6457 (2008); Luallen et al., *J. Virol.* 83:4861-4870 (2009); Agrawal-Gamse et al., *J. Virol.* 85:470-480 (2011); Ciobanu et al., *Chem. Commun.* 47:9321-9323 (2011); and Marradi et al., *J. Mol. Biol.* 410:798-810 (2011)) have been tested for this purpose, but with little success. In part, this may be due to the difficulty of designing structures in which the clustering of glycans faithfully mimics that of the 2G12 epitope on gp120. Indeed, most of these structures were recognized by 2G12 with orders of magnitude weaker affinity than was gp120, suggesting that they were not optimal mimics of the 2G12 epitope.

The directed evolution of glycopeptides has been of interest, given their relevance in both HIV and cancer vaccine design. Although many powerful methods are available for in vitro selection of peptides, comparatively little has yet been published on in vitro selection of glycopeptides. Recently phage display with chemically-modified phages enabled selection of peptide 5-mer sequences containing a single central mannose monosaccharide from ~$10^6$ sequences (Arai et al., *Bioorg. Med. Chem. Lett.* 23:4940-4943 (2013)). In an alternative approach, a single mannose was chemically attached to the N-terminal position of a 7-mer phage-displayed library of ~$10^8$ sequences, although selections with this library have not yet been reported (Ng et al., *ACS Chem. Biol.* 7:1482-1487 (2012)). Because carbohydrate epitopes of various pathogen (e.g., HIV) and cancer cells may contain multiple glycans (see Scanlan et al., *J. Virol.* 76:7306-7321 (2002); Calarese et al., *Science* 300:2065-2071 (2003); and Calarese et al. *Proc. Natl. Acad. Sci. U.S.A.* 102:13372-13377 (2005)), it is desirable that a selection method allow access to multivalent glycopeptides containing one or more glycans at variable positions, supported by a peptide framework.

More importantly, it is desirable for selected glycopeptides to exhibit high affinity binding to known carbohydrate-binding monoclonal antibodies or other targets used during selection. Such carbohydrate-binding monoclonal antibodies include antibodies known to neutralize pathogens and antibodies known to afford protection (i.e., cytotoxicity) against cancer cells.

The present invention is directed to overcoming these and other deficiencies in the art.

SUMMARY OF THE INVENTION

The invention relates to a method for selecting a glycopolypeptide that binds to a target protein. The method includes providing a pool of glycopolypeptides fused via puromycin linker to an encoding mRNA-cDNA duplex; combining the pool with a target protein to form a mixture; incubating the mixture for a period of time sufficient to allow the target protein to bind to one or more of the glycopolypeptides, thereby forming glycopolypeptide-target protein complexes; and isolating from the mixture the glycopolypeptide-target protein complexes, thereby identifying a plurality of selected glycopolypeptides.

As demonstrated by the accompanying Examples, the selection method disclosed herein allows for the generation of a pool of multivalent glycopeptides containing several glycans at variable positions, supported by a significant peptide framework. This selection method includes Click chemistry glycosylation of mRNA-displayed peptide libraries of ~$10^{13}$ sequences. The usefulness of this selection method is demonstrated for HIV antigen design, whereby multiple glycopolypeptides containing 3-5 high-mannose nonasaccharides were generated and these glycopolypeptides tightly recognize the broadly neutralizing HIV antibody 2G12. These glycopolypeptides bound to 2G12 with an affinity substantially the same as the affinity between 2G12 and HIV-1 gp120. Multiple glycopolypeptides exhibited $K_D$'s below 5 nM, with the best binding glycopolypeptide having a $K_D$ as low as 500 pM. As a result, these glycopolypeptides adequately mimic the native gp120 epitope, and should therefore be useful as a vaccine to induce a neutralizing immune response against HIV-1.

*Chem. Soc.* 126:12752-12753 (2004), which are hereby incorporated by reference in their entirety) using PURE system cell-free translation (Shimizu et al., *Nat Biotech* 19:751-755 (2001); Josephson et al., *J. Am. Chem. Soc.* 127:11727-11735 (2005); Shimizu et al., *Methods* 36:299-304 (2005); Hartman et al., *PLoS ONE* 2:e972 (2007); and Guillen et al., *J. Am. Chem. Soc.* 134:10469-10477 (2012), which are hereby incorporated by reference in their entirety).

Figures 2A, 2B, 2C, 2D:
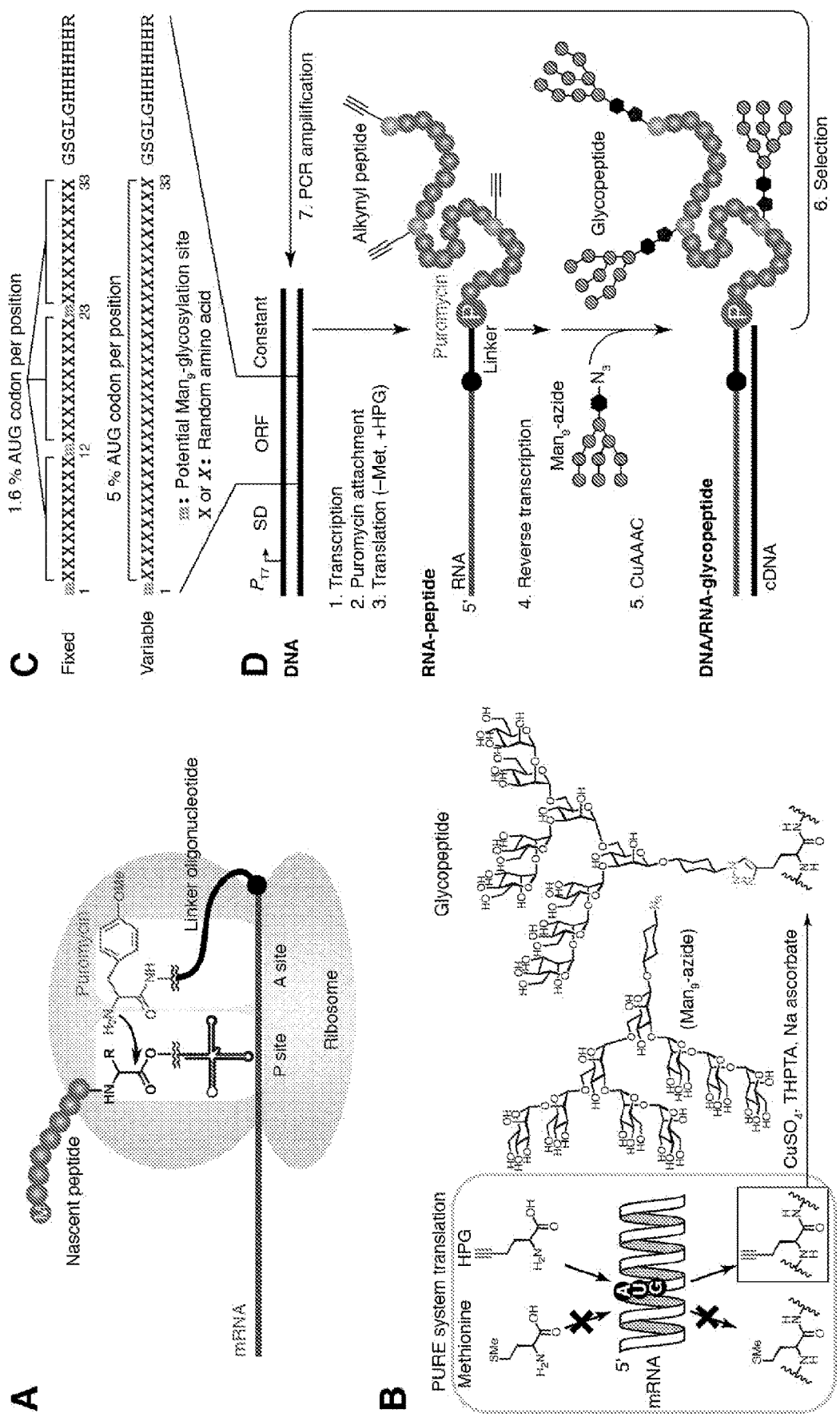

FIGS. 2A-D illustrate the in vitro selection of glycopeptides. FIG. 2A is a schematic illustration of the covalent linkage of nascent peptide to its mRNA, mediated by attachment to mRNA-linked puromycin inside the ribosome. FIG. 2B illustrates the use of PURE system to incorporate alkynes via the AUG codon and CuAAAC "click" chemistry glycosylation with the synthetic Man$_9$-azide. FIG. 2C illustrates the peptide libraries used in this study. The "fixed" library contains 3 constant glycosylation sites, whereas the "variable" library contains only one constant glycosylation site, at position 1. The random regions of both libraries are followed by a flexible linker and a His$_6$ tag. Puromycin attached to mRNA is covalently linked to C-terminal arginine residues in translation (Josephson et al., *J. Am. Chem. Soc.* 127:11727-11735 (2005), which is hereby incorporated by reference in its entirety). FIG. 2D illustrates the scheme for selection of 2G12-binding glycopeptides. The library DNA is comprised of T7 promotor ($P_{T7}$), s-enhancer followed by Shine-Dalgarno sequence (SD), the open reading frame (ORF) of the peptide and the constant region including the sequence for annealing and photo-crosslinking the mRNA to a puromycin-containing oligonucleotide.

Figures 3A, 3B:
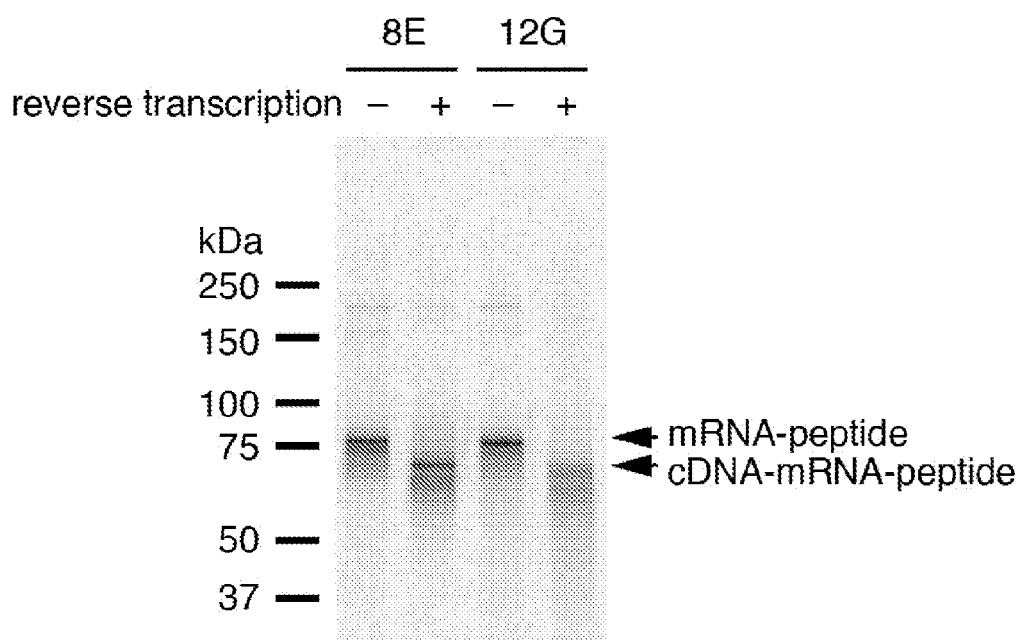
Figure 3C:
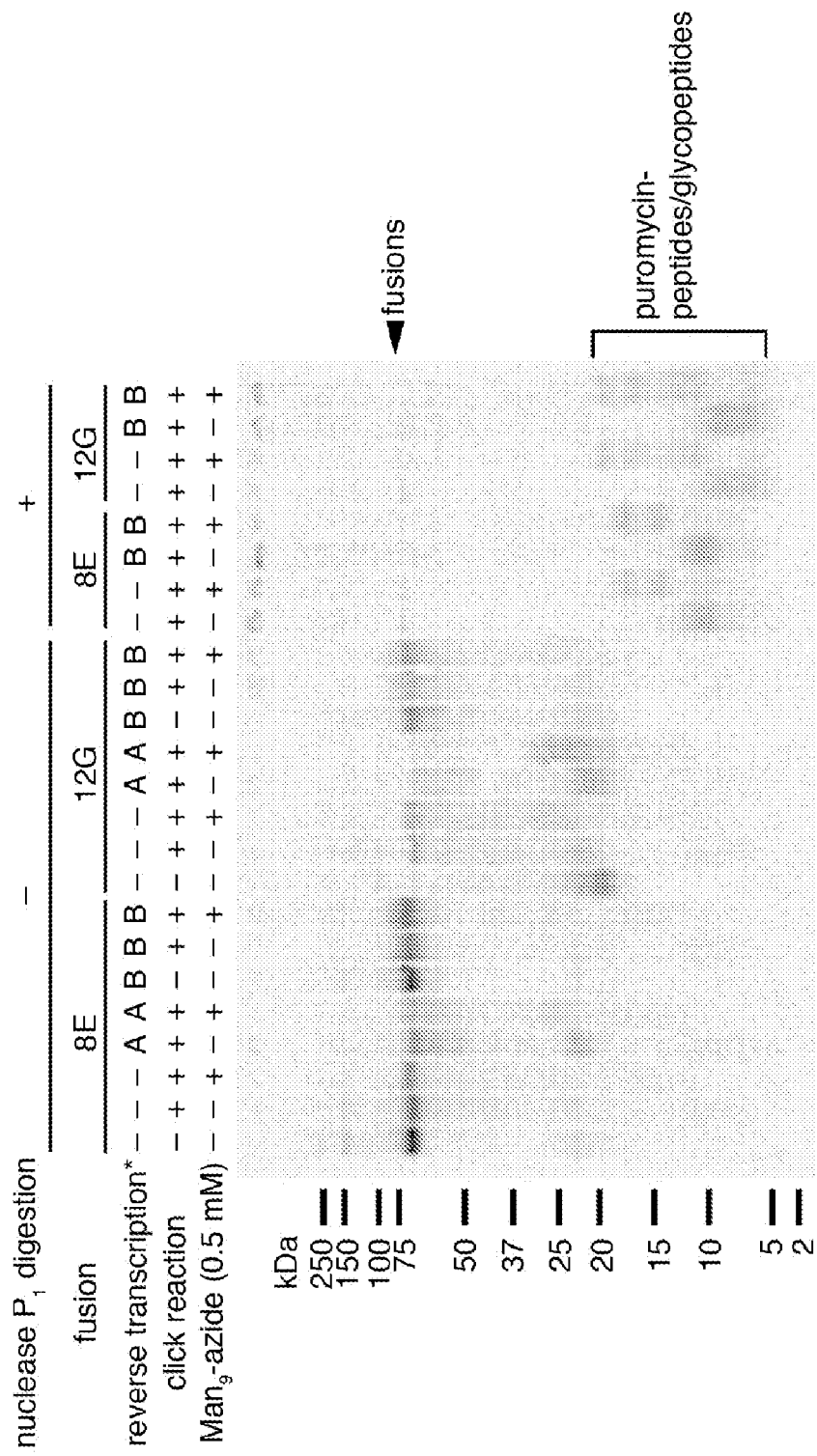

FIG. 3A-C illustrates the examination of the integrity of "click" glycosylated mRNA-peptide fusions before or after reverse transcription. FIG. 3A is an alignment of the peptide sequences for clones 8E and 12G (SEQ ID NOS: 61, 46). The sequences were obtained by cloning non-selected library DNA. FIG. 3B is an SDS-PAGE analysis of the reverse transcribed mRNA-peptide fusions labeled with $^{35}$S-cysteine using a 7.5% precast gel (Bio-Rad). In this condition, cDNA-mRNA-peptide fusions migrate faster than mRNA-peptide fusions. FIG. 3C is a SDS-PAGE analysis of fusion integrity. mRNA-peptide fusions were reverse transcribed after (A) or before (B) click reaction. The click reaction was done using a slightly different condition described in the Examples, in which 30-40 nM fusions shown in FIG. 3B were incubated with 100 mM HEPES-KOH (pH 7.6), 0.02% Triton X-100 (v/v), 1 mM CuSO$_4$, 2 mM THPTA, 5 mM aminoguanidine hemisulfate and 5 mM sodium ascorbate in the presence (+) or absence (−) of 0.5 mM Man$_9$-azide, which is a lower concentration compared to the regular condition described in the Examples, in argon-filled microtube at room temperature for 3 hours. The fusions without click reaction (−) were incubated with 100 mM HEPES-KOH (pH 7.6), 0.09% Triton X-100 (v/v) at room temperature in argon-filled microtubes for 3 hours as well. The fusions with or without nuclease P$_1$ digestion were separated by 10% Criterion XT Bis-Tris precast gel (Bio-Rad) with XT MES Running Buffer (Bio-Rad). The gels were analyzed by autoradiography.

Figure 4A:
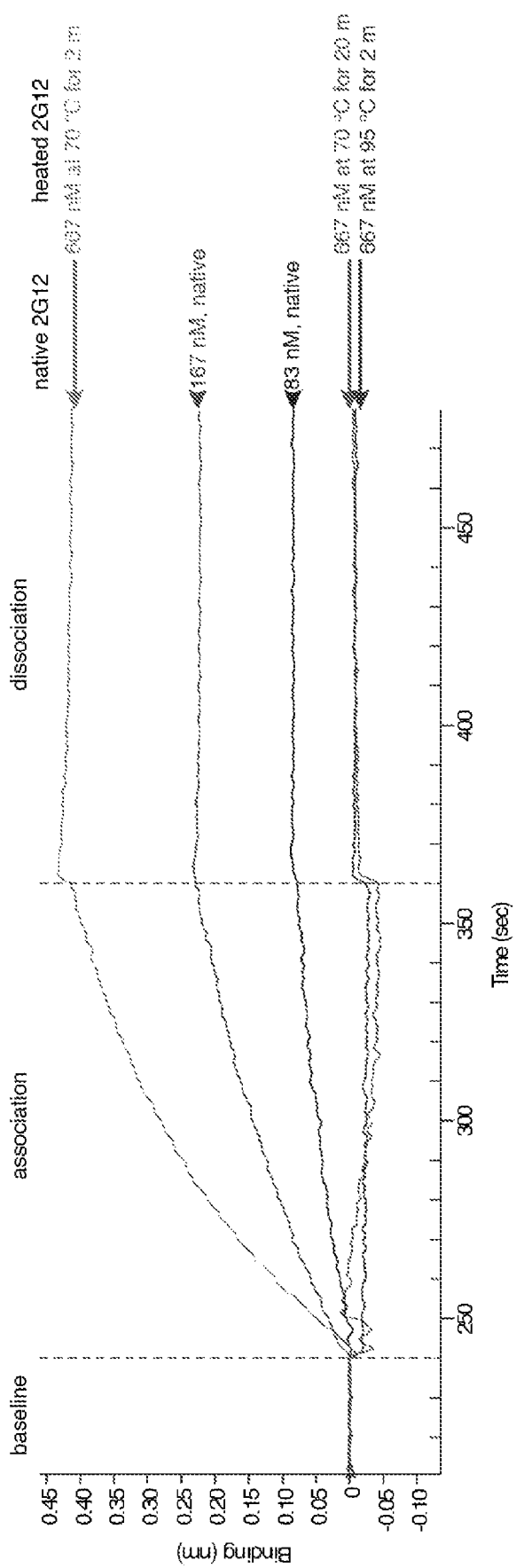
Figure 4B:
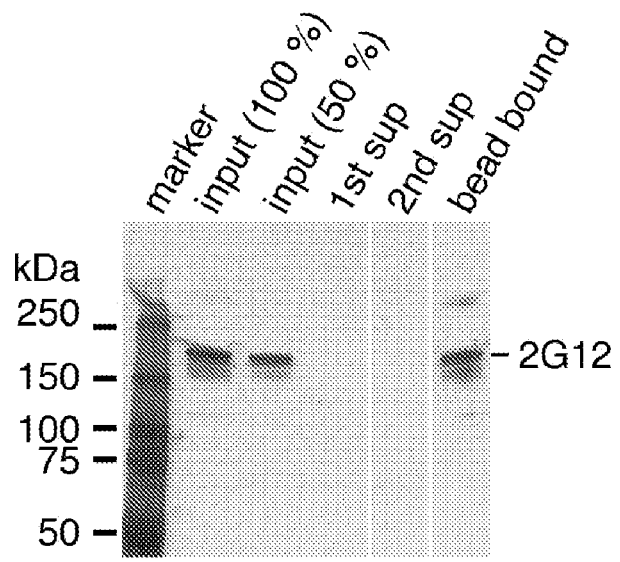
Figure 4C:
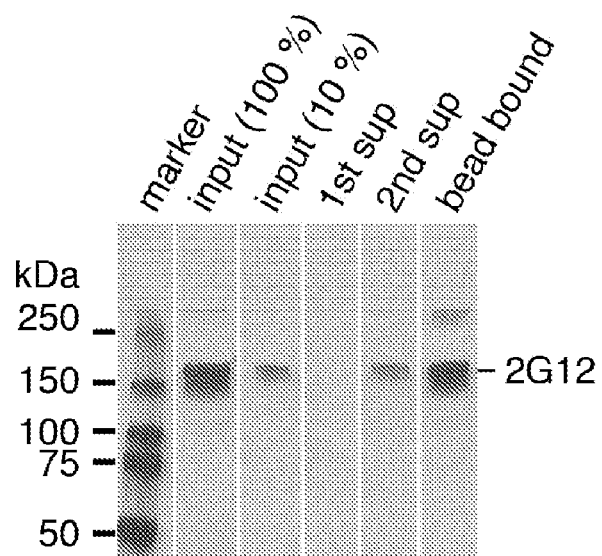
Figure 4D:
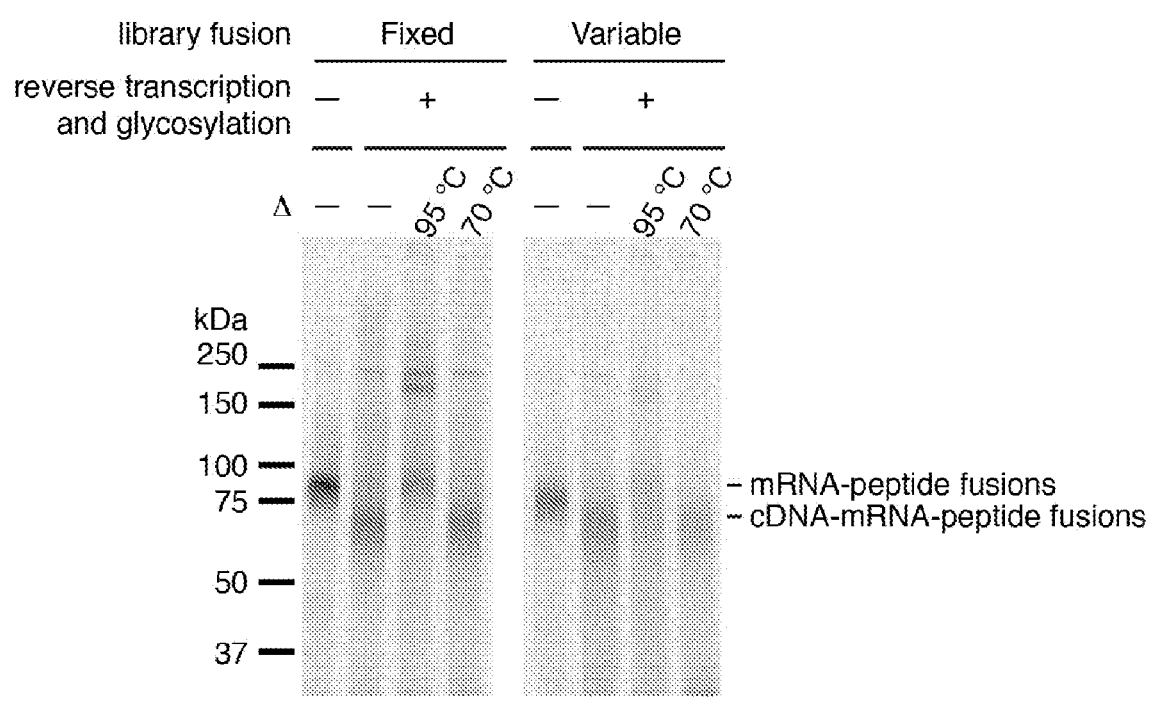

FIGS. 4A-D illustrate the thermostability of 2G12 and cDNA-mRNA duplex of the library fusions. FIG. 4A is an analysis of the interaction between 2G12 and gp120 using BLitz with Dip and Read Ni-NTA Biosensors (ForteBio). 25 µg/ml His$_6$-tagged gp120 (HIV-1 JRFL) (Immune Technology) was loaded on equilibrated Ni-NTA sensors for 3 min and then the sensors were equilibrated with selection buffer for 30 s. The 120-loaded sensors were used to associate with the native 2G12 or the 2G12 heated at 70° C. or 95° C., chilled on ice for 5 min and incubated at room temperature in selection buffer before loading. The time of the 2G12 association and dissociation steps in selection buffer were 2 min. FIG. 4B is a silver stained SDS-PAGE gel in which the 1$^{st}$ supernatant, 2$^{nd}$ supernatant, and bead bound fractions were analyzed. 100 nM 2G12 was incubated with 6 mg/ml protein G magnetic beads in selection buffer for 1 hr and the supernatant was removed (1st sup). The beads were resuspended in selection buffer and heated at 70° C. for 30 min, chilled on ice for 5 min, and incubated at room temperature for 10 min. Then, the supernatant (2nd sup) was removed and the 2G12 bound to the beads were eluted out by boil in Laemmli sample buffer (bead bound). The supernatants and bead bound fraction were analyzed with the controls of amounts of input to the beads using 4-20% SDS-PAGE without addition of reducing agent. The gel was silver-stained. FIG. 4C is the same experiment as shown in FIG. 4B using 12 mg/ml protein A magnetic beads except that the incubation time at 70° C. was 20 min. FIG. 4D is an SDS-PAGE gel analyzed by autoradiography. The $^{35}$S-cysteine labeled library fusions (50 fmol) for selection round 1 were heated at 95° C. for 2 min or 70° C. for 20 min and chilled on ice before being applied to 7.5% SDS-PAGE.

Figures 5A, 5B:
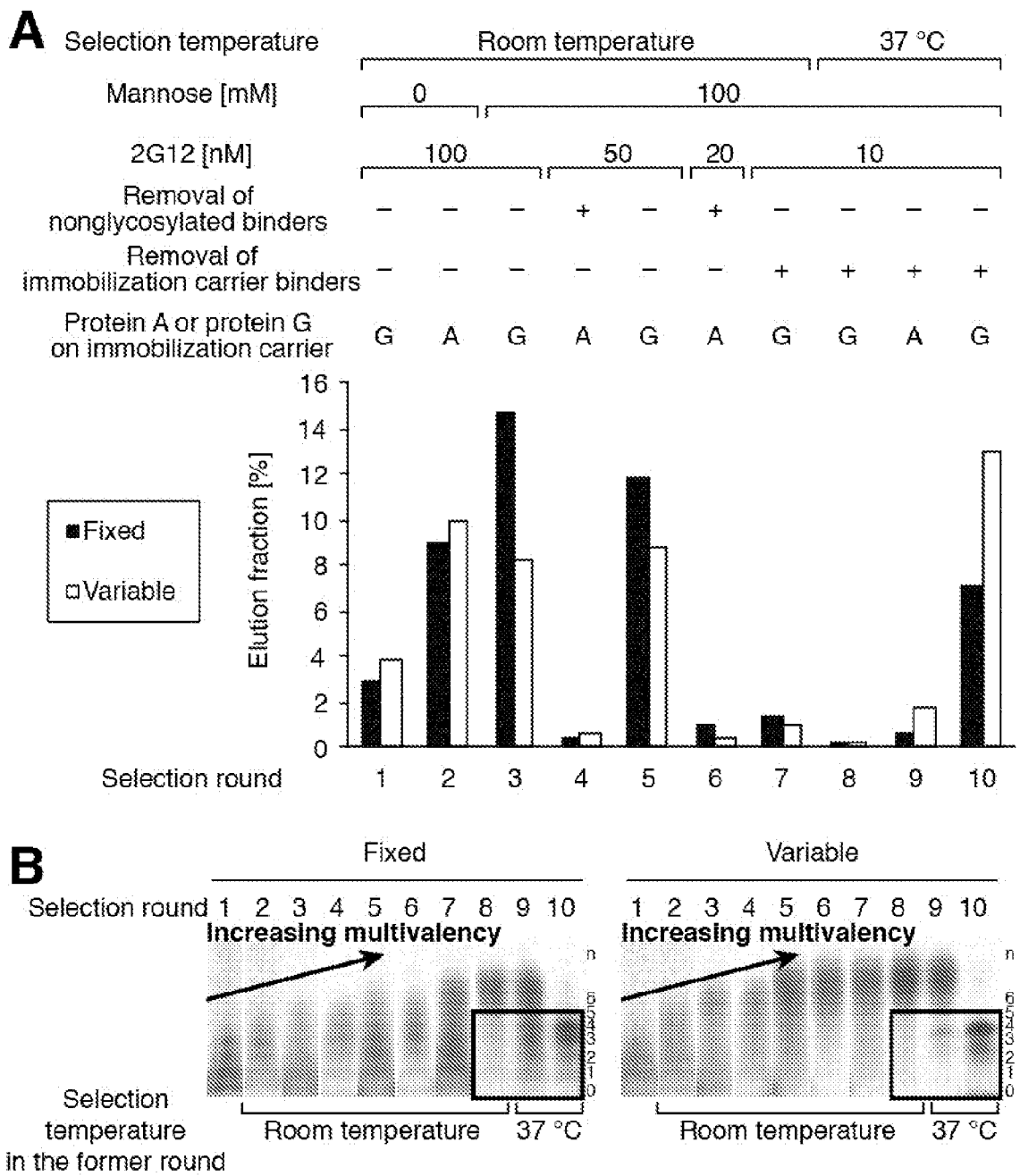

FIGS. 5A-B illustrate the experimental results of an in vitro selection of glycopeptides which bind to HIV broadly neutralizing antibody 2G12. FIG. 5A is a bar graph illustrating the selection conditions and percentage of radioactivity (counts per minute) in eluted fractions. Concentrations of the 2G12 listed for the selection are prior to addition of protein G or protein A magnetic beads. FIG. 5B is an SDS-PAGE gel illustrating the profiling of the distribution of the putative number of glycans in library peptides before selection ("n" on the right on the gel). The boxes indicate enrichment of low-valent glycopeptides in 37° C. selection rounds.

Figure 6A:
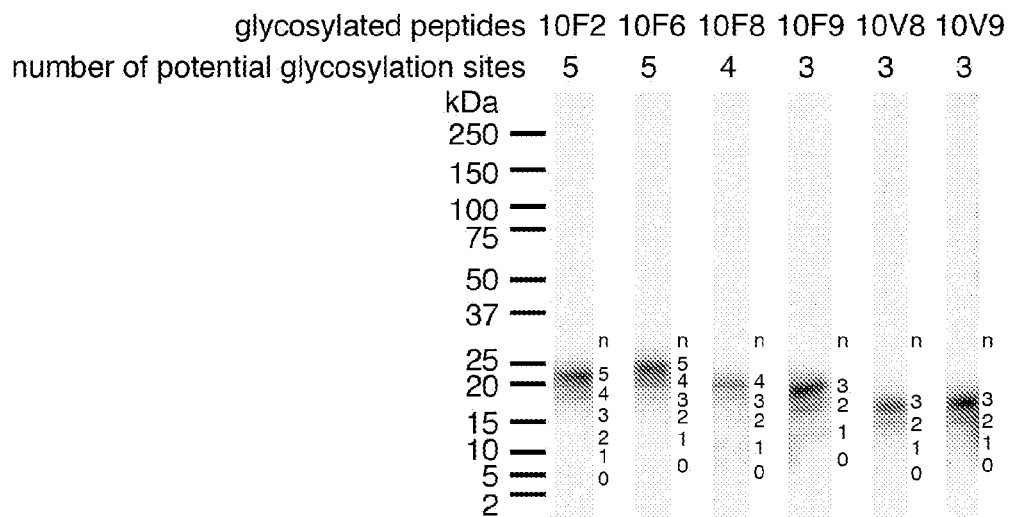
Figure 6B:
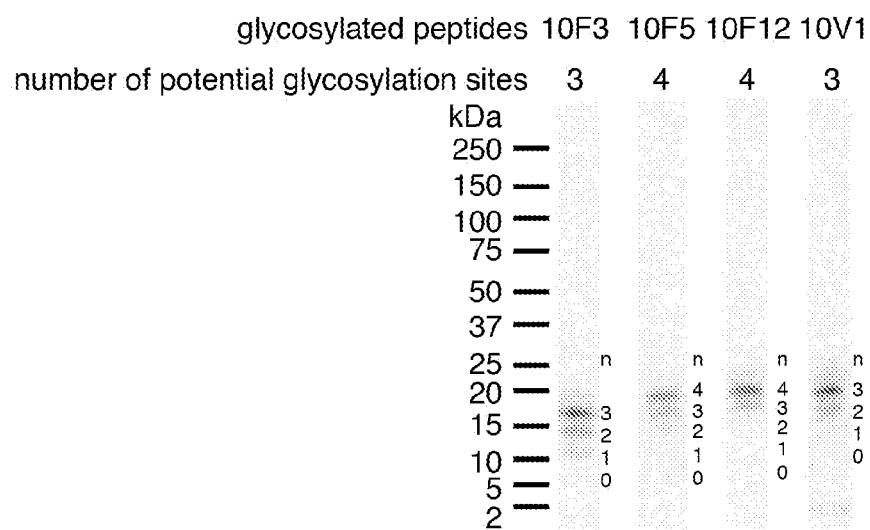

FIGS. 6A-B are SDS-PAGE analyses of the glycosylated peptides selected in round 10. The numbers "n" on the left of the gel image indicate the putative number of glycans the peptides. In FIG. 6A the peptides were labeled with $^3$H-histidine and the bands were visualized by fluorography. In FIG. 6B the peptides were labeled with $^{35}$S-cysteine and the bands were visualized by autoradiography.

Figure 7:
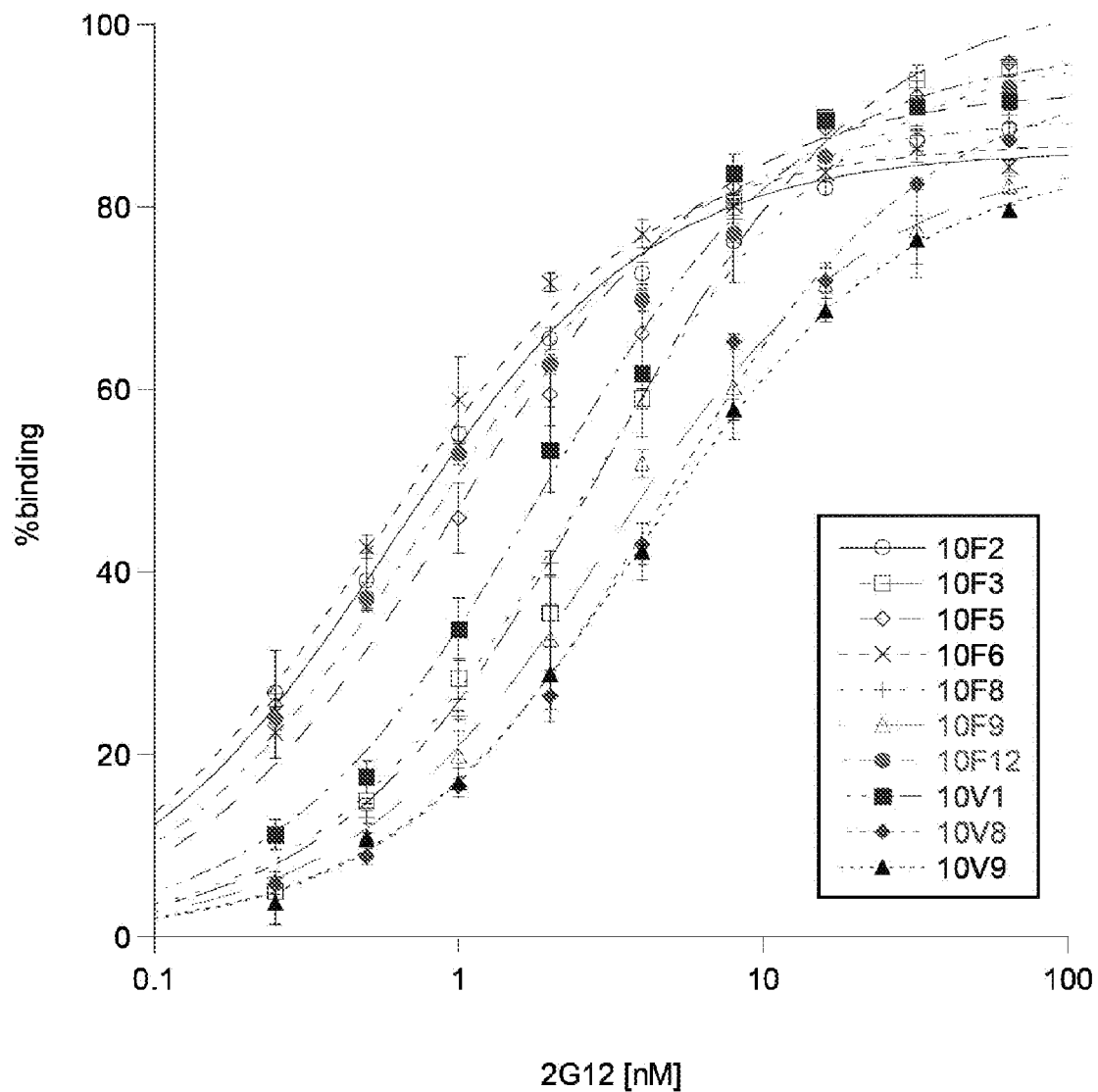

FIG. 7 illustrates the binding curves of the interaction between 2G12 and selected glycopeptides. The error bars represent standard error.

Figures 8A, 8B:
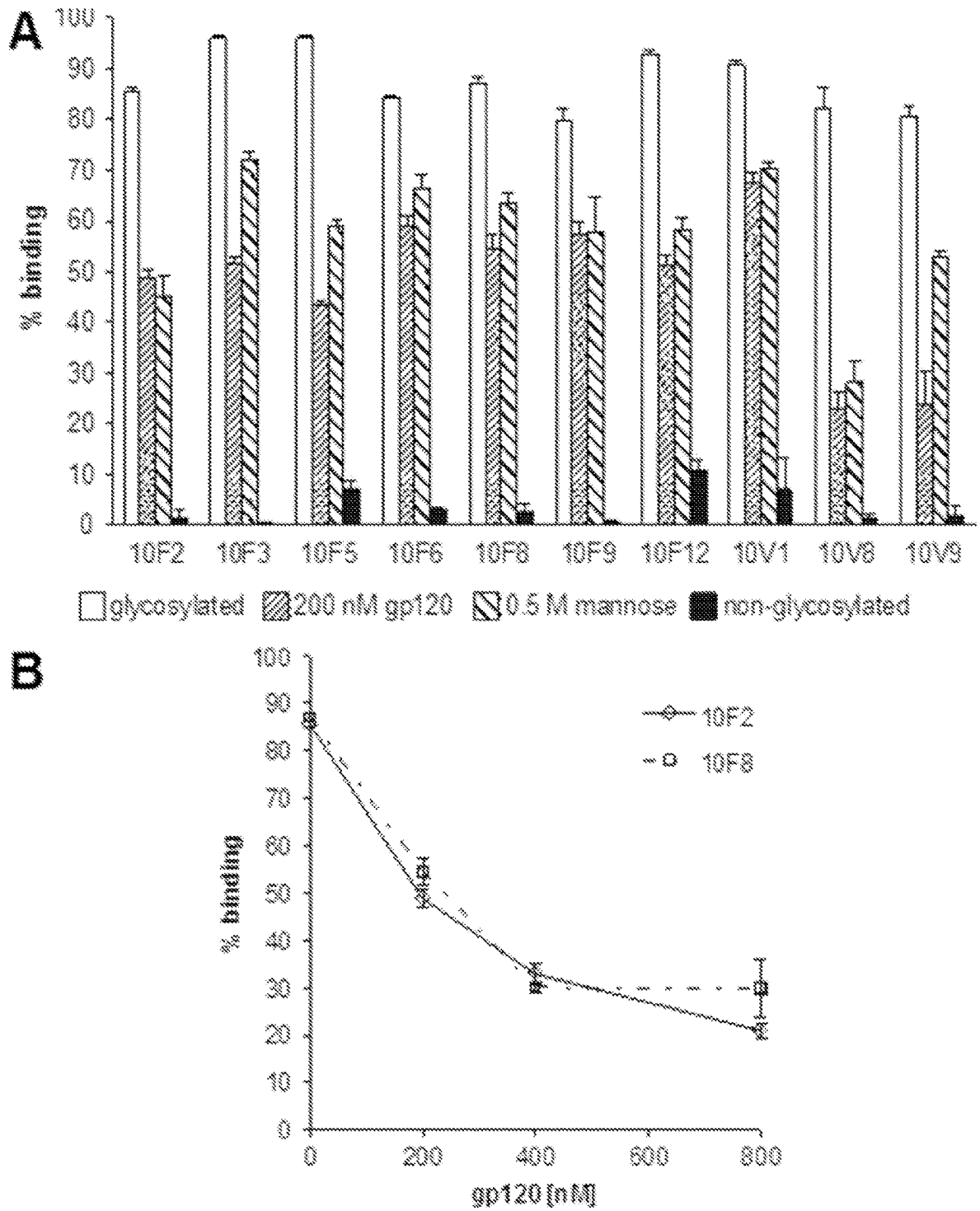

FIGS. 8A-B illustrate the importance of glycans in binding of selected glycopeptides to 2G12 and competition with gp120. FIG. 8A is a bar graph showing the competition of glycopeptide binding to 2G12 with gp120 and mannose and glycosylation-dependent binding. FIG. 8B is a line graph showing the competition of glycopeptide binding to 2G12 with varied concentrations of gp120.

Figures 9A, 9B:
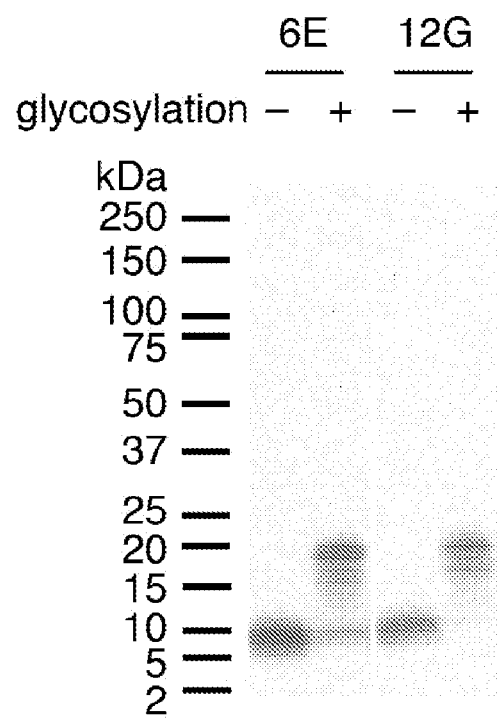
Figure 9C:
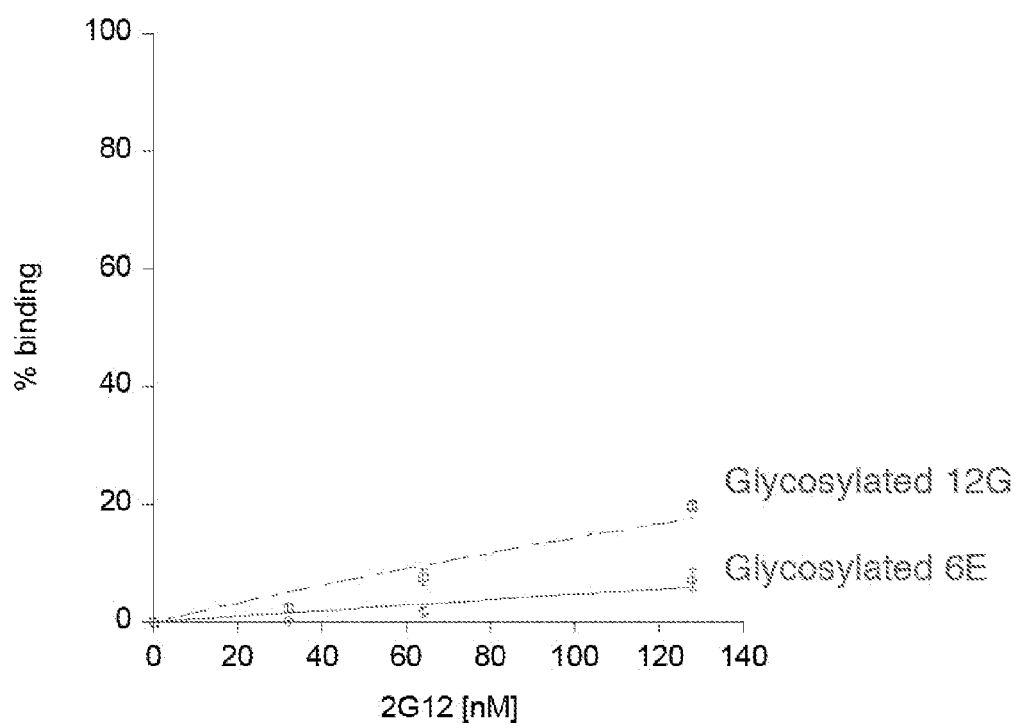

FIGS. 9A-C illustrate a binding study of individual glycopeptides obtained from the starting libraries before selection. FIG. 9A is an alignment of the peptide sequences for clones 6E and 12G (SEQ ID NOS: 45, 46). The sequences were obtained by cloning non-selected library DNA. Both peptides were followed by a flexible linker, a His6-tag and a FLAG-tag (GSGSLGHHHHHHRDYKDDDDK, SEQ ID NO: 1) for purification and radiolabeling purposes. FIG. 9B is an SDS-PAGE analysis of the click reaction of the non-selected peptides. Both peptides were transcribed and translated from PCR-amplified DNA in Pure System that contains 0.02 mg/mL T7 RNA polymerase and additional 1 mM each NTP. The peptides were labeled with 3H-histidine and the bands were visualized by fluorography. FIG. 9C is a graph of the binding curves for clones 6E and 12G. Data were obtained as described in Materials and Methods except that the 2G12 concentration was 0, 32, 64 or 128 nM and the amount of protein G magnetic beads was doubled to accommodate the high 2G12 concentrations used.

Figure 10A:
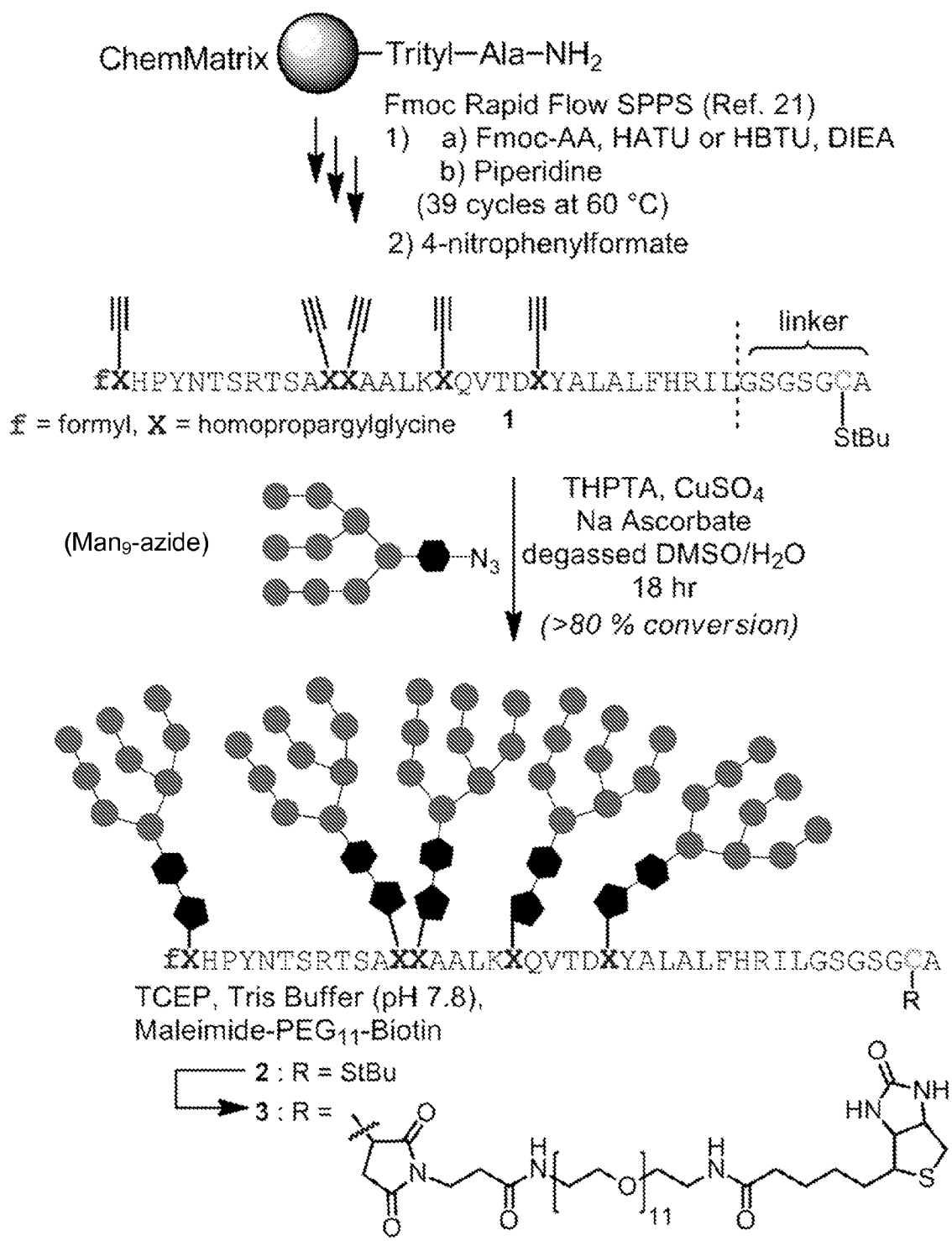
Figure 10B:
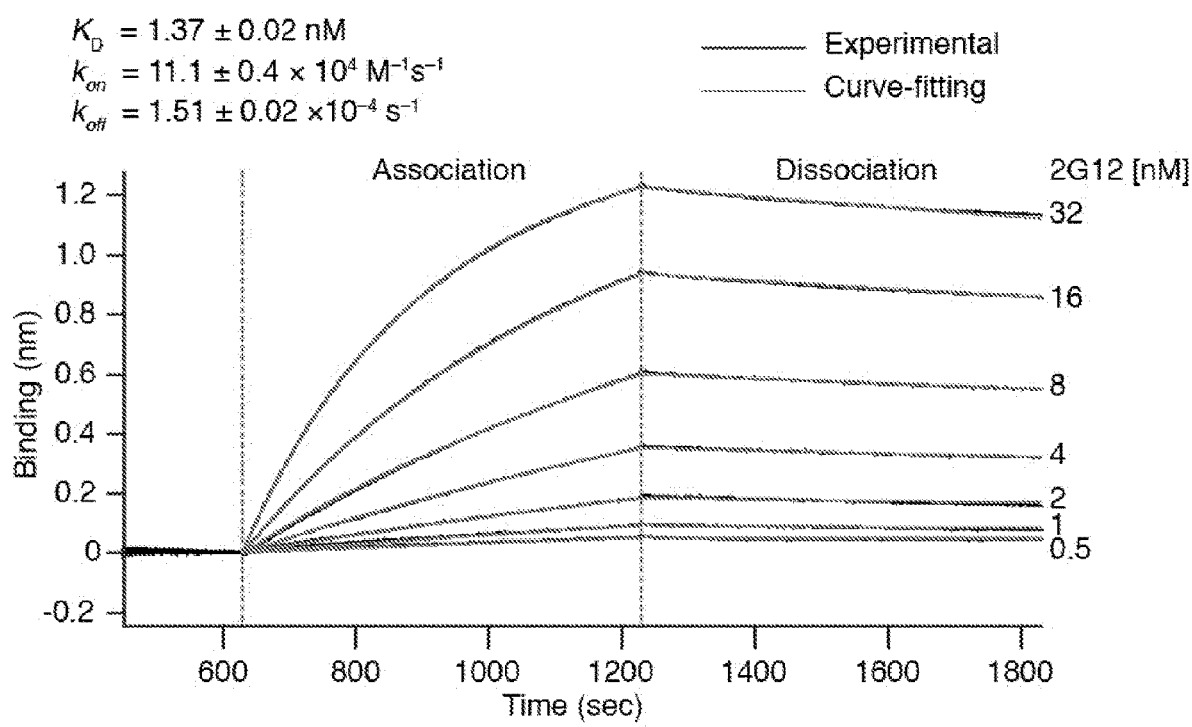

FIGS. 10A-B illustrate results of a BioLayer Interferometry ("BLI") assay. FIG. 10A is a schematic representation of the preparation of synthetic 10F2 glycopeptide and attachment of biotin for immobilization to streptavidin surface. FIG. 10B is a graph showing the results of a BLI measurement of 2G12 interacting with surface-immobilized synthetic 10F2 glycopeptide. $K_{on}$ and $k_{off}$ errors are standard errors of the curve fit, and the $K_D$ error is propagated from those values.

DETAILED DESCRIPTION OF THE INVENTION

The present invention relates to a method for in vitro selection of glycopeptides, which involves combining mRNA display with the incorporation of unnatural amino acids and "click" chemistry. Using this in vitro selection in combination with directed evolution of glycopeptides, it is possible to develop binding partners with any of a variety of target proteins, including epitope mimics that are bound tightly and specifically by carbohydrate-specific monoclonal antibodies.

Accordingly, the method for selecting a glycopolypeptide that binds to a target protein includes providing a pool of glycopolypeptides fused via puromycin linker to an encoding mRNA-cDNA duplex; combining the pool with a target protein to form a mixture; incubating the mixture for a period of time sufficient to allow any target protein to bind to one or more of the glycopolypeptides, thereby forming glycopolypeptide-target protein complexes; and isolating from the mixture the glycopolypeptide-target protein complexes, thereby identifying a plurality of selected glycopolypeptides. Multiple rounds of selection and regenerating mRNA-linked glycopolypeptide pools can be performed in the manner illustrated in FIG. 1.

Figure 1:
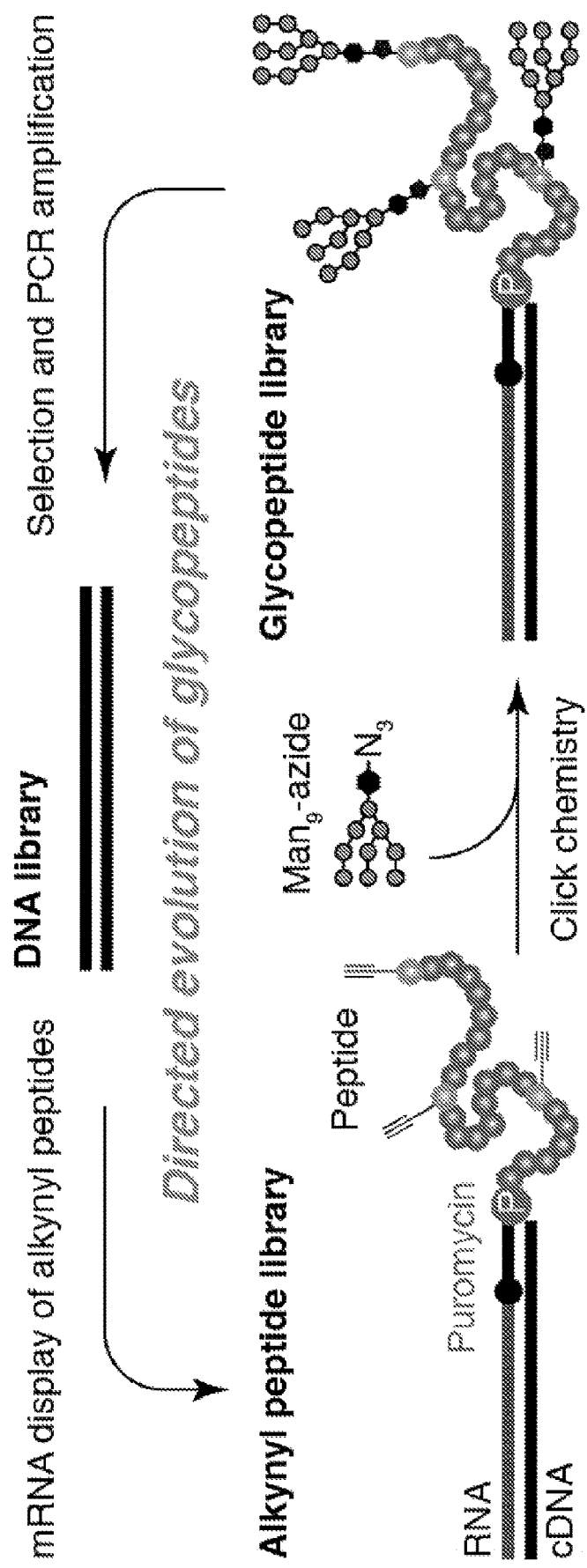
FIG. 1 illustrates how glycopeptide selection can be achieved by the combination of chemical synthesis, "click: chemistry (CuAAAC, or Copper Assisted Azide Alkyne Cycloaddition) (Kolb et al., *Angew. Chem. Int. Ed.* 40:2004-2021 (2001) and Rostovtsev et al., *Angew. Chem. Int. Ed.* 41:2596-2599 (2002), which are hereby incorporated by reference in their entirety), mRNA display selection (Roberts et al., *Proc. Natl. Acad. Sci. U.S.A.* 94:12297-12302 (1997), which is hereby incorporated by reference in its entirety) and codon reassignment (van Hest et al., *J. Am. Chem. Soc.* 122:1282-1288 (2000) and Tan et al., *J. Am.*

FIG. 1 illustrates how glycopeptide selection can be achieved by the combination of chemical synthesis, "click" chemistry (CuAAAC, or Copper Assisted Azide Alkyne Cycloaddition) (Kolb et al., *Angew. Chem. Int. Ed.* 40:2004-2021 (2001) and Rostovtsev et al., *Angew. Chem. Int. Ed.* 41:2596-2599 (2002), which are hereby incorporated by reference in their entirety), mRNA display selection (Roberts et al., *Proc. Natl. Acad. Sci. U.S.A.* 94:12297-12302 (1997), which is hereby incorporated by reference in its entirety), and codon reassignment (van Hest et al., *J. Am. Chem. Soc.* 122:1282-1288 (2000) and Tan et al., *J. Am. Chem. Soc.* 126:12752-12753 (2004), which are hereby incorporated by reference in their entirety) using PURE system cell-free translation (Shimizu et al., *Nat Biotech* 19:751-755 (2001); Josephson et al., *J. Am. Chem. Soc.* 127:11727-11735 (2005); Shimizu et al., *Methods* 36:299-304 (2005); Hartman et al., *PLoS ONE* 2, e972 (2007); and Guillen et al., *J. Am. Chem. Soc.* 134:10469-10477 (2012), which are hereby incorporated by reference in their entirety).

The provided pool of glycopolypeptides fused via puromycin linker to an encoding mRNA-cDNA duplex is preferably large enough to afford sufficient diversity so as to allow for selection of multiple, diverse glycopolypeptides that exhibit target protein binding capability. By way of example, the provided pool comprises about $10^{10}$ or greater, about $10^{11}$ or greater, about $10^{12}$ or greater, or about $10^{13}$ or greater glycopolypeptides fused via puromycin linker to an encoding mRNA-cDNA duplex.

Creation of the first pool is carried out by first generating a library of DNA duplexes of sufficient length to afford a glycopeptide pool of the desired complexity. Each DNA duplex includes a promoter sequence to allow for transcription, optionally an enhancer element sequence, a sequence containing a ribosomal binding site that affords in vitro translation of mRNA transcripts, an open reading frame region that affords sequence variety to generate glycopolypeptide diversity, and a downstream sequence that encodes, e.g., a His tag followed by a constant region that serves as the linker for puromycin. Any suitable promoter and enhancer sequences suitable for in vitro transcription can be used, and any suitable ribosomal binding sequence can be used. Sequence variation can be introduced using random diversity at each site or semi-random diversity at each site.

As shown in FIG. 1 and FIGS. 2A-D, the generation of pools of mRNA-supported glycopolypeptides and selection of individual pool members against target proteins is illustrated. The DNA duplexes are used as templates for generating mRNA templates. This can be achieved using any suitable in vitro transcription protocol. Thereafter, a puromycin linker is attached to the 3' region of the mRNA strand. Briefly, purified transcripts can be photo-crosslinked with puromycin-containing oligonucleotide. Photo-crosslinking is achieved using, e.g., 365 nm UV irradiation as previously described (Kurz et al., *Nucleic Acids Res.* 28:e83 (2000) and Seelig, B. *Nat. Protocols* 6:540-552 (2011), which are hereby incorporated by reference in their entirety).

Use of puromycin at the 3' region of the mRNA transcript allows for mRNA-display of the translated polypeptide based on the physical linkage of the polypeptide to the mRNA that encoded it. Puromycin inhibits translation by mimicking the substrate of the ribosome—the 3' end of an aminoacyl-tRNA. As ribosomes complete the translation of individual mRNAs to the corresponding peptides they encounter the 3' puromycin. Because puromycin is chemically similar to the 3' end of aminoacyl-tRNA, it is recognized by the peptidyl transfer center of the ribosome, which catalyzes the transfer of the nascent polypeptide to the modified tyrosine of puromycin. The mRNA is now covalently attached to the corresponding translated peptide via the puromycin, and the ribosomes are stalled. To promote the covalent attached (or fusion) of the translated polypeptide to the encoding mRNA strand, the reaction mixture is preferably exposed to KCl and $Mg(OAc)_2$ and then maintained at a temperature below 0° C. for sufficient duration to yield the fused product. At this point, the initial pool or library mRNAs have now been translated and linked via puromycin to the peptides that they encode in a stable molecular conjugate referred to as an mRNA-peptide fusion.

To facilitate glycosylation of the translated polypeptide, translation of the mRNA strand is carried out using one or more modified amino acids comprising a reactive side chain. One exemplary amino acid is homopropargylglycine, which is efficiently recognized for incorporation into the polypeptide corresponding to the location of Met codons. Thus, for purposes of translation, homopropargylglycine constitutes a modified methionine. Homopropargylglycine can be prepared using the procedures of Shimizu et al., *Nat Biotech* 19:751-755 (2001); Josephson et al., *J. Am. Chem. Soc.* 127:11727-11735 (2005); Guillen et al., *J. Am. Chem. Soc.* 134:10469-10477 (2012); Shimizu et al., *Methods Mol Biol.* Vol. 607, p 11-21 (2010); and Ma et al., Ribosome Display and Related Technologies; Douthwaite, J. A., Jackson, R. H., Eds.; Springer New York: *Methods Mol Biol.* Vol. 805, p 367-390 (2012), which are hereby incorporated by reference in their entirety. Other exemplary amino acids are p-azidophenylalanine and p-ethynyl-phenylalanine, which are efficiently recognized for incorporation into the polypeptide corresponding to the location of Phe codons when the PheRS A294G substrate is used (see Hartmann et al., *PlosOne* DOI 10.1371/journal.pone.0000972 (2007), which is hereby incorporated by reference in its entirety. Yet another exemplary amino acid is L-allyl glycine which is efficiently recognized for incorporation into the polypeptide corresponding to the location of Leu codons when the editing deficient LeuRS D345A substrate is used. With modified amino acylated-tRNAs introduced into the reaction mixture in the absence of one or more natural amino acylated-tRNAs, the modified amino acids are introduced into the polypeptide chain (Guillen et al., *J. Am. Chem. Soc.* 134:10469-10477 (2012), which is hereby incorporated by reference in its entirety).

The resulting translated polypeptide can include any number of amino acids, preferably between about 10 to about 80 amino acids, more preferably between about 15 and about 70 amino acids. In certain embodiments, the polypeptide can include about 20 amino acids, about 25 amino acids, about 30 amino acids, about 35 amino acids, about 40 amino acids, about 45 amino acids, about 50 amino acids, about 55 amino acids, about 60 amino acids, or about 65 amino acids. The polypeptide can include one or more of the modified amino acid residues, preferably between about 2 to about 10 of the modified amino acid residues. In certain embodiments, the polypeptide can include 2 to 5 modified amino acids, or 6 to 10 modified amino acids.

The modified amino acids can be located at adjacent positions (i.e., where one modified amino acid is linked via peptide bond to another modified amino acid) or at nonadjacent positions (i.e., where no two modified amino acids are linked via peptide bond to one another). In certain embodiments, the resulting polypeptide includes a plurality of modified amino acids, some of which are adjacent to one another and some of which are not adjacent to another modified amino acid.

After forming the mRNA-polypeptide fusion, the one or more monosaccharides or oligosaccharides are attached using appropriate click chemistry reactions, which include thiol-ene reactions (reaction of a thiol bond across an alkene or alkyne by either a free radical or ionic mechanism) (see, e.g., Hoyle et. al., *Angew. Chem. Int. Ed.* 49:1540-1573 (2010), which is hereby incorporated by reference in its entirety) as well as azide-alkyne cycloaddition reactions (reaction of an azido group with a terminal or internal alkyne) (see, e.g., Temme et al., *Chem. Eur. J.* 19:17291-17295 (2013) and Hong et al., *Angew. Chem. Int. Ed.* 48:9879-9883 (2009), which are hereby incorporated by reference in their entirety).

The monosaccharide or oligosaccharide to be linked to the modified amino acid(s) of the polypeptide can be any saccharide modified with a click chemistry reactive group (e.g., thiol, azide, alkyne or alkene). Suitable monosaccharides include, without limitation glucose, galactose, mannose, arabinose, fucose, rhamnose, sialic acid, and N-acetyl-glucosamine.

Suitable oligosaccharides include branched or unbranched oligosaccharide that include at least 3 saccharide moieties, typically from about 3 saccharide moieties up to about 20 saccharide moieties. The saccharide moieties include those identified as suitable monosaccharides.

Exemplary N-linked glycan structures include high mannose N-glycans present in the human lung:

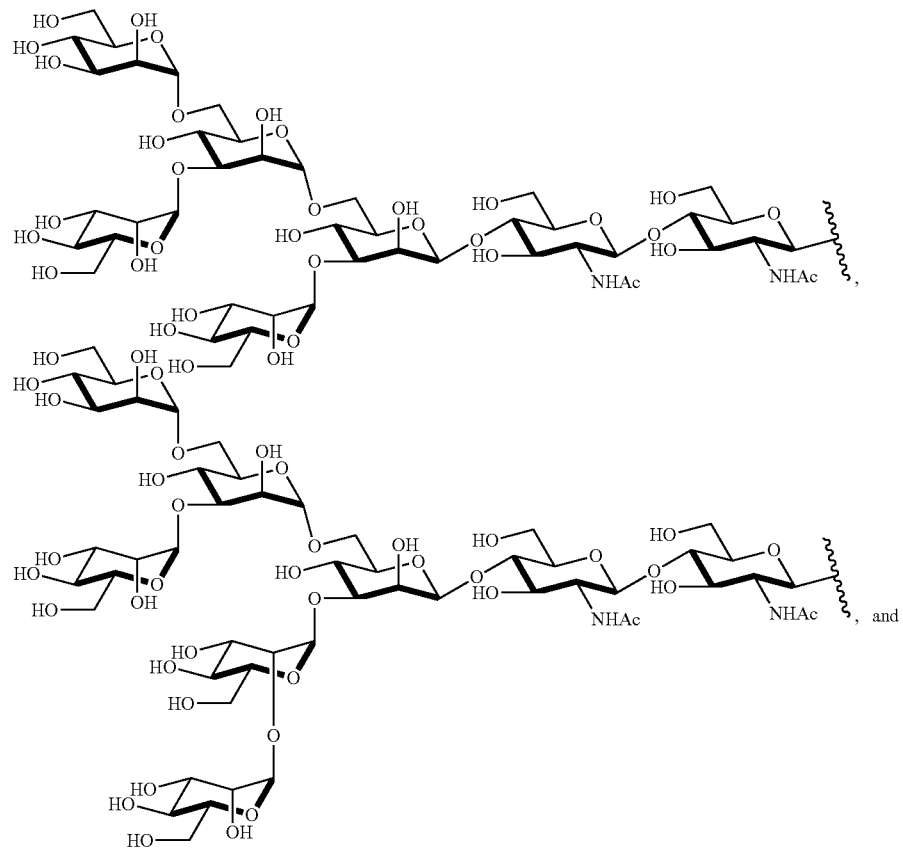

-continued

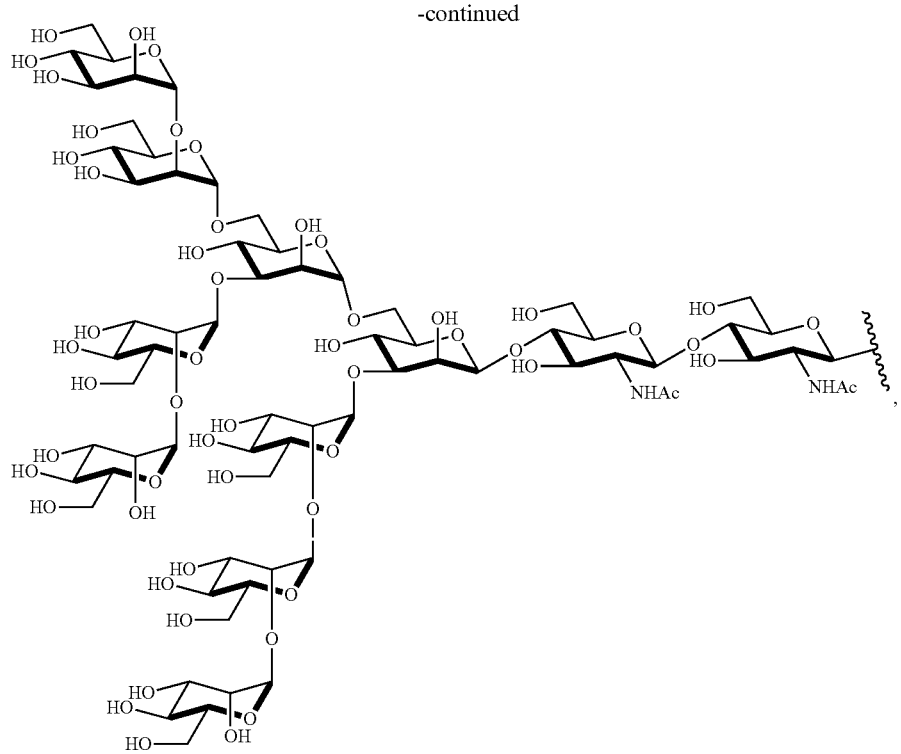

where saccharide subunits include N-acetylglucosamine and mannose as shown (Walther et al., *PLOS Pathogens* 9(3): e1003223 (2013), which is hereby incorporated by reference in its entirety).

Exemplary N-linked glycan structures recognized by HIV broadly neutralizing antibodies (PGT151-PGT158) include multi-antennary complex-type N-glycans with terminal galactose with and without sialic acid residues:

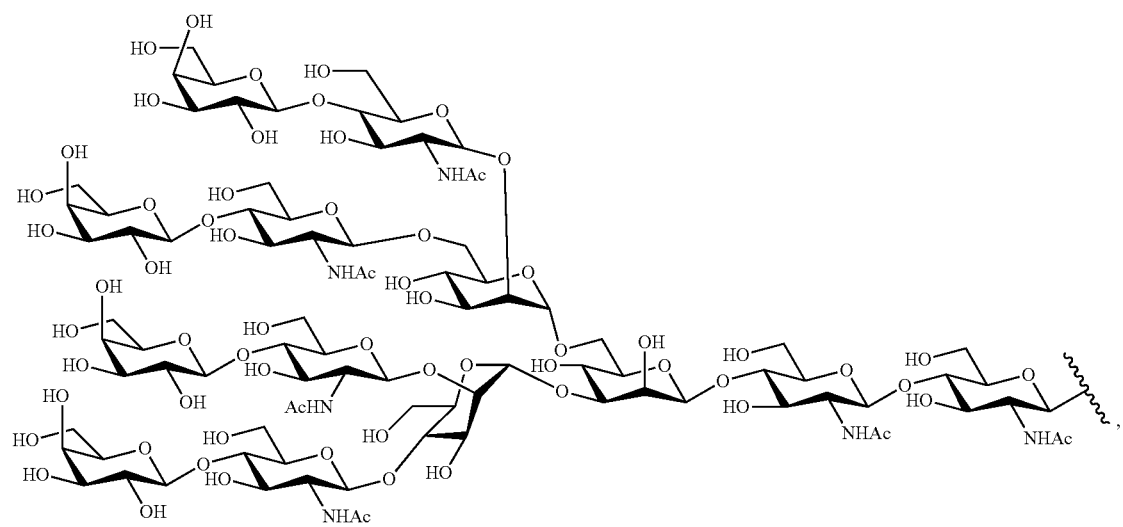

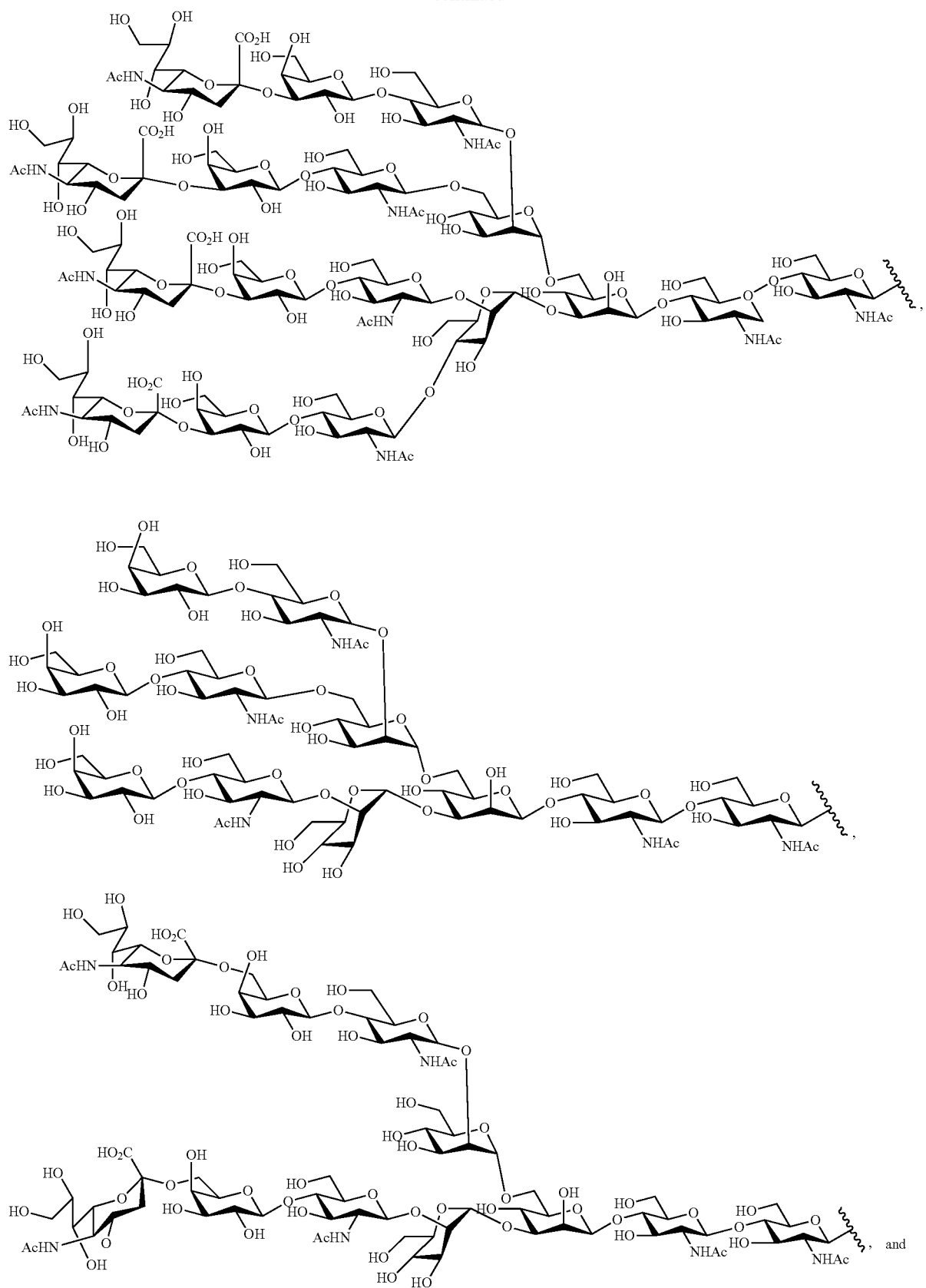

-continued

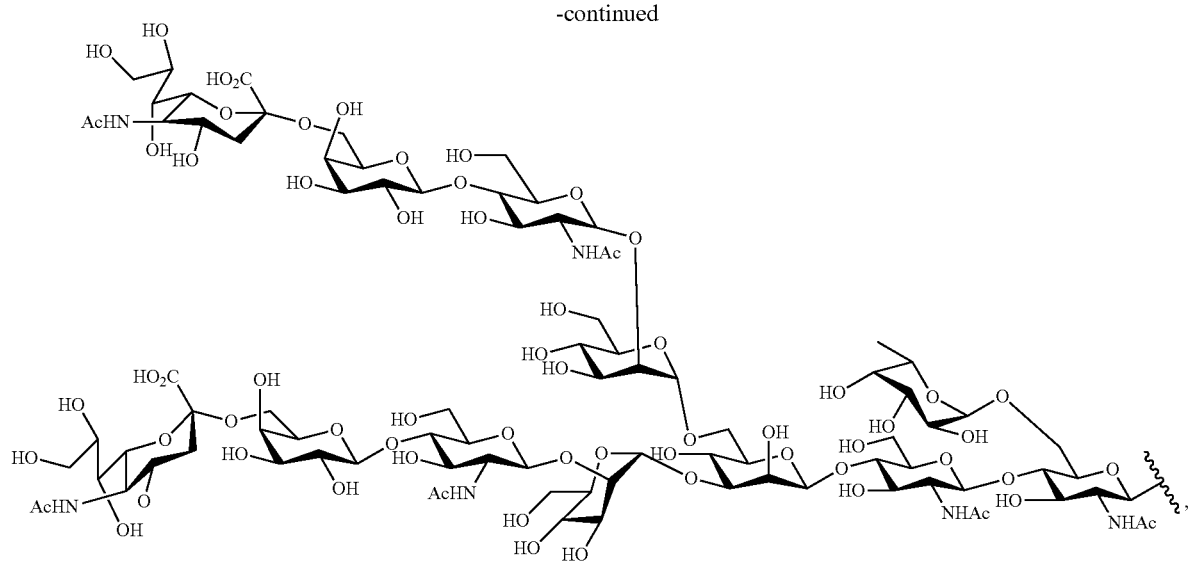

where saccharide subunits include N-acetylglucosamine, mannose, galactose, sialic acid, and fucose as shown (Walther et al., *PLOS Pathogens* 9(3):e1003223 (2013) and Falkowska et al., *Immunity* 40(5): 657-6688 (2014), which are hereby incorporated by reference in their entirety).

Additional exemplary N-linked glycan structures include hybrid-type glycans recognized by HIV antibody PG16:

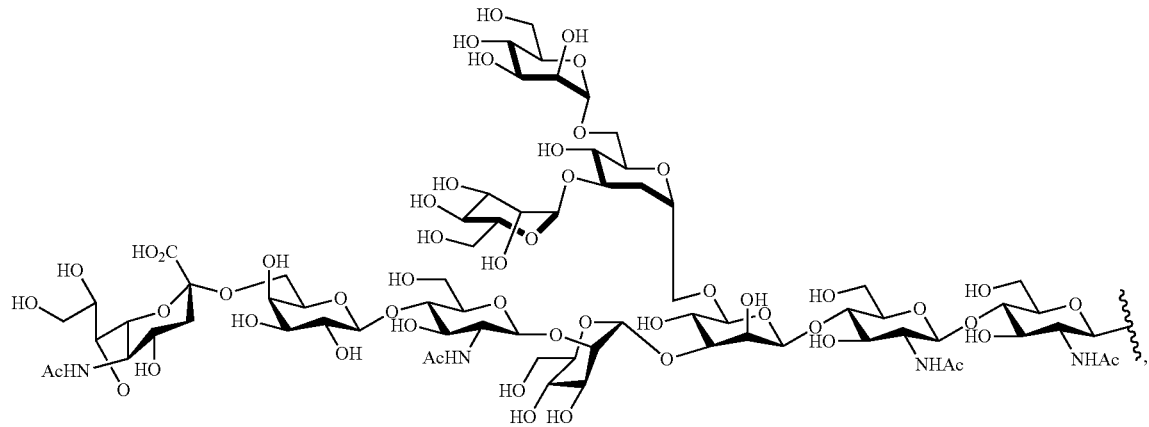

where saccharide subunits include N-acetylglucosamine, mannose, galactose, and sialic acid (Pancera et al., *Nature Struct Mol Biol.* 20(7): 804-13 (2013), which is hereby incorporated by reference in its entirety).

Derivatization of the monosaccharides and/or oligosaccharides to introduce the reactive azido, alkynyl, alkenyl, or thiol group can be achieved using known procedures. See, e.g., Hoyle et al., *Angew. Chem. Int. Ed.* 49:1540-1573 (2010); Temme et al., *Chem. Eur. J.* 19:17291-17295 (2013); Hong et al., *Angew. Chem. Int. Ed.* 48:9879-9883 (2009); MacPherson et al., *Angew. Chem. Int. Ed.* 50:11238-11242 (2011); Kolb et al., *Angew. Chem. Int. Ed.* 40:2004-2021 (2001); Rostovtsev et al., *Angew. Chem. Int. Ed.* 41:2596-2599 (2002); Gierlich et al., *Org. Lett.* 8:3639-3642 (2006); Gierlich et al., *Chem. Eur. J.* 13:9486-9494 (2007), each of which is hereby incorporated by reference in its entirety).

Additional exemplary modified oligosaccharides (suitable for click reaction) include the following:

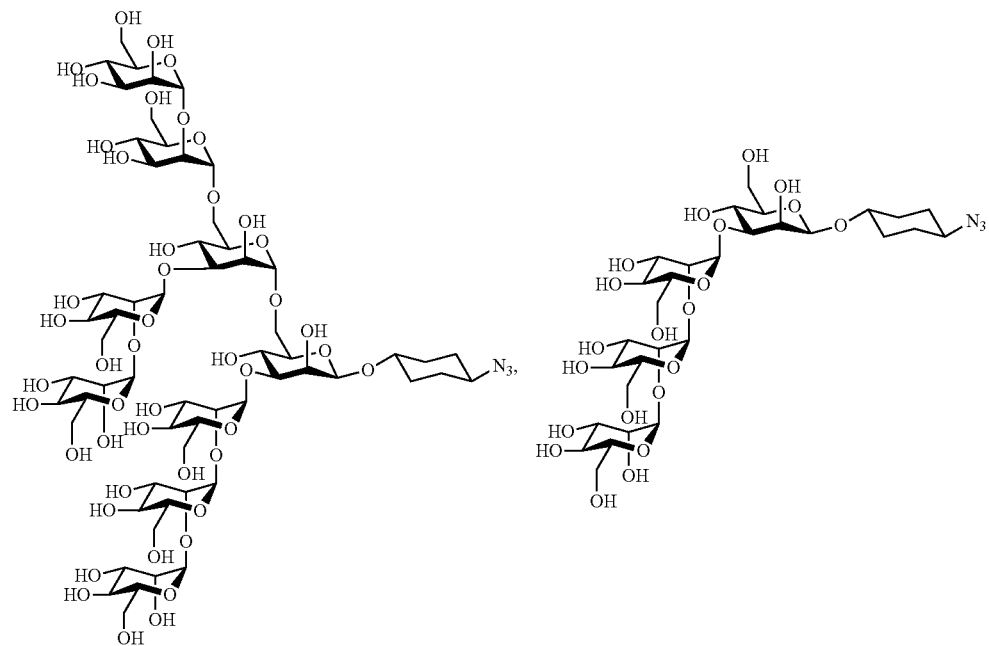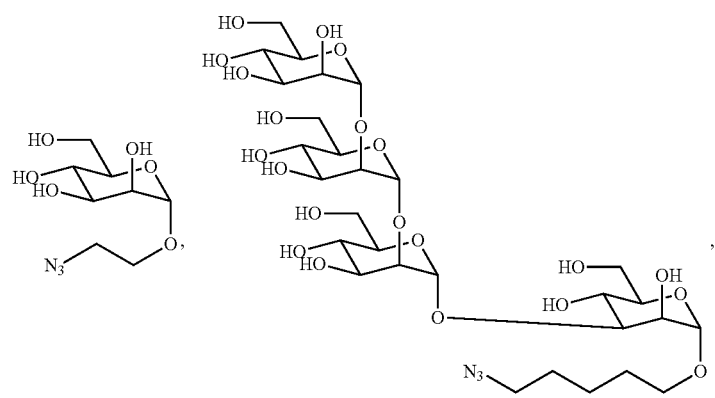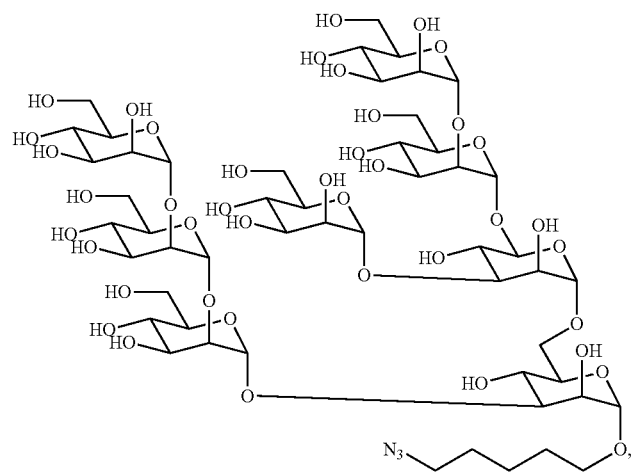

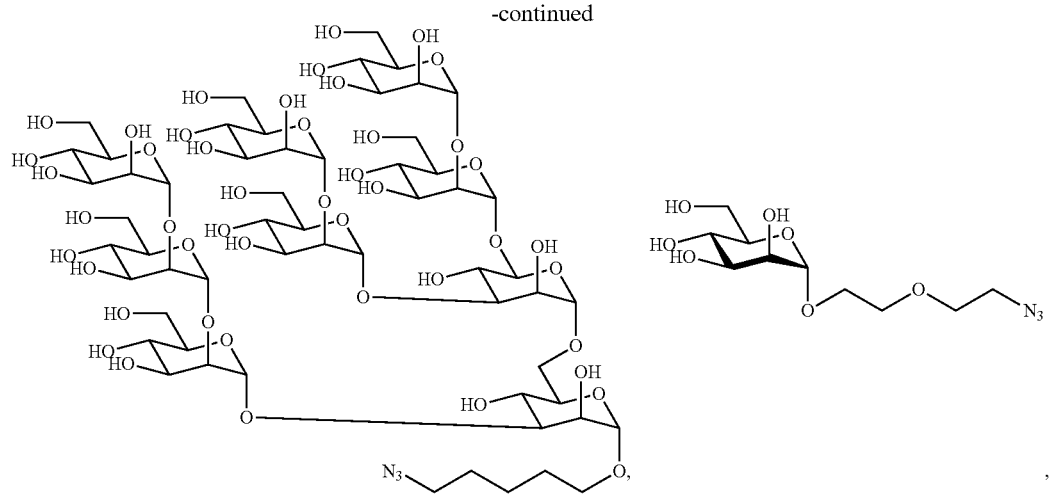
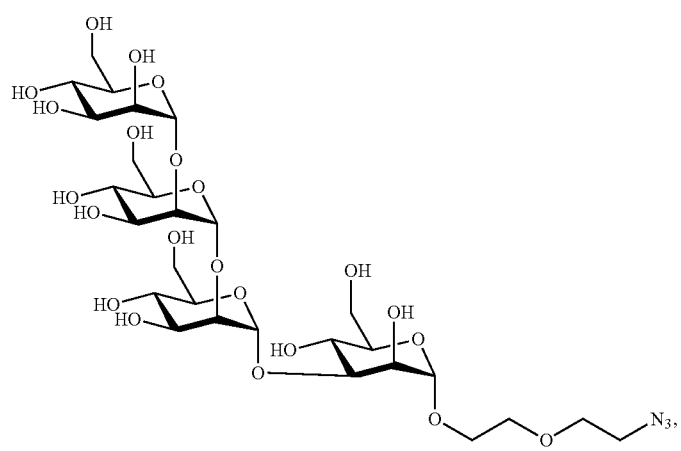
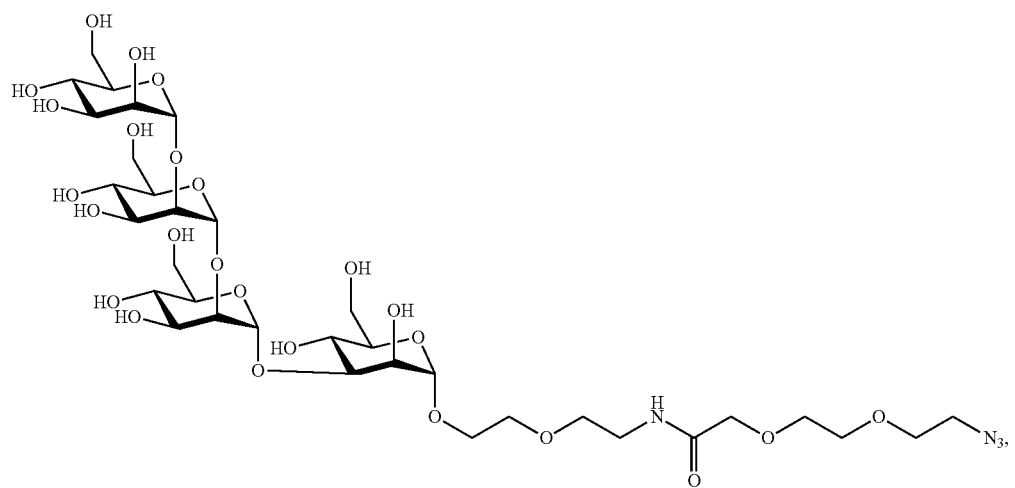
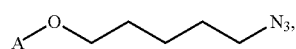

where A is the mono- or oligosaccharide,

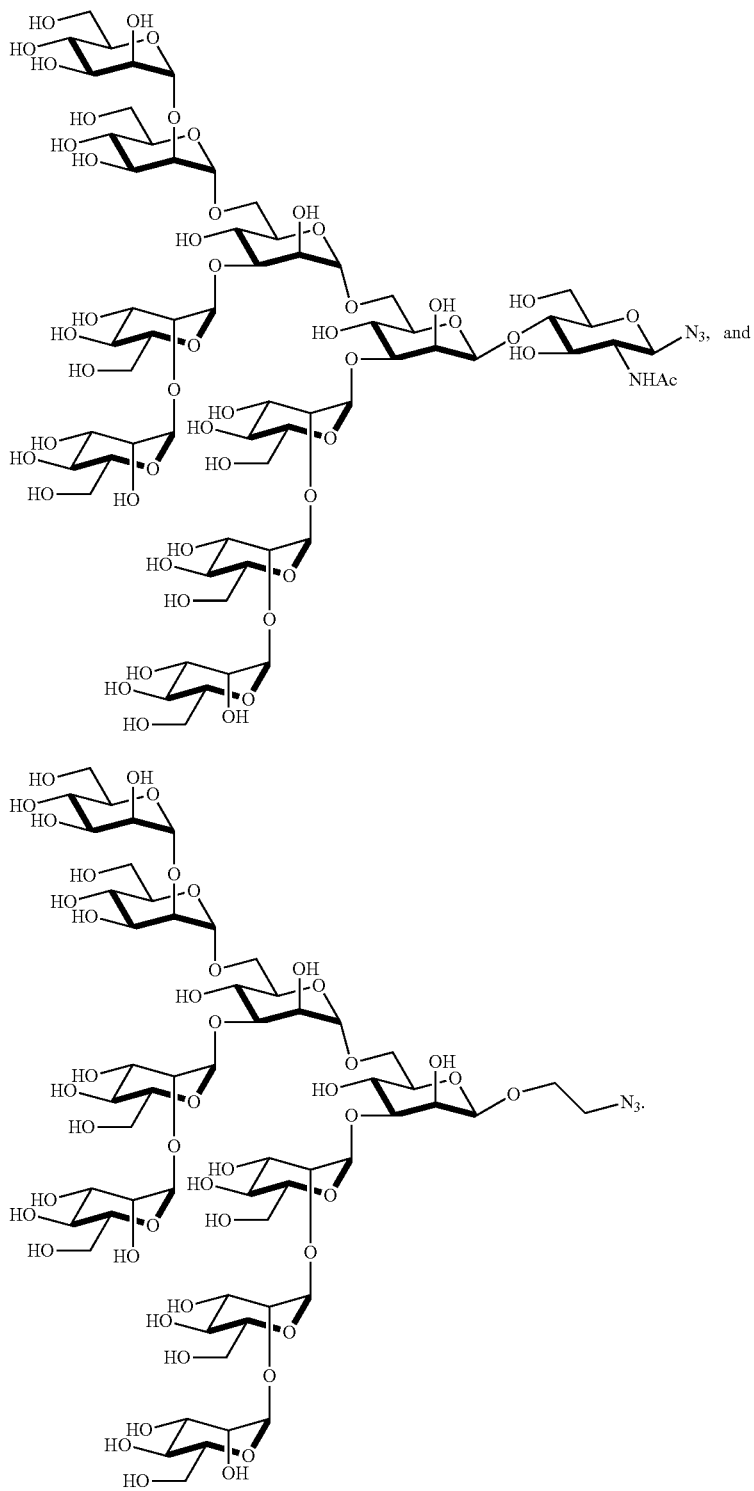

As an alternative to the above structures bearing an azide functional group, equivalent structures can be created with alkynyl, alkenyl, or thiol functional groups.

Tumor-associated carbohydrates ("TACAs") can be linked to lipids such as gangliosides, or to proteins such as mucins. Exemplary glycolipid TACAs includes GM2, GD2, GD3, fucosyl-GM1, Globo-H, and Lewis$^y$ (Le$^y$) and the glycoprotein TACAs include the truncated Tn-, TF and sialylated Tn (STn)-antigens as well as Globo-H and Le$^y$ (Buscas et al., *Chem Commun* (Camb). (36): 5335-49 (2009), which is hereby incorporated by reference in its entirety):

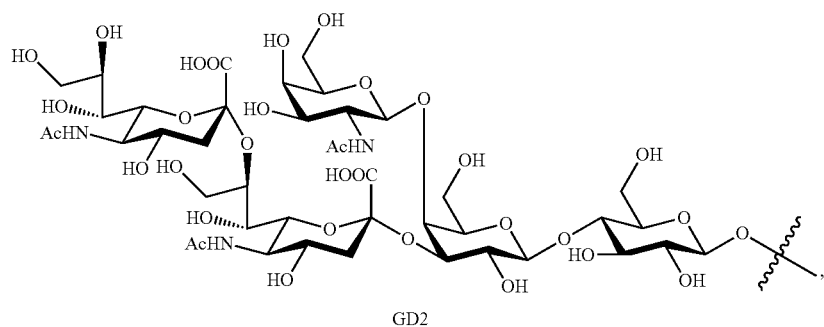
GD2
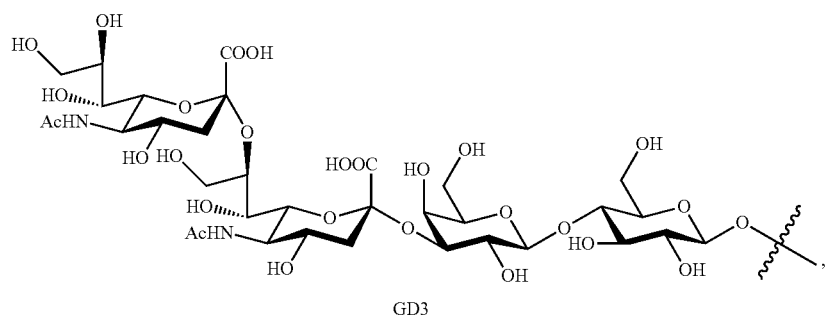
GD3
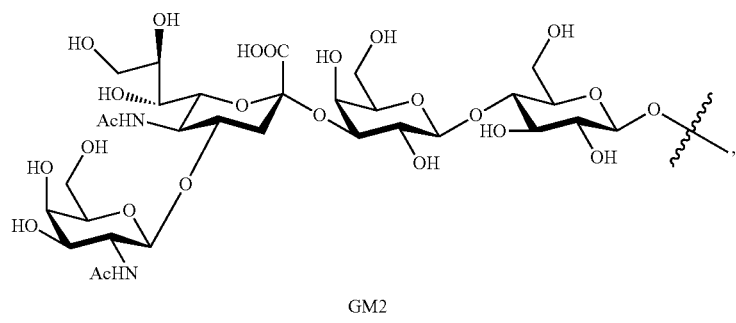
GM2
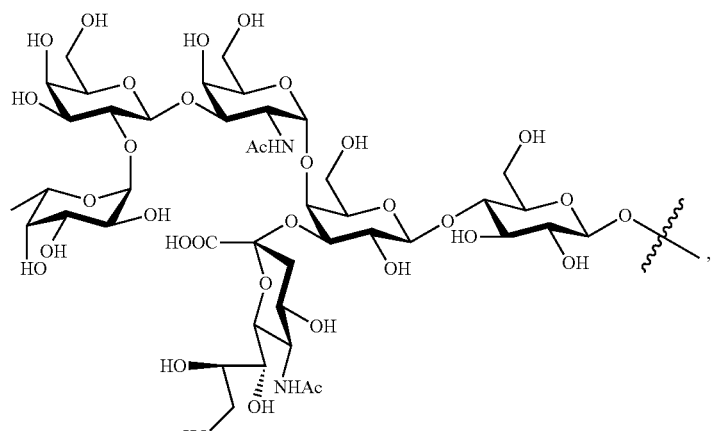
Fucosyl GM$_1$

-continued
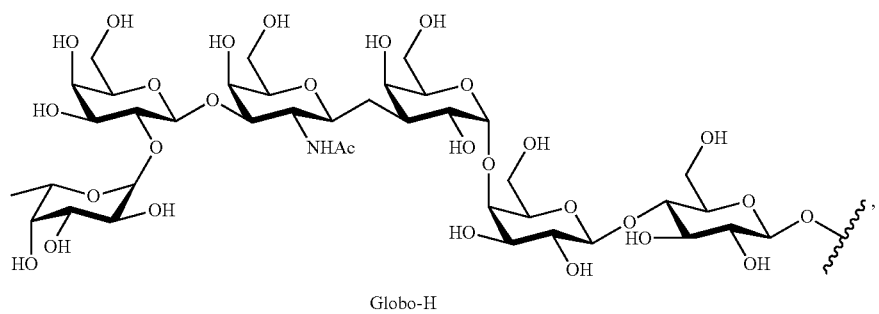
Globo-H
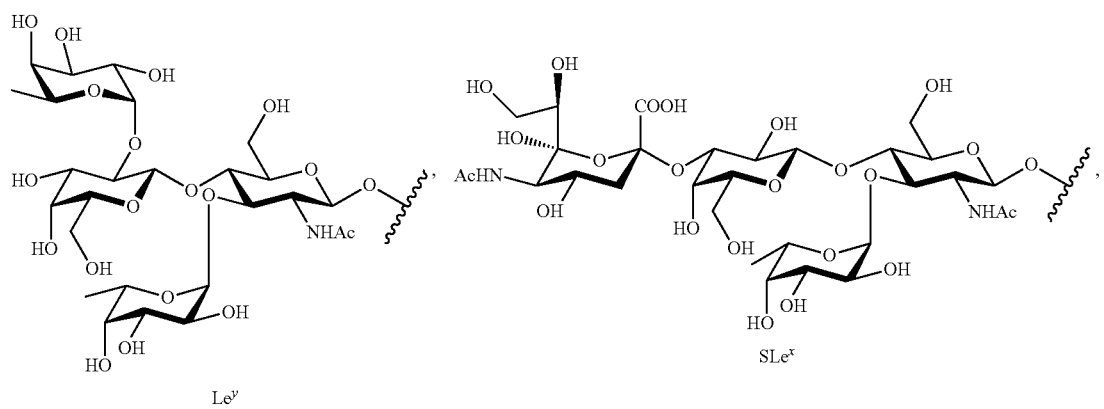
Le$^y$
SLe$^x$
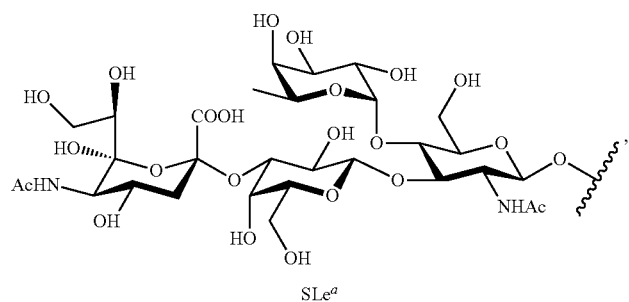
SLe$^a$
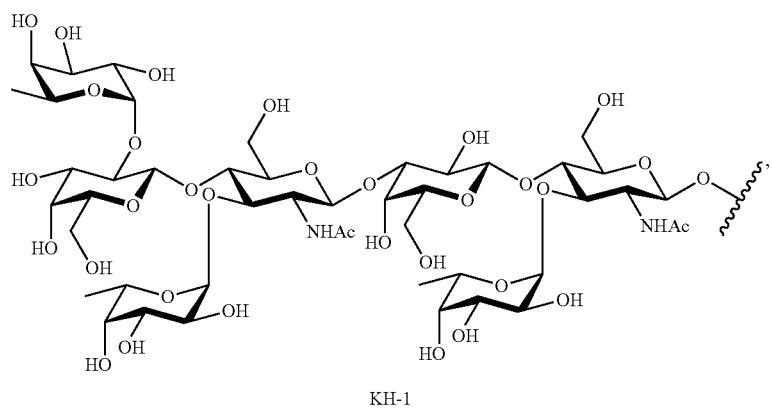
KH-1

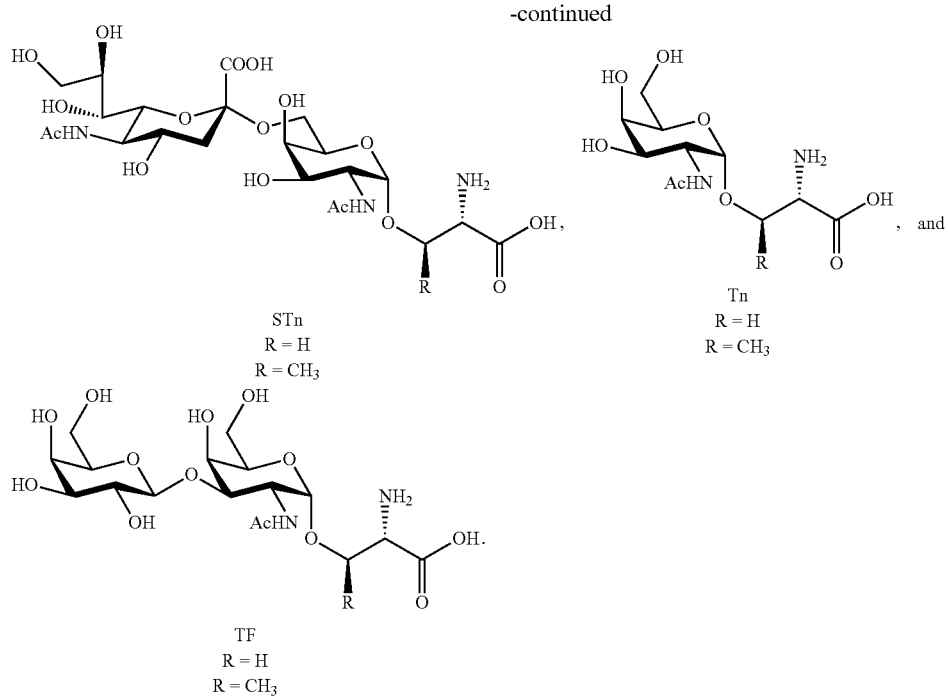

These structures can be derivatized to include an azido, alkynyl, alkenyl, or thiol group using the procedures identified above.

An exemplary GPI glycan includes the synthetic non-toxic malarial GPI glycan structure NH$_2$—CH$_2$—CH$_2$—PO$_4$-(Manα1-2)6Manα1-2Manα-6Manα1-4GlcNH$_2$α1-6myo-inositol-1,2-cyclic-phosphate (Schofield et al., *Nature* 418(6899):785-9 (2002), which is hereby incorporated by reference in its entirety):

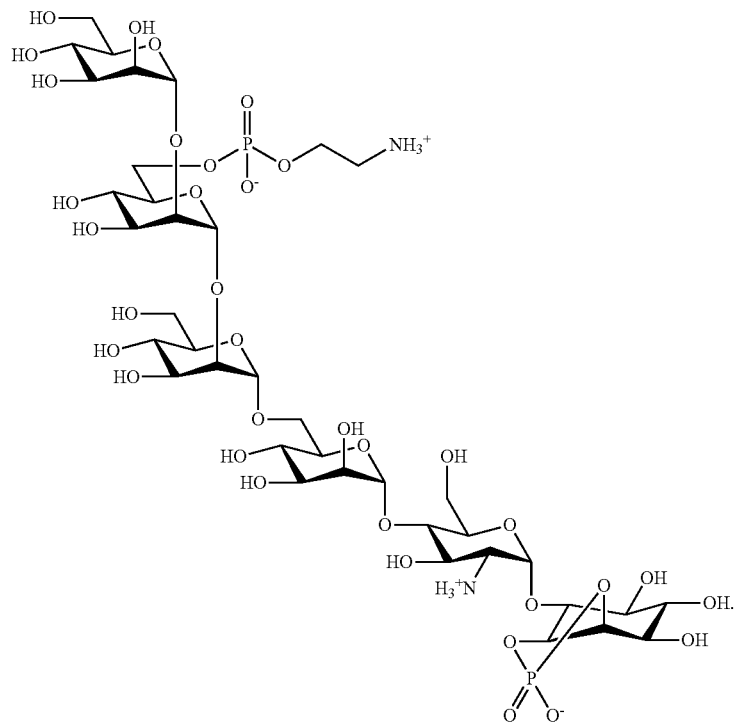

This structure can be derivatized to include an azido, alkynyl, alkenyl, or thiol group using the procedures identified above.

As a result of the click reaction between the modified amino acid and the modified monosaccharide or oligosaccharide, the glycopolypeptide contains a linker molecule between the polypeptide chain and the monosaccharide or oligosaccharide. Exemplary linker molecules include, without limitation:

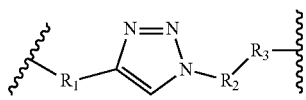

(resulting from the azide-alkyne reaction) or

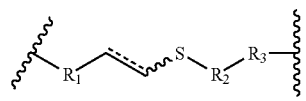

(resulting from the alkene/alkyne-thiol reaction), wherein each of $R_1$ and $R_2$ is optionally a direct link or independently selected from the group consisting of a linear or branched $C_1$ to $C_{18}$ hydrocarbon that is saturated or mono- or poly-unsaturated, optionally interrupted by one or more nonadjacent —O—, —C(=O)—, or —$NR_4$—; a substituted or unsubstituted $C_3$ to $C_{10}$ cycloalkandiyl, a substituted or unsubstituted aryl diradical; substituted or unsubstituted heteroaryl diradical; a monosaccharide diradical; or a disaccharide diradical; $R_3$ is optional and can be —O—, —S—, or —$NR_4$—; and $R_4$ is H or a $C_1$ to $C_{10}$ alkyl.

Although flexible linkers may be used, the linker between the monosaccharide/oligosaccharide and the modified amino acid(s) of the glycopeptide preferably includes or more cyclic moieties which offer some rigidity to the resulting glycosyl group.

After recovering the glycopolypeptide-mRNA fusion, a reverse transcription reaction procedure is performed using the mRNA strand as a template to form a cDNA strand. After synthesis of the cDNA strand, the resulting product includes the glycopolypeptide linked to the mRNA-cDNA duplex via puromycin. Collectively, these structures constitute the first pool available for selection against a target molecule.

Exemplary target molecules suitable for selection include those that bind to glycosylated naturally occurring proteins, such as monoclonal antibodies that bind to glycosylated epitopes (i.e., carbohydrate-binding monoclonal antibodies). Suitable carbohydrate-binding monoclonal antibodies include those that are neutralizing against a pathogen, as well as those that are cytotoxic against a cancer cell.

Exemplary carbohydrate-binding neutralizing monoclonal antibodies include those that bind specifically to N-glycosylated HIV gp120 or N-glycosylated HSV-2 gD. Specific examples of these neutralizing monoclonal antibodies include, without limitation, 2G12, PG9, PG16, PGT121, PGT122, PGT123, PGT125, PGT126, PGT127, PGT128, PGT129, PGT130, PGT131, PGT135, PGT136, PGT137, PGT141, PGT142, PGT143, PGT144, PGT145, PGT151, PGT152, PGT153, PGT154, PGT155, PGT156, PGT157, PGT158, CH01, CH02, CH03, CH04, 10-1074, 10-996, 10-1146, 10-847, 10-1341, 10-1121, 10-1130, 10-410, 10-303, 10-259, 10-1369, and E317.

Exemplary carbohydrate-binding cytotoxic monoclonal antibodies include those that binds specifically to O-glycosylated cancer-specific human podoplanin; aberrantly O-glycosylated cancer-specific MUC1, aberrantly O-glycosylated cancer-specific Integrin α3β1, or N-glycosylated cancer-specific antigen RAAG12. Specific examples of these cytotoxic monoclonal antibodies include, without limitation, LpMab-2 (Kato et al., Sci Rep. 4:5924 (2014), which is hereby incorporated by reference in its entirety), 237 MAb (Brooks et al., PNAS 107(22):10056-10061 (2010), which is hereby incorporated by reference in its entirety), RAV12 (Loo et al., Mol. Cancer Ther. 6(3):856-65 (2007), which is hereby incorporated by reference in its entirety), BCMab1 (*Clinical Cancer Research* 20(15):4001 (2014), which is hereby incorporated by reference in its entirety), DF3 and 115D8 (Tang et al., *Clin Vaccine Immunol.* 17(12): 1903-1908 (2010), which is hereby incorporated by reference in its entirety), huHMFG1, HT186-B7, -D11 and -G2 sc-FVs (Thie et al., *PLoS One* 6(1): e15921 (2011), which is hereby incorporated by reference in its entirety), and GOD3-2C4 (Welinder et al. *Glycobiol.* 21(8):1097-107 (2011), which is hereby incorporated by reference in its entirety).

Selection of library members that bind to the target protein—in the case of the monoclonal antibodies, mimicking the native glycosyl-epitope to which the antibody binds—is carried out in liquid medium. Briefly, the library is introduced into the selection medium with the target protein. If the target protein is biotinylated, streptavidin-labeled magnetic beads can be used to recover library members that bind to the target protein. Alternatively, where the target protein is a monoclonal antibody, Protein A or Protein G-labeled magnetic beads can be used to recover library members that bind to the target monoclonal antibody. Regardless of the type of beads used, the beads can be magnetically isolated and washed with selection buffer. To elute the selected library members, the beads can be resuspended in selection buffer and then heated to disrupt the affinity binding between library member and target. Recovered supernatant contains the eluted library members.

Following recovery of the selected library members, PCR amplification is used to amplify the cDNA portion of the library member mRNA-cDNA duplexes. PCR using Taq DNA polymerase (Roche) is performed using forward and reverse primers, and the amplified DNAs can be purified and used to regenerate the next selection round. In certain embodiments, error prone PCR can be used to facilitate evolution of the library.

In regenerating the next select round, the transcription, puromycin linkage, translation, and reverse transcription steps described above are used to generate a next generation pool (i.e., the glycopolypeptides linked mRNA-cDNA duplex via puromycin).

Differences in the selection protocol can performed in subsequent rounds. For instance, the selection stringency can be increased to promote the selection of high affinity binding of pool members. In certain embodiments the temperature can be varied from about 18 to 22° C. in early rounds to temperatures greater than 22° C. or even greater than 27° C. (e.g., about 32° C. to about 42° C.) in later rounds. Any such variation in temperature can be used. In alternative embodiments the target protein concentration can be varied from about 25 to about 200 nM in early rounds, and reduced to about 10 to about 80 nM, or about 5 to about 25 nM in later rounds. Any such variation in target protein concentration can be used. In certain embodiments the duration of the selection step can also be reduced from about 10 to about 30 minutes in early rounds, to about 5 to about 20 minutes in later rounds. Any such variation in duration of the selection step can be used. In another embodiment, the introduction of competitor molecules for negative selection can be introduced in later rounds, including the introduction of free monosaccharides or oligosaccharides, the introduction of unglycosylated peptides (removing polypeptides which bind to target protein without being glycosylated), the introduction of unmodified magnetic beads, e.g., streptavidin, Protein A, or Protein G-conjugated beads (removing polypeptides or glycopolypeptides that bind directly to a solid support), or combinations thereof. Any number of negative selection steps can be employed. In yet another embodiment, the number and conditions of the wash steps can be made more stringent during later selection rounds.

In between rounds or after the final round, the individual, selected pool members can be sequenced and, thus, the polypeptide sequence identified. Having identified the polypeptide sequence, individual glycopolypeptides can be synthesized such that the molecule excludes the puromycin linker that links the polypeptide sequence to the mRNA transcript encoding the same. Polypeptide synthesis can be carried out using, e.g., standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including the Applied Biosystems 431A, 433A synthesizers and Peptide Technologies Symphony or large scale Sonata or CEM Liberty automated solid phase peptide synthesizers. The modified amino acids can be substituted during solid phase synthesis to allow for glycosylation in the same manner as the selected glycopolypeptides.

The amino acids used during synthesis can be L amino acids, D amino acids, or a mixture of L and D amino acids. As noted above, the length of the glycopolypeptide can be any length, but preferably between about 10 to about 80 amino acids.

The glycopolypeptides of the present invention include one or more of the modified amino acid residues having a sidechain comprising a monosaccharide or an oligosaccharide, and the glycopolypeptide binds specifically to a carbohydrate-binding monoclonal antibody with an affinity of less than 100 nM.

In certain embodiments, the glycopolypeptide binds specifically to the carbohydrate-binding monoclonal antibody with an affinity ($K_d$) of less than 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM.

In preferred embodiments, the glycopolypeptide binds specifically to the carbohydrate-binding monoclonal antibody with an affinity that is substantially the same as or lower than the affinity of the carbohydrate-binding monoclonal antibody to its naturally occurring binding partner. As used herein, an affinity that is "substantially the same" means that as Kd of glycopeptide for its target is less than 5×, less than 4×, less than 3×, less than 2×, or less than 1.5×Kd of the native binding partner to the monoclonal antibody. In certain embodiments, the glycopolypeptide binds specifically to the carbohydrate-binding monoclonal antibody with an affinity that is lower than the affinity of the carbohydrate-binding monoclonal antibody to its naturally occurring binding partner.

Exemplary neutralizing monoclonal antibodies and cytotoxic monoclonal antibodies are identified above. Using the selection protocol and the demonstrated results presented in the accompanying Examples, the present application demonstrates that glycopolypeptides that bind specifically to carbohydrate-binding monoclonal antibodies can be prepared and it is expected that these will display higher affinity for the monoclonal antibody than the monoclonal antibody has for its binding partner.

In certain embodiments, the carbohydrate-binding monoclonal antibody is HIV-1 neutralizing monoclonal antibody 2G12 and the glycopolypeptide includes the sequence XXSIPXYTY (SEQ ID NO: 2) where X is optional and can be any amino acid and X is the modified amino acid residue to which the oligosaccharide is linked. The oligosaccharide consists of a branched Man$_9$ moiety, which is linked via the click chemistry linker to the modified amino acids (in one embodiment that modified amino acid is a modified methionine such as homopropargyl-glycine).

Exemplary glycopolypeptides containing the consensus sequence of SEQ ID NO: 2 above include, without limitation,

| Sequence | SEQ ID NO: |
|---|---|
| XDTLHLKQIGGXPNCITQQDVRXTSIPYTYTWP | 3 |
| XLLKXVDQSRLXPVPGIGVTLHXRSIPYSYLPI | 4 |
| XRSTLNSLEYRXQYATEDPRIRXASIPYTYWWP | 5 |
| ATKTNCKREKTXDNHVTIXRSIPWYTYRWLPN | 6 |
| XATKTNFKREKTXDNHVTIXRSIPWYTYRWLPN | 7 |
| XATRTNCKREKTXDNHVTIXRSIPWYTYRWLPN | 8 |
| XATKTSCKREKTXDNHVTIXRSIPWYTYRWLPN | 9 |
| XVLPTIISTNVNPFRXLSIPTYTYLXPITWGEI | 10 |
| XTSIPYTYLNRSLWTNYRVNSWSXSKNVNVXPL | 11 |
| XERPSLXCGLSXLTSGGTQSSVXRSIPFYTYWW | 12 |
| XATKTNSKREKTXDNHVTIXRSIPWYTYRWLPN | 53 |
| XATKTNAKREKTXDNHVTIXRSIPWYTYRWLPN | 54 |
| XRSIPWYTYRWLPN | 55 |
| XDTLHLKQIGGXPNSITQQDVRXTSIPYTYTWP. | 62 |

In certain embodiments, the carbohydrate-binding monoclonal antibody is HIV-1 neutralizing monoclonal antibody 2G12 but the glycopolypeptide does not contain the consensus sequence of XXSIPXYTY (SEQ ID NO: 2). Exemplary glycopolypeptides that do not contain the consensus include, without limitation:

| Sequence | SEQ ID NO: |
|---|---|
| XHPYNTSRTSAXXAALKXQVTDXYALALFHRIL | 13 |
| XSPHLPVLLCKXVLNDGRRIVQXSCELPXVRRS | 14 |
| XLXFIRIYPTRXQYVYHAPLLTXVRXSPTGPLI | 15 |
| XCYVTVIPAXNXPEARLGIVCHXPGIRRGKALY | 16 |
| XSPHLPVLLSKXVLNDGRRIVQXSSELPXVRRS | 52 |
| XXAALKXQVTDXYALALFHRIL | 56 | wherein X is the modified amino residue to which the oligosaccharide is linked, in one embodiment that modified amino acid is a modified methionine such as homopropargylglycine.

In certain embodiments, the glycopolypeptide contains from three to five modified amino acid residues having a sidechain including a branched oligosaccharide containing 9 mannose moieties, wherein the glycopolypeptide binds specifically to HIV-1 neutralizing monoclonal antibody 2G12 with an affinity that is substantially the same as or lower than the affinity of the 2G12 antibody to gp120. Antibody 2G12 binds to gp120 with an affinity ($K_D$) of 5.8 nM (Hoorelbeke et al., *J. FEBS Lett.* 587:860-866 (2013), which is hereby incorporated by reference in its entirety).

More preferred glycopolypeptides are those that bind specifically to the 2G12 antibody with a $K_d$ value that is lower than 5 nM. Exemplary members of this embodiment include, without limitation, the following sequences:

| Sequence | SEQ ID NO: |
|---|---|
| XLXFIRIYPTRXQYVYHAPLLTXVRXSPTGPLI | 15 |
| XHPYNTSRTSAXXAALKXQVTDXYALALFHRIL | 13 |
| XCYVTVIPAXNXPEARLGIVCHXPGIRRGKALY | 16 |
| XSPHLPVLLCKXVLNDGRRIVQXSCELPXVRRS | 14 |
| XLLKXVDQSRLXPVPGIGVTLHXRSIPYSYLPI | 4 |
| XDTLHLKQIGGXPNCITQQDVRXTSIPYTYTWP | 3 |
| XRSTLNSLEYRXQYATEDPRIRXASIPYTYWWP | 5 |
| XATKTNCKREKTXDNHVTIXRSIPWYTYRWLPN | 6 |
| XTSIPYTYLNRSLWTNYRVNSWSXSKNVNVXPL | 11 |
| XVLPTIISTNVNPFRXLSIPTYTYLXPITWGEI | 10 |
| XSPHLPVLLSKXVLNDGRRIVQXSSELPXVRRS | 52 |
| XATKTNSKREKTXDNHVTIXRSIPWYTYRWLPN | 53 |
| XATKTNAKREKTXDNHVTIXRSIPWYTYRWLPN | 54 |
| XXAALKXQVTDXYALALFHRIL | 56 |
| XDTLHLKQIGGXPNSITQQDVRXTSIPYTYTWP | 62 | wherein X is the modified amino residue to which the oligosaccharide is linked, and in one embodiment that modified amino acid is a modified methionine such as homopropargylglycine. Of these, SEQ ID NOs: 13 and 15 exhibit the highest affinity with a $K_D$ of about 500 to 600 pM.

A further aspect of the invention relates to an immunogenic conjugate that includes a glycopolypeptide of the invention covalently or non-covalently bound to an immunogenic carrier molecule. Exemplary immunogenic carrier molecule include, without limitation, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

Any of a variety of conjugation methodologies can be utilized. See, e.g., Jennings et al., *J. Immunol.* 127:1011-8 (1981); Beuvery et al., *Infect. Immun* 40:39-45 (1993), each of which is hereby incorporated by reference in its entirety. In one approach terminal aldehyde groups can be generated through periodate oxidation, and the aldehydes are then reacted through reductive amination with free amino groups on the protein, mostly lysines, in the presence of sodium cyanoborohydride. In another approach, a carbodiimide reaction is performed to covalently link carboxylic groups to the lysine ε-amino groups on the carrier protein. The activation sites in this method are more random, compared to periodate activation.

A further aspect of the invention relates to a pharmaceutical composition that includes a pharmaceutically acceptable carrier and a glycopolypeptide or immunogenic conjugate of the invention.

Pharmaceutical compositions suitable for injectable or parental use (e.g., intravenous, intra-arterial, intramuscular, etc.) or intranasal use may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water, saline solutions, and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

The pharmaceutical compositions of the present invention may also be administered directly to the airways in the form of an aerosol. For use as aerosols, the compositions of the present invention in the form of a solution or suspension may be packaged in a pressurized aerosol container together with suitable propellants, for example, hydrocarbon propellants like propane, butane, or isobutane with conventional adjuvants. The pharmaceutical compositions of the present invention also may be administered in a non-pressurized form such as in a nebulizer or atomizer. Formulations suitable for intranasal nebulization or bronchial aerosolization delivery are also known and can be used in the present invention (see Lu & Hickey, "Pulmonary Vaccine Delivery," *Exp Rev Vaccines* 6(2):213-226 (2007) and Alpar et al., "Biodegradable Mucoadhesive Particulates for Nasal and Pulmonary Antigen and DNA Delivery," *Adv Drug Deliv Rev* 57(3):411-30 (2005), which are hereby incorporated by reference in their entirety.

The pharmaceutical compositions of the present invention can also include an effective amount of a separate adjuvant. Suitable adjuvants for use in the present invention include, without limitation, aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid, Quil A, non-infective *Bordetella pertussis*, QS-21, monophosphoryl lipid A, an alpha-galactosylceramide derivative, or PamCys-type lipids.

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Advanced Drug Delivery Reviews* 32:173-186 (1998), which is hereby incorporated by reference in its entirety) alone or optionally all combinations thereof are suitable for human administration.

The pharmaceutical compositions can also include one or more additives or preservatives, or both.

Effective amounts of the glycopolypeptide may vary depending upon many different factors, including mode of administration, target site, physiological state of the patient, other medications administered, and whether treatment is prophylactic or therapeutic. Treatment dosages need to be titrated to optimize safety and efficacy. The amount of glycopolypeptide immunogen depends on whether adjuvant is also administered, with higher dosages being required in the absence of adjuvant. The amount of a glycopolypeptide immunogen for administration sometimes varies from 1 µg-5 mg per patient and more usually from 5-1000 µg per injection for human administration.

The glycopolypeptides, immunogenic conjugates, and pharmaceutical compositions can be incorporated into a delivery vehicle to facilitate administration. Such delivery vehicles include, but are not limited to, biodegradable microspheres (MARK E. KEEGAN & W. MARK SALTZMAN, *Surface Modified Biodegradable Microspheres for DNA Vaccine Delivery*, in DNA VACCINES: METHODS AND PROTOCOLS 107-113 (W. Mark Saltzman et al., eds., 2006), which is hereby incorporated by reference in its entirety), microparticles (Singh et al., "Nanoparticles and Microparticles as Vaccine Delivery Systems," *Expert Rev Vaccine* 6(5):797-808 (2007), which is hereby incorporated by reference in its entirety), nanoparticles (Wendorf et al., "A Practical Approach to the Use of Nanoparticles for Vaccine Delivery," *J Pharmaceutical Sciences* 95(12):2738-50 (2006) which is hereby incorporated by reference in its entirety), liposomes (U.S. Patent Application Publication No. 2007/0082043 to Dov et al. and Hayashi et al., "A Novel Vaccine Delivery System Using Immunopotentiating Fusogenic Liposomes," *Biochem Biophys Res Comm* 261(3): 824-28 (1999), which are hereby incorporated by reference in their entirety), collagen minipellets (Lofthouse et al., "The Application of Biodegradable Collagen Minipellets as Vaccine Delivery Vehicles in Mice and Sheep," *Vaccine* 19(30):4318-27 (2001), which is hereby incorporated by reference in its entirety), and cochleates (Gould-Fogerite et al., "Targeting Immune Response Induction with Cochleate and Liposome-Based Vaccines," *Adv Drug Deliv Rev* 32(3):273-87 (1998), which is hereby incorporated by reference in its entirety).

The glycopolypeptides, immunogenic conjugates, and pharmaceutical compositions can be used to induce an immune response in an individual. The individual can be any mammal, particularly a human, although veterinary usage is also contemplated. This method is carried out by administering one of these active agents to an individual in a manner that is effective to induce an immune response against the glycopolypeptide. Because the glycopolypeptide mimics the native glycosylated epitope of a native target of the monoclonal antibody to which the glycopolypeptide was selected, certain glycopolypeptides can induce a carbohydrate-binding, neutralizing antibody response that is protective against a pathogen (e.g., viral or bacterial pathogen) and certain other glycopolypeptides can induce a carbohydrate-binding, cytotoxic antibody response against a cancer cell that expresses a glycosylated antigen.

For each of these embodiments, administration of the glycopolypeptides, immunogenic conjugates, and/or pharmaceutical compositions can be carried orally, parenterally, subcutaneously, intravenously, intramuscularly, intraperitoneally, by intranasal instillation, by implantation, by intracavitary or intravesical instillation, intraarterially, intralesionally, transdermally, intra- or peri-tumorally, by application to mucous membranes, or by inhalation. Administration of these agents can be repeated periodically.

Exemplary viruses include, without limitation, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1 or HIV-2), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Acute Respiratory Syndrome (SARS Co-V), Tick-borne Encephalitis virus, Varicella zoster virus, Venezuelan Equine Encephalitis virus, Yellow Fever virus, Western Equine Encephalitis virus, and West Nile virus.

The use of one or more of the glycopeptides according to SEQ ID Nos: 3-16 in an immunogenic conjugate or pharmaceutical composition is specifically contemplated for prophylactic or therapeutic treatment against HIV-1.

Exemplary bacteria include, without limitation, *Bacillus anthracis*, *Bordetella pertussis* B, *Borrelia burgdorferi*, *Chlamydia trachomatis*, *Clostridium difficile*, *Clostridium tetani*, *Candida albicans*, *Corynebacterium diphtheriae*, *Cryptococcus neoformans*, *Entamoeba histolytica*, *Escherichia coli*, *Francisella tularensis*, *Haemophilus influenzae* (nontypeable), *Helicobacter pylori*, *Histoplasma capsulatum*, *Moraxella catarrhalis*, *Mycobacterium leprae*, *Mycobacterium tuberculosis*, *Neisseria gonorrheae*, *Neisseria meningitides*, *Pseudomonas aeruginosa*, *Staphylococcus aureus*, Methicillin-resistant *Staphylococcus aureus*, *Streptococcus agalactiae*, *Streptococcus pneumoniae*, *Streptococcus pyogenes*, and *Yersinia pestis*.

For prophylactic treatment against viral or bacterial infection, it is intended that the glycopolypeptides, immunogenic conjugates, and pharmaceutical compositions of the present invention can be administered prior to exposure of an individual to the virus or bacteria and that the resulting immune response can inhibit or reduce the severity of the viral or bacterial infection such that the virus or bacteria can be eliminated from the individual. The glycopolypeptides, immunogenic conjugates, and pharmaceutical compositions of the present invention can also be administered to an individual for therapeutic treatment. In accordance with one embodiment, it is intended that the composition(s) of the present invention can be administered to an individual who is already exposed to the virus or bacteria. The resulting enhanced immune response can reduce the duration or severity of the existing viral or bacterial infection, as well as minimize any harmful consequences of untreated viral or bacterial infections. The composition(s) can also be administered in combination other therapeutic anti-viral or anti-bacterial regimen. In asymptomatic patients, treatment can begin at any age (e.g., 10, 20, 30 years of age). Treatment typically entails multiple dosages over a period of time. Treatment can be monitored by assaying antibody, or activated T-cell or B-cell responses to the therapeutic agent over time. If the response falls, a booster dosage is indicated.

The glycopolypeptides, immunogenic conjugates, and pharmaceutical compositions that induce a cytotoxic antibody response against a cancer cell antigen can be used to treat solid tumors and blood cancers (leukemia or lymphoma) that are characterized by expression of O-glycosylated cancer-specific human podoplanin; aberrantly O-glycosylated cancer-specific MUC1, aberrantly O-glycosylated cancer-specific integrin α3β1, or N-glycosylated cancer-specific antigen RAAG12.

Exemplary cancers that display one of the glycosylated cancer-specific antigen include colorectal cancer, gastric cancer, ovarian cancer, breast cancer, and pancreatic cancer, which display N-glycosylated RAAG12; squamous cell carcinoma, lung and esophageal carcinoma, testicular seminoma, malignant brain tumor, fibrosarcoma, malignant mesothelioma, bladder cancers, and testicular cancers that display O-glycosylated ppodoplanin; bladder cancers that display O-glycosylated integrin α3β1; breast cancer, ovarian cancer, lung cancer, pancreatic cancer, prostate cancer, and forms of leukemia that displays aberrantly O-glycosylated MUC1.

For cancer therapy, it is contemplated that the glycopolypeptides, immunogenic conjugates, and pharmaceutical compositions can be administered in combination with a chemotherapeutic agent, a radiation therapy, or alternative immunotherapeutic agent. The specific selection of chemotherapeutic agent, a radiation therapy, or alternative immunotherapeutic agent will depend on the type of cancer. These agents can also be administered in combination with surgical resection to remove cancerous tissue, with treatment being carried out before, after, or both before and after surgery.

For inducing the immune response, the amount of a glycopolypeptide for administration sometimes varies from 1 μg-5 mg per patient and more usually from 5-1500 μg per dose for human administration. Occasionally, a higher dose of 1-2 mg per injection is used. Typically about 10, 20, 50, or 100 μg is used for each human dose. The mass of glycopolypeptide immunogen also depends on the mass ratio of immunogenic epitope within the glycopolypeptide immunogen to the mass of glycopolypeptide immunogen as a whole. Typically, $10^{-3}$ to $10^{-5}$ micromoles of immunogenic epitope are used for each microgram of glycopolypeptide immunogen. The timing of injections can vary significantly from once a day, to once a year, to once a decade. On any given day that a dosage of glycopolypeptide immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster administration at time intervals, such as 6 week intervals. Another regimen consists of an immunization followed by booster injections 1, 2, and 12 months later. Another regimen entails an administration every two months for a prolonged period in excess of 12 months. Alternatively, booster injections can be on an irregular basis as indicated by monitoring of immune response.

In certain embodiments, multiple doses are given over a period of time, each using a different immunogenic oligonucleotide in an appropriate amount, as indicated above.

The glycopolypeptides of the invention can also be used to detect a neutralizing antibody in a patient sample (e.g., a serum sample). This method includes providing a glycopolypeptide of the invention, contacting the glycopolypeptide with a sample from an individual; and detecting whether the glycopolypeptide binds specifically to an antibody present in the sample, wherein the detection of the antibody is carried out using a label.

Exemplary labels include, without limitation, a radiolabel, fluorescent label, enzymatic label, chemiluminescent marker, biotinyl group, an epitope recognized by a secondary reporter, a magnetic agent, or a toxin.

The detection step is preferably carried using a suitable assay format. Exemplary assays include, without limitation, ELISA, radioimmunoassay, gel-diffusion precipitation reaction assay, immunodiffusion assay, agglutination assay, fluorescent immunoassay, immunoelectrophoresis assay, surface plasmon resonance assay, or biolayer interferometry assay. In certainly of these assay formats, a secondary antibody is used to label the antibody bound specifically to the glycopolypeptide. Depending on the type of assay, the glycopolypeptide can be in the solution phase or coupled to a solid surface.

EXAMPLES

The following examples are intended to illustrate practice of the invention, and are not intended to limit the scope of the claimed invention.

Materials and Methods for Examples 1-4

Proteins and Ribosomes for PURE System Translation:

Hexa-histidine tagged IF1, IF2, IF3, EF-Tu, EF-G, EF-Ts, RF1, RF3, RRF, MTF, MetRS, GluRS, PheRS, AspRS, SerRS, ThrRS, ArgRS, GlnRS, IleRS, LeuRS, TrpRS, AsnRS, HisRS, TyrRS, ValRS, ProRS, AlaRS, CysRS, LysRS, and GlyRS were expressed in *Escherichia coli* BL21 Star (DE3) (Invitrogen) and purified as previously described (Shimizu et al., *Nat Biotech* 19:751-755 (2001); Josephson et al., *J. Am. Chem. Soc.* 127:11727-11735 (2005); Shimizu et al., *Methods Mol Biol*. Vol. 607, p 11-21 (2010); and Ma et al., Ribosome Display and Related Technologies; Douthwaite, J. A., Jackson, R. H., Eds.; Springer New York: *Methods Mol Biol*. Vol. 805, p 367-390 (2012), which are hereby incorporated by reference in their entirety). Ribosomes were prepared combining the previously described protocols (Shimizu et al., *Methods Mol Biol*. Vol. 607, p 11-21 (2010); Subtelny et al., *J. Am. Chem. Soc.* 130:6131-6136 (2008); and Ohashi et al., *Biochem. Biophys. Res. Commun.* 352:270-276 (2007), which are hereby incorporated by reference in their entirety) with some modifications. *E. coli* A19 was grown and harvested as previously described (Subtelny et al., *J. Am. Chem. Soc.* 130:6131-6136 (2008), which is hereby incorporated by reference in its entirety). The pelleted cells were washed with ~300 mL of suspension buffer (10 mM HEPES-KOH, pH 7.6, 10 mM magnesium acetate, 50 mM KCl, 7 mM β-mercaptoethanol) and spun at 5,000 g for 15 min. The pelleted cells were lysed in suspension buffer using a bead-beater and the cleared lysate was obtained by centrifuge (Subtelny et al., *J. Am. Chem. Soc.* 130:6131-6136 (2008), which is hereby incorporated by reference in its entirety). The supernatant (~20 mL) was mixed with the same volume of suspension buffer containing 3 M $(NH_4)_2SO_4$ and centrifuged at 36,000 g for 30 min. The resulted supernatant was filtered through a 0.45 μm membrane and subjected to FPLC purification to yield ribosomes as previously described (Shimizu et al., *Methods Mol Biol*. Vol. 607, p 11-21 (2010) and Ohashi et al., *Biochem. Biophys. Res. Commun.* 352:270-276 (2007), which are hereby incorporated by reference in their entirety).

PURE System Translation:

The PURE translation system with homopropargylglycine instead of methionine was prepared as previously described (Shimizu et al., *Nat Biotech* 19:751-755 (2001); Josephson et al., *J. Am. Chem. Soc.* 127:11727-11735 (2005); Guillen et al., *J. Am. Chem. Soc.* 134:10469-10477 (2012); Shimizu et al., *Methods Mol Biol*. Vol. 607, p 11-21 (2010); Ma et al., Ribosome Display and Related Technologies; Douthwaite & Jackson, Eds.; Springer New York: *Methods Mol Biol*. Vol. 805, p 367-390 (2012), which are hereby incorporated by reference in their entirety) with slight modifications. The reaction contained 50 mM HEPES-KOH (pH 7.6), 12 mM magnesium acetate, 2 mM spermidine, 100 mM potassium glutamate, 1 mM dithiothreitol (DTT), 1× Complete ULTRA, EDTA-free (Roche), 1 mM ATP, 1 mM GTP, 20 mM creatine phosphate (Calbiochem), 0.01 mg/l 10-formyl-5,6,7,8-tetrahydrofolic acid, 0.04 $ABS_{280}$ creatine kinase (Roche), 0.85 units/mL nucleoside 5'-diphosphate kinase from bovine liver (Sigma), 6.8 units/mL myokinase from rabbit muscle (Sigma), 100 units/mL inorganic pyrophosphatase, 48 $ABS_{260}$ tRNA from E. coli MRE 600 (Roche), 20 µg/mL MTF, 10 µg/mL IF1, 40 µg/mL IF2, 10 µg/mL IF3, 10 µg/mL EF-Tu, 50 µg/mL EF-Ts, 50 µg/mL EF-G, 10 µg/mL RF1, 10 µg/mL RF3, 10 µg/mL RRF, 0.66 µM MetRS, 0.23 µM GluRS, 0.027 µM PheRS, 0.21 µM AspRS, 0.45 µM SerRS, 0.011 µM ThrRS, 0.021 µM ArgRS, 0.27 µM GlnRS, 0.11 µM IleRS, 0.093 µM LeuRS, 0.23 µM TrpRS, 0.094 µM AsnRS, 0.21 µM HisRS, 0.18 µM TyrRS, 0.089 µM ValRS, 0.031 µM ProRS, 0.070 µM AlaRS, 0.41 µM CysRS, 0.18 µM LysRS, 0.024 µM GlyRS, 1.2 µM ribosomes, a mixture of 17 natural amino acids (3 mM each), with methionine-, cysteine-, and histidine-omitted and pre-adjusted pH to 7.6 with KOH, and 3 mM L-homopropargylglycine (Chiralix). To label the peptide radioisotopically, the reactions also contained L-[$^{35}$S]-cysteine (Perkin Elmer) or [2,5-$^{3}$H]-L-histidine (Moravek Biochemicals) in concentrations totaling 0.002-3 mM together with non-radioactive cysteine/histidine. These reactions were assembled on ice and initiated by the addition of mRNA (0.5-1.0 µM), followed by incubation at 37° C. for 1 h for mRNA display or 2 h for individual free peptide translation.

Click Reaction:

This optimized procedure was used in rounds 2-10 of selection, and in preparation of individual peptides for binding studies. $Man_9$-azide was synthesized as previously described (Temme et al., Chem. Eur. J. 19:17291-17295 (2013), which is hereby incorporated by reference in its entirety). The click reaction was performed combining the previously described protocols (Temme et al., Chem. Eur. J. 19:17291-17295 (2013) and Hong et al., Angew. Chem. Int. Ed. 48:9879-9883 (2009), which are hereby incorporated by reference in their entirety) with some modifications. The dry pellets of peptides or fusions in 0.5 mL microcentrifuge tubes were redissolved in 2.5 µL of 200 mM HEPES-KOH (pH 7.6) and 10 mM aminoguanidine hemisulfate (mixture A). In the case of fusions, ~0.05% (v/v) Triton X-100 was also added to the solution. 2.5 µL of a freshly-prepared solution of 2 mM $CuSO_4$, 2 mM Tris(3-hydroxypropyltriazolylmethyl)amine (THPTA) ligand and 6 mM $Man_9$-azide was transferred to a capless 0.5 mL microcentrifuge tube (mixture B). 3 µL of freshly-prepared solution of 2.5 mM $Man_9$-azide and 0.83 mM THPTA was added to a capless 0.5 mL microcentrifuge tube (mixture C). Sodium-L-ascorbate (less than 10 mg) was transferred to a capless 0.5 mL microcentrifuge tube. Then, the microcentrifuge tubes containing mixtures A, B and C, and sodium-L-ascorbate were purged under argon flow in the following manner. The microcentrifuge tubes were carefully positioned at the bottom of a 25 mL two-neck pear (pointy-bottom) flask. Positive argon pressure was applied through one neck, while a rubber septum with a purge needle was used to vent the system from the other neck. After 1 h of efflux, the septum was removed and, under Ar efflux, a pipette was inserted into the flask to add mixture B to mixture A. The sodium ascorbate was dissolved in degassed $H_2O$ to a final concentration of 100 mM, and 0.5 µL was added to the tube containing mixtures A and B. After recapping followed by 15 min of Ar purge, the vent needle was removed to keep the system under positive pressure. After an additional 1 h and 15 min, mixture C and an additional 0.25 µL of 100 mM sodium ascorbate was added to the reaction. After recapping and another 15 min of Ar purge, the vent needle was removed. After an additional 75 min, the click reaction mixture was taken out from the flask and quenched with 1.25 µL of 10 mM EDTA (pH 8.0). At this point, the total reaction volume was reduced to ~2-3 µL due to evaporation.

mRNA Display Selection:

The libraries of glycopeptide-mRNA-DNA fusions were prepared by modifying the previously described protocol to prepare the unnatural peptide-mRNA-DNA fusions with PURE system (Guillen et al., J. Am. Chem. Soc. 134:10469-10477 (2012), which is hereby incorporated by reference in its entirety). The fusions were radiolabeled with $^{35}$S-cysteine (rounds 1 and 2) or $^{3}$H-histidine (rounds 3-10), and the yields in various purification steps were monitored by liquid scintillation counting. During the procedure, the integrity of the fusion formation was checked (FIGS. 3A-C) by SDS-PAGE with visualization by autoradiography (in rounds 1 and 2) or fluorography (in rounds 3-10). Below, divided into subsections, the procedure in selection round 1 is first described, and then the modifications used in rounds 2-10 are described.

Preparation of Puromycin-Linked mRNA in Round 1:

The puromycin-linked mRNA for selection round 1 was prepared as follows. The antisense strands of synthetic library DNA (the Fixed library: 5'-CTAGCTACCTATAGC-CGGTGGTGATGGTGGTGATGACCCAGAGAACCG-GAGCC$N_{30}$CAT$N_{30}$CAT$N_{30}$CATTTAGCTGTCCTCCTTACTAAA GTTAACCCTATAGTGAGTCGTATT A-3'(SEQ ID NO: 17) and the Variable library: 5'-CTAGCTACCTATAGCCG-GTGGTGATG GTGATGGTGGCCTAAGCTACCG-GAGCC(SNn)$_{32}$CATTTAGCTGTCCTCCTTACTAAAGT TAACCCTATAGTGAGT CGTATTA (SEQ ID NO: 18), where uppercase N is an equimolecular mixture of G, A, T and C; S is an equimolecular mixture of G or C; lowercase n is a mixture of 40% T, 20% A, 20% G, and 20% C) were purchased from W. M. Keck Biotechnology Resource Laboratory, Yale University. The regions involved in the open reading frame in the constant regions of the two libraries were designed to have identical amino acid sequence but were not identical in nucleotide usage, so that the libraries would be PCR-amplified with different primer sets.

The Fixed and Variable library DNAs purified by denaturing polyacrylamide gel electrophoresis (PAGE), 780 and 300 pmol, respectively, were transcribed in the presence of 1.2 eq. of the DNA containing T7 promotor sequence (5'-TAATACGACTCACTATAGGGTT AACTTT AG-3') (SEQ ID NO: 19) using MEGAshortscript kit (Ambion). The transcripts were purified by denaturing 5% PAGE and photo-crosslinked with puromycin-containing oligonucleotide XL-PSO, Xuagccggug$A_{15}$ZZACCP, where X is C6 psoralen, lowercase nucleotides have 2'OMe, uppercase A and C are DNA, Z is Spacer 9 and P is puromycin (W.M. Keck Biotechnology Resource Laboratory, Yale University), by 365 nm UV irradiation as previously described (Kurz et al., Nucleic Acids Res. 28:e83 (2000) and Seelig, B. Nat. Protocols 6:540-552 (2011), which are hereby incorporated by reference in their entirety).

Translation to form alkynyl peptide-mRNA fusions in round 1: The radiolabeled alkynyl peptide-mRNA fusions for round 1 selection were produced as follows. The peptide-mRNA fusions were translated from 1 µM, RNA, of which ~50% was crosslinked with the puromycin-containing oligonucleotide XL-PSO, in 5.2 mL PURE system translation reactions containing [$^{35}$S]-cysteine for 1 h at 37° C. Following translation, KCl and magnesium acetate was added to facilitate fusion formation (Liu et al., *RNA-Ligand Interactions, Part B*; Academic Press Inc: San Diego, *Methods Enzymol*. Vol. 318, p 268-293 (2000), which is hereby incorporated by reference in its entirety), incubated for a 15 min at room temperature, and frozen as previously described (Josephson et al., *J. Am. Chem. Soc.* 127:11727-11735 (2005) and Guillen et al., *J. Am. Chem. Soc.* 134:10469-10477 (2012), which are hereby incorporated by reference in their entirety).

Purification and cDNA Synthesis of Fusions in Round 1:

The mRNA-peptide fusions were captured on oligo(dT) cellulose (Ambion), washed as previously described (Seelig, B. *Nat. Protocols* 6:540-552 (2011), which is hereby incorporated by reference in its entirety), and eluted with 0.1% (v/v) Tween-20 followed by 0.22 μm-filtration and ethanol precipitation. The recovered library fusions were purified with Ni-NTA agarose (Qiagen) under a denaturing condition to remove mRNA not fused with peptide using a similar procedure as previously described (Guillen et al., *J. Am. Chem. Soc.* 134:10469-10477 (2012), which is hereby incorporated by reference in its entirety), and desalted by gel filtration using NAP-5 columns (GE Healthcare) with the gel filtration buffer (10 mM Tris-HCl, pH 7.5, 1 mM EDTA, pH 8.0, 5 mM β-mercaptoethanol, 0.2% (v/v) Triton X-100) according to the manufacturer's protocol. The fusions were pelleted by ethanol precipitation and cDNA was synthesized using Superscript III Reverse Transcriptase (Invitrogen) with RT primers (5'-T$_{15}$GTGATGGTGGTGATGACCC AGAG-3' (SEQ ID NO: 20) for the Fixed library, 5'-T$_{15}$GTGATGGTGATGGTGGCCTAAGC-3' (SEQ ID NO: 21) for the Variable library) in the presence of Superase-In (Ambion) and 0.1% (v/v) Triton X-100 according to the manufacturer's protocol. The reverse transcribed fusions were pelleted by ethanol precipitation.

Click Glycosylation of Fusions in Round 1:

In round 1, the click reaction of fusions was not yet optimized and had to be done twice to give the desired glycosylation efficiency. The first click reaction was done under Ar with a setting as described in the section of "Click reaction" but with slightly different conditions: The starting volume was ~6 times larger, THPTA concentration was twice, and the addition of THPTA, Man$_9$-azide and sodium ascorbate in the middle of the reaction was not carried out. Since some insoluble pellets were observed at this point, the pellets were collected after click reaction by centrifugation and purified with Ni-NTA agarose under denaturing condition as described above. The eluted fusions were combined with the saved soluble fractions and desalted by gel filtration and ethanol precipitation. The recovered fusions were re-subjected to glycosylation using a condition similar to the optimized protocol as described in the section entitled "Click reaction" and then ethanol-precipitated.

Selection in Round 1:

The pellets of glycosylated peptide-mRNA-cDNA fusions were redissolved in 500 μL of selection buffer (20 mM Tris-HCl, pH 7.5, 100 mM NaCl, 0.1% v/v Triton X-100). The Fixed and Variable library fusions (yields of 23.0 and 14.4 pmol, equivalent to 1.4×10$^{13}$ and 0.86×10$^{13}$ sequences, respectively) were individually incubated with 100 nM 2G12 (Polymun Scientific) in 500 μL of selection buffer at room temperature. 100 μL of 30 mg/mL Dynabeads Protein G magnetic beads (Invitrogen) in selection buffer was added to the mixture and kept suspended by tumbling for 20 min at room temperature to capture complexes. The beads were magnetically isolated and washed with 3×500 μL of selection buffer. To elute the 2G12-binding fusions, the beads were resuspended in 100 μL of selection buffer, heated at 70° C. for 30 min, chilled on ice for 5 min and incubated at room temperature for 10 min with tumbling. The supernatant was recovered and the beads were rinsed with 2×100 μL of selection buffer. These solutions were combined as an eluted fraction.

PCR Amplification of cDNA of Selected Fusions in Round:

The cDNAs of eluted fractions were amplified by PCR using Taq DNA polymerase (Roche) with the forward primer (Library FP1 5'-TAATACGACTCACTATAGGGT-TAACTTTAGTAAGGAGG-3', SEQ ID NO: 22) and the reverse primer (5'-CTAGCTACCTATAGCCGGTGGT-GATGGTGGTGA TGACCCAGAG-3', SEQ ID NO: 23 for the Fixed library); 5'-CTAGCTACCTATAGCCGG TGGT-GATGGTGATGGTGGCCTAAGC-3', SEQ ID NO: 24 for the Variable library). The amplified DNAs were purified by phenol extraction and ethanol precipitation, and used for the transcription of the next selection round.

Modification of the Procedures in Rounds 2-10 and Sequencing.

The fusion preparation and purification procedures were repeated for 10 rounds except for the following changes. In rounds 3-10, the transcripts were purified using MEGAclear kit (Ambion) and crosslinked with XL-PSO. The puromycin-modified RNA was then purified with denaturing PAGE with the visualization of Gel Indicator RNA Staining Solution (Biodynamics Laboratory) and 0.5 μM was used in translation reaction in the presence of $^3$H-histidine. In rounds 2-10, the translation volume was reduced to 0.22-0.52 mL and purifications and following procedures were scaled accordingly. Ni-NTA agarose affinity purification was done only once after oligo(dT) cellulose purification, except in round 2, in which fusions after reverse transcription were re-purified with Ni-NTA agarose and desalted as described above. In round 2 and all subsequent rounds, the click reactions were done only once in the same or similar conditions as described in the "click reaction" section. In the selection parts, the essential differences of the conditions between selection rounds were as summarized in FIG. 5A. In the rounds with Dynabeads Protein A (Invitrogen), bead amounts were twice as much as protein G beads, because the 2G12-capturing capacity of Dynabeads protein A was lower than that of Protein G. In the rounds with 100 mM mannose, binding reactions and the first two wash steps were with mannose, but not in the third wash and elution steps. In rounds 4 and 6, the unglycosylated library was negatively selected for binding to 100 nM 2G12 with protein G magnetic beads in the absence of mannose, to remove glycan-independent binders. In rounds 7-10, the negative selections were done in the presence of 100 mM mannose prior to the positive selections, to remove glycopeptides that bind to protein A or G magnetic bead binders. For sequencing after the selection in rounds 7 and 10, the PCR-amplified DNA was cloned into pCR2.1-TOPO vector (Life Technologies) without colony color selection to avoid unintentional biases.

Nuclease-Digestion of Library Fusions:

To monitor the number of glycans on the peptides in the fusions in every selection round, a part of the cDNA-RNA-glycopeptide fusions (0.05-1 pmol) was removed after the click reaction and desalted by ethanol precipitation in the presence of linear acrylamide carrier (Ambion). The recovered fusions were diluted in 6-7 μL of 200 mM ammonium acetate (pH 5.3) with 1 unit of nuclease P$_1$ (Sigma), and incubated at 37° C. for 1 h to digest nucleic acids. Then, the solutions were neutralized with Tris buffer and analyzed by SDS-PAGE.

Preparation of Individual Peptides and Glycopeptides:

To generate peptides from individual clones, the plasmids were used as templates for PCR with primer sets (library FP1 and 5'-CTAGCTACCTATTTGTCATCGTCGTCTT-TATAATCCCGGTGGTGATGGTGGTGA TGACCCAG-3', SEQ ID NO: 25 for the Fixed library members or CTAGCTACCTATTTG TCATCGTCGTCTTTATAATC-CCGGTGGTGATGGTGATGGTGGCCTAA-3', SEQ ID NO: 26 for the Variable library members) and the PCR products were used for T7 transcription. The resulting mRNAs were purified by denaturing PAGE or MEGAclear kit (Ambion), and 1 µM RNA was used in PURE system translation (reaction volume of translation varied). Typically, 25 µL of translated reaction was diluted with 100 µL of binding buffer (50 mM Tris-HCl, pH 7.8, 300 mM NaCl, 5 mM β-mercaptoethanol) and 25 µL of Ni-NTA agarose suspension (Qiagen), and tumbled at room temperature for 1 h. The resins were transferred to 0.22 µm spin-filter rinsing with 100 µL of bind buffer, and washed with 3×200 µL of bind buffer and 2×200 µL of wash buffer (50 mM Tris-HCl, pH 7.8, 5 mM (3-mercaptoethanol). The bound peptides were eluted with 2×25 µL of 0.1% TFA. The eluted peptides were analyzed by MALDI-TOF MS, using α-Cyano-4-hydroxycinnamic acid matrix (Sigma), with or without desalting with ZipTip $C_{18}$ resin (Millipore). For calibration of MALDI-TOF-MS, at least two of the following standards, bovine insulin, *E. coli* thioredoxin and/or horse apomyoglobin were used. To quantitate peptide yields, the radioactivities were measured by liquid scintillation counting. For the click reaction, the translated and purified peptides were mixed with 0.1% (v/v) Triton X-100, and then dialyzed against $H_2O$ containing 0.1% (v/v) Triton X-100 using Slide-A-Lyzer MINI Dialysis Devices, 3.5K MWCO (Thermo Scientific) overnight to desalt. After dialysis, the peptides were divided into two portions: one was glycosylated via the click reaction, while the other was saved as a non-glycosylated peptide control. The peptides to be glycosylated (typically less than 5 pmol) were evaporated by speedvac in a 0.5 mL microcentrifuge tube for use in click glycosylation. Since the efficiency of the click reaction was not always high with round 10 winners, crude glycosylated peptides were subjected to 2G12 affinity purification to obtain the highest-clicked fraction, as follows. The glycosylated peptide (<4 pmol) was incubated with 100 nM 2G12 in selection buffer (40 µL) at room temp. The solution was then tumbled 30 min with 0.12 mg of equilibrated Dynabeads Protein G to capture 2G12-glycopeptide complex. Beads were then washed with 3×40 µL of selection buffer and resuspended in 10 µL of selection buffer. The resuspended beads were heated at 70° C. for 30 min to denature 2G12 and elute glycopeptides, chilled on ice for 5 min, and tumbled at room temperature for 10 min. The magnetically isolated supernatant was recovered and the beads were rinsed with 10 µL of selection buffer. The supernatant and the rinsed solution were combined as the purified glycopeptide fraction, and the yields were measured by liquid scintillation counting (the recovery of radioactivity was typically in a range of 25-55% of input radioactivity).

SDS-PAGE of Nuclease-Digested Fusions and Glycopeptides:

Unless otherwise noted, SDS-PAGE of nuclease-digested fusions and glycopeptides was done as follows. A 4-20% gradient precast gel (Bio-Rad) was run using a rapid protocol (300 V for 16-20 min). Precision Plus Protein Dual Xtra Standards (Bio-Rad) were used as a molecular weight marker. To visualize the $^{35}S$-labeled peptides by autoradiography, gels were soaked in fixing solution (22.5% acetic acid and 5% ethanol) with shaking for 15 min, dried on filter paper, and exposed to a phosphorimager screen to analyze using Storm Phosphorimager (Amersham). To visualize the $^{35}H$-labeled peptides by fluorography, gels were treated with NAMP100 Amplify Fluorographic Reagent (GE Healthcare) according to the manufacture's protocol, then dried and exposed to X-ray films at −80° C.

Binding Curve and $K_D$ Determination of 2G12-Glycopeptide Interaction:

For round 10 winners, 0.12-0.2 nM radioactive glycopeptides were incubated with 0, 0.25, 0.5, 1, 2, 4, 8, 16, 32 or 64 nM 2G12 in 40 µL of selection buffer at room temperature for 1 h. Then, the solution was added to 0.12 mg of pre-equilibrated Dynabeads Protein G and tumbled at room temperature for 30 min. The supernatant was removed and the beads were washed with 3×40 µL of selection buffer. The radioactivities of the supernatant and wash solutions were measured by liquid scintillation counting as unbound fractions. Since the direct usage of the captured glycopeptides on the beads in liquid scintillation counting partially suppressed the radioactivity detection in the case of $^3H$-label, the bound glycopeptides were eluted and separated from the beads in a following manner. The beads were resuspended in 40 µL of selection buffer, heated at 70° C. for 30 min to elute the bound glycopeptides, chilled on ice for 5 min, and tumbled at room temperature for 10 min. The supernatant was removed, and the beads were washed with 40 µL of selection buffer and resuspended in 40 µL of selection buffer. The radioactivities of these solutions and suspensions were measured by liquid scintillation counting separately and the values were combined as apparent bound fractions. The measured radioactivity of the fraction which bound to the beads without 2G12 (ranging from 0-6% of the total radioactivity in the assay) was subtracted as background from the radioactivity bound to the beads with 2G12, and the difference was divided by the total radioactivity to determine the percentages bound to 2G12. For glycosylated and non-glycosylated 7V8, the same procedure was done except for the following changes: the volume of each solution was reduced to 30 µL, 2 nM radioactive glycopeptide was incubated with 0, 3.125, 6.25, 12.5, 25, 50, or 100 nM 2G12, and 0.18 mg Dynabeads Protein G was used to capture 2G12. All experiments were done at least in triplicate. $K_D$s were calculated as described in the footnote of Table 4 (below).

Analysis of Competition of Glycopeptides and gp120 or Mannose for 2G12-Binding and Non-Glycosylated Peptide Binding to 2G12 of Round 10 Winners:

The procedure was essentially same as described in the previous section with slight modification as follows. The volume of binding reaction was 20-30 µL and other volumes were also adjusted accordingly. 200 nM 2G12 in selection buffer was pre-mixed with or without 400 nM 6×His-tagged gp120(JRFL)(HIV-1) (Immune Technology) or 1 M mannose, and further mixed with the same volume of 0.4 nM radioactive glycopeptides or non-glycosylated peptides for binding reaction. The solutions were incubated at 37° C. for 30 min to equilibrate binding competition and then incubated at room temperature for 30 min to stabilize the complexes. Pre-equilibrated protein G magnetic beads were added to give a final concentration of 6 mg/mL. The separation of unbound fractions and bound fractions was done as described above, except that 0.5 M mannose was added to the washing solution in the case of mannose competition. All experiments were done 3× or more.

Preparation of Synthetic Peptide 10F2 (1):

The unglycosylated peptide 10F2, fXHPYNTSRTSAXX-AALKXQVTDXYALALFHRIL-GSGSGC(StBu)A, SEQ ID NO: 60 where f=formyl and X=homopropargylglycine, was prepared by Fmoc solid-phase peptide synthesis using Pentelute's recent rapid flow-based method (Simon et al., *ChemBioChem Early View DOI*: 10.1002/cbic.201300796 (2014) which is hereby incorporated by reference in its entirety). 76 mg (25 µmol scale) of trityl chemmatrix resin, loaded with 0.33 meq/g alanine by standard procedures (Chan et al., *Fmoc Solid Phase Peptide Synthesis*; Oxford University Press: Oxford, UK (2000), which is hereby incorporated by reference in its entirety), was subjected to 39 cycles of peptide coupling and Fmoc deprotection, with thermal heating to 60° C. (see Table 1 for detailed conditions).

Cysteine and histidine couplings were performed with a lower base concentration to avoid racemization and homopropargylglycine couplings were performed as batch reactions to conserve amino acid. After N-terminal formylation p-nitrophenyl formate, the peptide was cleaved and deprotected using cleavage cocktail B (87.5/5/5/2.5 TFA/water/Phenol/iPr$_3$SiH), and the peptide was triturated four times with cold ether to afford 38 mg of crude solid. 5 mg of this was redissolved in 200 µL DMSO, diluted with 200 µL water, and purified by RP HPLC (Waters Symmetry 300 C4, 5 µm, 10×250 mm, 4 mL/min, 2-42% MeCN in H$_2$O w/0.1% Formic Acid, over 60 min, retention time 52 min) to afford 1.5 mg of product, corresponding to an overall SPPS yield of 11% if the whole batch had been purified. LR ESI-MS: obs. average base peaks 868.79 [M+5H]$^{5+}$, 1085.75 [M+4H]$^{4+}$, 1447.23 [M+3H]$^{3+}$, corresponding to 4338.9 obs. average mass, calc. average mass 4339.9.

After peptide synthesis was complete, the N-terminus was formylated. The swelled resin was transferred to a 15 ml conical tube with a stir bar. 0.25 mmol 4-nitrophenylformate was dissolved in 632 µl DMF (0.33 M final). 125 µL DIPEA (0.86 M final) was added just before addition. Formylation was allowed to occur at 60° C. for 8 minutes while stirring under nitrogen. Next, the supernatant was removed, fresh reagents were added, and formylation was repeated. This was done again for a total of 3-8 minute periods. After the reaction, the resin was washed with DMF 5×10 ml and DCM 3×10 ml.

The peptide was cleaved from the resin with 10 ml of a cleavage cocktail B containing 87.5/5/5/2.5 TFA/phenol/water/TIPS. The resin and cocktail were tumbled at room temperature for 90 minutes. The resin was filtered and washed 3×4 ml DCM. The filtrate was concentrated by rotary evaporation and transferred to a 15 ml conical tube. The peptide was triturated with 5×10 ml cold ether to give 35 mg crude peptide.

4.5 mg of crude peptide was purified by HPLC on a Waters Symmetry300 C4 column (4.6×250 mm, 5 µm particle size) following a 98% A/2% B to 58% A/42% B gradient over 60 minutes with a flow rate of 4 ml/min, where solvent A is water/0.1% formic acid and solvent B is acetonitrile/0.1% formic acid.

Glycosylation of Synthetic Peptide 10F2:

10F2 peptide (0.6 mg, 0.14 µmol, 1 equiv.) and Man$_9$-azide (1.5 mg, 0.97 µmol, 7.0 equiv.) were combined in a 0.5 mL Eppendorf tube by evaporation of stock solutions (tube A). A second tube was prepared, containing 9.8 µL (0.98 µmol, 3.0 equiv.) of a 100 mM solution of THPTA ligand and 9.0 µL (0.90 µmol, 2.8 equiv.) of a 100 mM solution of CuSO$_4$ (tube B), and the tube was evaporated to dryness. Sodium ascorbate (3.0 mg, 15.2 µmol, 47 equiv.) was placed

TABLE 1

Peptide Synthesis Detailed Conditions.

| | Coupling Reagent | AA/Coupling Conc. | mmol AA | Base Conc. | Coupling Flow Rate | Coupling Time |
|---|---|---|---|---|---|---|
| Most AA* | HATU | 0.33M | 1 | 0.95M | 6 ml/min | 30 sec |
| Cys(StBu) | HATU | 0.33M | 0.15 | 0.86M | N/A | 10 min |
| His(Trt) | HATU | 0.33M | 1 | 0.29M | 6 ml/min | 30 sec |
| HPG | HATU | 0.3M | 0.15 | 0.86M | N/A | 10 min |
| Gly | HBTU | 0.33M | 1 | 0.95M | 6 ml/min | |

The general coupling procedure follows Pentelute's procedure (Simon et al., *ChemBioChem Early View* DOI: 10.1002/cbic.201300796 (2014), which is hereby incorporated by reference in its entirety) with modifications. After coupling and after Fmoc deprotection, the resin was washed with 20 ml of DMF at a flow rate of 10 ml/min. Fmoc deprotection was carried out at flow rate of 10 ml/min. Fmoc deprotection solution was 20% piperidine in DMF up until the coupling of aspartic acid, after which a solution of 19% piperidine/1% formic acid in DMF was used to prevent aspartimide formation.

Fmoc-Cys(StBu)-OH and Fmoc-HPG-OH were coupled outside of the reactor. Swelled resin was transferred to a 15 mL conical tube with a stir bar. 0.15 mmol amino acid and 0.15 mmol HATU were dissolved in 425 µL DMF, and 75 µL DIPEA was added just before adding to resin. The coupling reaction was allowed to take place under nitrogen for 10 minutes at 60° C. with stirring. After the reaction, the resin was transferred to the reactor for washing and Fmoc deprotection.

in a third tube (tube C). The three tubes were placed in a 2-neck pear (pointy-bottom) flask, and nitrogen atmosphere was established by cycles of vacuum and nitrogen refill. Under nitrogen efflux, 150 µL DMSO (degassed by freeze-pump-thaw) was added to dissolve the peptide and sugar in tube A, and 75 µL H$_2$O (degassed by freeze-pump-thaw) was added to dissolve the contents of each of tubes B and C. The contents of tube B, and then tube C, were transferred by syringe to tube A. The resulting homogenous mixture was allowed to react under nitrogen atmosphere for 20 hours, at which time UPLC/MS analysis showed nearly complete conversion. The reaction was quenched by addition of TMEDA (1.5 µL, 3.22 µmol, 10 equiv.) and concentrated in vacuo. The residue was purified by RP-HPLC (same column and gradient method as for the unglycosylated 10F2 peptide, retention time 45 min) to afford pure glycopeptide 2. ESI-HRMS: obs. base peaks: 2058.0088 [M+6H]$^{6+}$, 2469.4028 [M+5H]$^{5+}$, 3086.7759 [M+4H]$^{4+}$, deconvoluted mass 12334.962, calc. 12334.980±0.128.

Biotinylation of 10F2 Glycopeptide and Determination of 2G12 Binding by BLI (BioLayer Interferometry):

200 µg 10F2 glycopeptide in 5.5 µL water was treated with 6.5 mL of 50 mM TCEP.HCl/1M Tris-HCl buffer, pH 7.8, under argon, using the same inert gas setup employed in the click procedure. After 4.5 h, the reaction mixture was injected into HPLC (Waters Symmetry, 300 C4, 5 µm, 4.6×250 mm, 1 mL/min, 2-42% over 60 min, retention time 46.8 min).

The 2G12 binding of the resulting biotinylated glycopeptide 3 was determined using a BLItz instrument (Fortebio). Biotin-10F2 was loaded (120 sec) onto a streptavidin biosensor as a 500 nM solution in Buffer 1 (20 mM Tris pH 7.5, 150 mM NaCl, 2 mM $MgSO_4$, 0.20 mg/mL BSA, 0.02% Tween-20). The sensor was washed with Buffer 1 for 60 sec, after which time the net response due to loading was observed as 0.2 nm. The sensor was then equilibrated with Buffer 2 (20 mM Tris pH 7.5, 150 mM NaCl, 2 mM $MgSO_4$, 2.0 mg/mL BSA, 0.1% v/v Tween-20) for 90 sec. 2G12 (prepared in Buffer 2) was associated at several concentrations (0.5, 1, 2, 4, 8, 16, 32 nM, in random order) for 600 sec, followed by dissociation into blank Buffer 2 for 600 sec. After each 2G12 dissociation, the sensor was regenerated to remove remaining 2G12 by treatment with buffer 3 (10 mM glycine-HCl, pH 2.5) for 120 sec, followed by 60 sec of wash with Buffer 1 and further washes to re-equilibrate the tip with Buffer 2. Throughout the experiment, the shake rate was set at 1800 rpm. The use of Buffer 2 (with high BSA) was important during association/dissociation to prevent nonspecific 2G12/streptavidin interactions, while Buffer 1 (low BSA) was required during loading of the glycopeptide to the sensor surface. To further correct for residual nonspecific interactions, the data was referenced to a blank run using 0.5 nM 2G12 on a sensor containing no loaded peptide. The data was fit to a 1:1 binding model, yielding rate constants of $k_{on}=11.1\pm0.4\times10^4$ $M^{-1}$ $s^{-1}$ and $k_{off}=1.51\pm0.02\times10^{-4}$ $s^{-1}$, corresponding to a $K_D$ of 1.37±0.02 nM (Table 2).

TABLE 2

| | | | BLI Curve Fit Parameters | | | | | |
|---|---|---|---|---|---|---|---|---|
| Conc (nM) | $K_D$ (M) | ka $(M^{-1}s^{-1})$ | ka error | kd $(s^{-1})$ | kd error | Rmax | Rmax error | Req |
| 0.5 | 1.368e−9 | 1.106e5 | 3.989e2 | 1.513e−4 | 1.51e−6 | 1.797 | 0.2195 | 0.4810 |
| 1 | 1.368e−9 | 1.106e5 | 3.989e2 | 1.513e−4 | 1.51e−6 | 1.615 | 0.01391 | 0.6817 |
| 2 | 1.368e−9 | 1.106e5 | 3.989e2 | 1.513e−4 | 1.51e−6 | 1.662 | 0.01177 | 0.9866 |
| 4 | 1.368e−9 | 1.106e5 | 3.989e2 | 1.513e−4 | 1.51e−6 | 1.691 | 0.01057 | 1.26 |
| 8 | 1.368e−9 | 1.106e5 | 3.989e2 | 1.513e−4 | 1.51e−6 | 1.601 | 0.008136 | 1.367 |
| 16 | 1.368e−9 | 1.106e5 | 3.989e2 | 1.513e−4 | 1.51e−6 | 1.535 | 0.005597 | 1.414 |
| 32 | 1.368e−9 | 1.106e5 | 3.989e2 | 1.513e−4 | 1.51e−6 | 1.453 | 0.003017 | 1.394 |

Example 1—Fixed and Variable Peptide Library Design for the Directed Evolution of Glycopeptides Two libraries of ~33-mer peptides with glycosylation sites located either in "Fixed" or "Variable" locations were employed. The Fixed library (FIG. 2C, top) contains three potential $Man_9$-glycosylation sites encoded by AUG codons at the "fixed" positions 1, 12, and 33, and each site is followed by 10 random amino acid residues ($X1_0$) encoded by NNN codon, where N is an equimolecular mixture of G, A, U, and C, and in which AUG codon appears in a ratio of 1.6% per position. The Variable library (FIG. 2C, bottom) contains the N-terminal $Man_9$-glycosylation site encoded by the AUG start codon (due to the necessity of the AUG codon for the translation start) followed by 32 random amino acid residues ($X_{32}$). X is encoded by doped N'NS codons, where N' is a mixture of 40% A, 20% G, 20% U and 20% C, S is an equimolecular mixture of G and C, and in which AUG codon appear in a rate of 5% per position.

Example 2—Directed Evolution of Fixed and Variable Peptide Libraries Against HIV Broadly Neutralizing Antibody 2G12

These libraries of ~$10^{13}$ sequences were subjected in parallel to 10 rounds of selection for binding to 2G12. mRNA-displayed-glycopeptides were incubated with successively lower concentrations of 2G12, and bound complexes were retrieved from solution alternately with Protein A or Protein G magnetic beads. Bound fusions were eluted by heating, in which the gp120-binding activity of 2G12 was selectively inactivated without harming the nucleic acid tags (FIGS. 4A-4D).

FIG. 5A shows the percent recovery of the library after each round of selection, as monitored by scintillation counting of radioactive $^{35}$S-cysteine or 3H-histidine. Because the recovery after round 2 was quite high (~10%), the selection stringency was increased by adding 100 mM mannose as a competitor in all subsequent rounds. Glycan-independent binders were removed from the library in rounds 4 and 6 by counter selection of the library prior to the CuAAAC reaction. Counter selections without 2G12 (Protein A or protein G beads only) were used starting at round 7 to remove possible bead binders. Selection rounds 1-7 were performed at room temperature, and rounds 8-10 were performed at 37° C., to remarkable effect (vide infra).

By the end of round 7, library binding to 100 nM 2G12 had grown to a high level. However, an undesired trend toward very high multivalency was also observed throughout these room-temperature selection rounds. This can be seen by SDS-PAGE of the nuclease $P_1$-digested library just prior to each selection round (FIG. 5B, arrows), where separate bands are visible for library species containing different numbers of glycans. This interpretation was confirmed by sequencing of round 7 clones (Table 3 below), which showed that nearly all peptides contained 6-12 glycosylation sites.

TABLE 3

Selected Clones from round 7.

| Library | Clone | Sequence[a] | SEQ ID NO: | Potential Glyco. Sites |
|---|---|---|---|---|
| Fixed | 7F1 | XYYLSVYPSYSXYFSSSYVVWPXPGHRLLIGLE | 27 | 3 |
| | 7F10 | XXEHKLTXLPLXSTDIFLVLLXXFGTTITQVSL | 28 | 6 |
| | 7F6 | XYLPDWXLKSLXLSKWRLPEXFXSPFXLELHXS | 29 | 7 |
| | 7F8 | XLTNITLQXSRXHLLWLHXHDLXXDLCRIXLRS | 30 | 7 |
| | 7F5 | XVLTPTTKXXVXQSPXYFXRSNXLSKXYDYQRL | 31 | 8 |
| | 7F11 | XXIXNSXRIDVXXSNFVHAKSTXVGQRHXGGVG | 32 | 8 |
| | 7F12 | XSXTXQFSHFWXRHXWESXNRWXLARTXDTPID | 33 | 8 |
| | 7F16 | XXCHCLPSHYXXLRFCPXTGSVXDXGLKRXVYH | 34 | 8 |
| | 7F2 | XAKFDEXXAXLNXSRXSSYLXXLXTGRTWPH | 35 | 9 |
| | 7F15 | XTFEXLPRSDSXRXLTXPXXHRXYXIYRGYSNR | 36 | 9 |
| | 7F17 | XSYSXSPRDPNXXIKFLXSRTXXRNPXNVIGSX | 37 | 9 |
| Variable | 7V12 | XHISTNCXPWRYWSIICXXPTWKTVHQXXKTKD | 38 | 6 |
| | 7V6 | XCSRKXACLSRANLXRXRSXXKRRXTXNTSFTX | 39 | 9 |
| | 7V8 | XIRXRTPTSRLXSTXRGXTXNXTSXITPRNDXI | 40 | 9 |
| | 7V10 | XTPFTXAYXTRRKPXXFPIXHRXKSRTPLXXGK | 41 | 9 |
| | 7V3 | XKXNXRIWNPXXNNWSXDTASXLRLXSWXLNXX | 42 | 11 |
| | 7V4 | XTSIXDNTXXLSVNXNRXKINRTLXXXXHXSTX | 43 | 12 |
| | 7V9 | XCXKXYAPNXYDLXPXRXHWXPNVLXPLXSXRX | 44 | 12 |

[a]Only the sequence of the random region (position 1-33) is shown. All peptide sequences used in the 2G12-binding assay were followed by a linker, a His$_6$-tag and a FLAG-tag (GSGSLGHHHHHHRDYKDDDDK, SEQ ID NO: 1) for purification and radiolabeling purposes.

One of these, peptide 7V8 (SEQ ID NO: 40), exhibited a $K_D$ of 17 nM for binding to 2G12 (see Table 4). Although this 2G12 recognition is tighter than that of most reported oligomannose clusters (Ni et al., *Bioconjugate Chem.* 17:493-500 (2006); Joyce et al., *Proc. Natl. Acad. Sci. U.S.A.* 105:15684-15689 (2008); Astronomo et al., *J. Virol.* 82:6359-6368 (2008); Astronomo et al., *Chem. Biol.* 17:357-370 (2010); Luallen et al., *J. Virol.* 82:6447-6457 (2008); Luallen et al., *J. Virol.* 83:4861-4870 (2009); Agrawal-Gamse et al., *J. Virol.* 85:470-480 (2011); Ciobanu et al., *Chem. Commun.* 47:9321-9323 (2011); Marradi et al., *J. Mol. Biol.* 410:798-810 (2011); Li et al., *Org. Biomol. Chem.* 1:3507-3513 (2003); Li et al., *Org. Biomol. Chem.* 2:483-488 (2004); Wang et al., *Chem. Biol.* 11:127-134 (2004); Krauss et al., *J. Am. Chem. Soc.* 129:11042-11044 (2007); Wang et al., *Org. Biomol. Chem.* 5:1529-1540 (2007); Wang et al., *Proc. Natl. Acad. Sci. US A.* 105:3690-3695 (2008); Gorska et al., *Angew. Chem. Int. Ed.* 48:7695-7700 (2009); Doores et al., *Proc. Natl. Acad. Sci. U.S.A.* 107:17107-17112 (2010); and Clark et al., *Chem. Biol.* 19:254-263 (2012), which are hereby incorporated by reference in their entirety). 6-10 glycans is far more than the 3 or 4 gp120 glycans thought to be involved in 2G12 binding (Scanlan et al., *J. Virol.* 76:7306-7321 (2002); Calarese et al., *Science* 300:2065-2071 (2003); and Calarese et al. *Proc. Natl. Acad. Sci. U.S.A.* 102:13372-13377 (2005), which are hereby incorporated by reference in their entirety). Moreover, none of the sequences obtained were replicates, indicating that the library had not yet converged to the best possible sequences. For this reason, selection was continued for additional rounds.

Given the high multivalency concerns, subsequent selection rounds were carried out at 37° C. because of a striking temperature effect observed in related studies with SELMA selection of glycosylated DNA libraries (Temme et al., *J. Am. Chem. Soc.* 136:1726-1729 (2014), which is hereby incorporated by reference in its entirety). In that work, increasing the temperature of the 2G12 selection step to 37° C. was found to dramatically favor sequences with lower multivalency and much stronger binding. After applying this modification to the next three rounds of glycopeptide selection, a parallel trend in the results was observed: low-valent binders—barely visible in the whole-library gel at the beginning of round 8—completely took over both libraries (FIG. 5B, boxes).

The selected round 10 glycopeptides are listed in Table 4, along with their measured binding affinity for 2G12.

TABLE 4

Binding Constants of Selected- and non-Selected Glycopeptides.

| Library (round obtained) | Clone | Sequence[a] | SEQ ID NO: | Poten. Glyco. Sites | $K_D$ [nM][b] | $F_{max}$ [%][c] |
|---|---|---|---|---|---|---|
| Fixed (before 1) | 6E | XQTACPSPAFLXLSRSAHYFHAXHPTSAAPDIS | 45 | 3 | >128 | ND[d] |
| Variable (before 1) | 12G | XYKNIPSTTXNLYSKPXATVTTLKCKLNGNRIS | 46 | 3 | >128 | ND[d] |
| Variable (7) | 7V8 | XIRXRTPTSRLXSTXRGXTXNXTSXITPRNDXI | 40 | 9 | 17 ± 5.6 | 108 ± 12 |

TABLE 4-continued

Binding Constants of Selected- and non-Selected Glycopeptides.

| Library (round obtained) | Clone | Sequence[a] | SEQ ID NO: | Poten. Glyco. Sites | $K_D$ [nM][b] | $F_{max}$ [%][c] |
|---|---|---|---|---|---|---|
| Fixed (10) | 10F6 | XLXFIRIYPTRXQVVYHAPLLTXVRXSPTGPLI | 15 | 5 | 0.54 ± 0.043 | 87 ± 1.3 |
|  | 10F2 | XHPYNTSRTSAXXAALKXQVTDXYALALFHRIL | 13 | 5 | 0.60 ± 0.045 | 86 ± 1.2 |
|  | 10F12 | XCYVTVIPAXNXPEARLGIVCHXPGIRRGKALY | 16 | 4 | 0.77 ± 0.084 | 90 ± 2.0 |
|  | 10F5 | XSPHLPVLLCKXVLNDGRRIVQXSCELPXVRRS | 14 | 4 | 0.97 ± 0.13 | 93 ± 2.7 |
|  | 10F8 | XLLKXVDQSRLXPVPGIGVTLHXRSIPYSYLPI | 4 | 4 | 2.6 ± 0.23 | 97 ± 2.2 |
|  | 10F3 | XDTLHLKQIGGXPNCITQQDVRXTSIPYTYTWP | 3 | 3 | 3.0 ± 0.31 | 100 ± 2.7 |
|  | 10F9 | XRSTLNSLEYRXQYATEDPRIRXASIPYTYWWP | 5 | 3 | 3.1 ± 0.17 | 86 ± 1.2 |
| Variable (10) | 10V1 | XATKTNCKREKTXDNHVTIXRSIPWYTYRWLPN | 6 | 3 | 1.9 ± 0.17 | 97 ± 2.1 |
|  | 10V9 | XTSIPYTYLNRSLWTNYRVNSWSXSKNVNVXPL | 11 | 3 | 3.9 ± 0.11 | 85 ± 0.68 |
|  | 10V8 | XVLPTIISTNVNPFRXLSIPTYTYLXPITWGEI | 10 | 3 | 4.6 ± 0.34 | 94 ± 2.0 |

[a]Only the sequence of the random region (position 1-33) is shown. All peptide sequences used in the 2G12-binding assay were preceded by an N-terminal formyl group and followed by a linker, a His6-tag and a FLAG-tag (GSGSLGHHHHHHRDYKDDDDK, SEQ ID NO: 1) for purification and radiolabeling purposes. "X" denotes potential Man9-glycosylation sites encoded by the AUG codon.
[b,c]In the assay, the peptides were radiolabeled with either $^{35}$S-cysteine or $^{3}$H-histidine as described above, and incubated with various concentrations of 2G12, and 2G12-peptide complexes were isolated with magnetic protein G beads. Percentages of the fractions bound were calculated from radioactivity measured by liquid scintillation counting as described above. $K_D$ and $F_{max}$ were calculated by fitting $F_{bound} = (F_{max} [2G12])/(K_D + [2G12])$ to average data points. Errors reported are the standard error of the curve fit.
[d]Not Determined.

Example 3—Identification of a Peptide Consensus Motif in Fixed and Variable Round-10 Selected Glycopeptides Sequencing of 24 clones from each library (Tables 4, 5) confirmed the low number of glycosylations (2 to 5) and revealed a high degree of sequence convergence.

TABLE 5

Selected Clones from Round 10.

| Library | Clone | Sequences[a] | SEQ ID NO: | Potential Glyco. Sites | No. clones (in 24) |
|---|---|---|---|---|---|
| Fixed | 10F5 | XSPHLPVLLCKXVLNDGRRIVQXSCELPXVRRS | 14 | 4 | 4/24 |
|  | 10F2 | XHPYNTSRTSAXXAALKXQVTDXYALALFHRIL | 13 | 5 | 3/24 |
|  | 10F12 | XCYVTVIPAXNXPEARLGIVCHXPGIRRGKALY | 16 | 4 | 2/24 |
|  | 10F6 | XLXFIRIYPTRXQVVYHAPLLTXVRXSPTGPLI | 15 | 5 | 1/24 |
|  | 10F16 | XVRSAAVDTSPXTSSSQNAILLXFSYDVCLFDL | 47 | 3 | 1/24 |
|  | 10F20 | XIALTSNCYLNXGPRIFRYDVGLTQLCQGRRRS | 48 | 2 | 1/24 |
|  | 10F3 | XDTLHLKQIGGXPNCITQQDVRXTSIPYTYTWP | 3 | 3 | 4/24 |
|  | 10F23 | XDTLHLKQIGVXPNCITQQDVRXTSIPYTYTWP | 49 | 3 | 1/24 |
|  | 10F8 | XLLKXVDQSRLXPVPGIGVTLHXRSIPYTYSYLPI | 4 | 4 | 4/24 |
|  | 10F9 | XRSTLNSLEYRXQYATEDPRIRXASIPYTYWWP | 5 | 3 | 2/24 |
|  | 10F18 | XFSTANIYGAPXNTDXRLEHRQXKSIPYTYYWS | 50 | 4 | 1/24 |
|  | 10F24 | XERPSLXCGLSXLTSGGTQSSVXRSIPFYTYWW | 12 | 4 | 1/24 |
| Var. | 10V1 | XATKTNCKREKTXDNHVTIXRSIPWYTYRWLPN | 6 | 3 | 14/24 |
|  | 10V14 | XATKTNCKREKTIDNHVTIXRSIPWYTYRWLPN | 51 | 2 | 2/24 |
|  | 10V2 | XATKTNFKREKTXDNHVTIXRSIPWYTYRWLPN | 7 | 3 | 1/24 |
|  | 10V6 | XATRTNCKREKTXDNHVTIXRSIPWYTYRWLPN | 8 | 3 | 1/24 |
|  | 10V11 | XATKTSCKREKTXDNHVTIXRSIPWYTYRWLPN | 9 | 3 | 1/24 |
|  | 10V9 | XTSIPYTYLNRSLWTNYRVNSWSXSKNVNVXPL | 11 | 3 | 4/24 |
|  | 10V8 | XVLPTIISTNVNPFRXLSIPTYTYLXPITWGEI | 10 | 3 | 1/24 |

[a]Consensus sequences are in bold. 10F23, 10V14, 10V2, 10V6 and 10V11 contain a mutated amino acid from their potential parent sequences, 10F3 and 10V1, respectively.

Many repeat sequences were observed, as was a peptide consensus motif, X̲xSIP(-/x)YTY(L/xW)(-/x)P, where X̲ denotes Man9-HPG and x denotes a variable amino acid. This motif was present in some clones from both libraries, and apparently arose from convergent evolution in multiple sequence families, as it is located sometimes early, sometimes late in the sequences. 10 glycopeptides were prepared without mRNA tags by in vitro translation without the puromycin linker (FIGS. 6A-6B), and Kg's were determined by incubation of the glycopeptide with various concentrations of 2G12, followed by capture on protein G beads and quantification of radioactivity. All 10 of the tested glycopeptides were recognized tightly by 2G12, with $K_D$'s in the range of 0.5-5 nM, similar to the strength of 2G12-gp120 interaction (Table 4 and FIG. 7) (2G12-gp120 $K_D$=5.8 nM) (Hoorelbeke et al., *J. FEBS Lett.* 587:860-866 (2013), which is hereby incorporated by reference in its entirety). Some of these peptides lacked the peptide consensus motif, and all were dependent on glycosylation for 2G12 binding (FIG. 8A), indicating that the glycans are the major element recognized by the antibody. This was further confirmed by studies showing a significant reduction in binding when either 0.5M mannose. Moreover a reduction in binding observed with 200-800 nM recombinant gp120 (FIGS. 8A-B) added to the assay shows that the selected glycopeptides compete with gp120 for binding its site on 2G12. In contrast to round 10 selected peptides, clones picked from the libraries prior to selection showed very little binding to 2G12 at concentrations up to 128 nM (Table 4, FIGS. 9A-C), indicating that not all peptide backbones are suitable for highly antigenic presentation of the carbohydrates.

Example 4—Confirmation of 2G12 Binding Affinity to Round-10 Selected Glycopeptides Using BioLayer Interferometry To confirm that the results presented in Table 4 were not artifacts of ribosomal translation, glycopeptide 10F2 was chemically synthesized and characterized. The 2G12 binding affinity of glycopeptide 10F2 was confirmed using an alternate assay, BioLayer Interferometry, ("BLI") (Abdiche et al., *J. Anal. Biochem.* 377:209-217 (2008), which is hereby incorporated by reference in its entirety). Pentelute's new Rapid Flow Solid Phase Peptide Synthesis method (Simon et al., *ChemBioChem Early View* DOI: 10.1002/cbic.201300796 (2014), which is hereby incorporated by reference in its entirety) in which activated amino acids are flowed through a thermally-heated reactor containing peptide synthesis resin, was used to prepare the 10F2 peptide. In this manner alkyne-containing peptide 1, in which the C-terminal His6 tag of the ribosomal peptide was replaced by an -StBu-protected cysteine, was obtained (FIG. 10A). CuAAAC glycosylation proceeded to near completion and HPLC purification afforded the desired glycopeptide 2, whose identity was confirmed by mass spectrometry. Reductive deprotection of the cysteine and immediate trapping with a maleimide-biotin reagent, appended the biotin necessary for immobilization to the streptavidin biosensor surface used in the BLI assay. After immobilization of the biotinylated glycopeptide 3 on the sensor, 2G12 was associated to the surface at several concentrations, followed by dissociation in blank buffer (FIG. 10B). The resulting response curves were fit globally to a 1:1 binding model and afforded rate constants of $k_{on}$=11.1±0.4×10$^4$ M$^{-1}$s$^{-1}$ and $k_{off}$=1.51±0.02×10$^{-4}$ s$^{-1}$, corresponding to a $K_D$ of 1.37±0.02 nM. This affinity measurement is in reasonable agreement with the measurement of ribosomally-translated 10F2 in the bead-based assay. Moreover, this interaction is both kinetically and thermodynamically comparable to that measured for the 2G12-gp120 interaction ($k_{on}$=6.6×10$^4$ M$^{-1}$s$^{-1}$, $k_{off}$=3.8×10$^{-4}$ s$^{-1}$, $K_D$=5.8 nM) (Hoorelbeke et al., *J. FEBS Lett.* 587:860-866 (2013), which is hereby incorporated by reference in its entirety).

The 2G12 recognition observed for the Man$_9$ glycopeptides obtained in the preceding Examples represents an enhancement of up to 360,000-fold compared with monovalent Man$_9$ glycan ($K_D$=180 μM) (Wang et al., *Proc. Natl. Acad. Sci. U.S.A.* 105:3690-3695 (2008), which is hereby incorporated by reference in its entirety). Although Wang has prepared Man$_9$ dendrimers which bind 2G12 with $K_D$'s down to 3.1 nM, that level of binding was achieved only with 9- and 27-mers, whereas 610 nM binding was observed with trivalent Man$_9$ dendrimers. Taken together, these data indicate that the clustering and/or support of Man$_9$ by neighboring elements in the glycopeptides obtained in the preceding Examples results in better mimicry of the 2G12 epitope than previous Man$_9$ presentations. These evolved glycoclusters are extremely interesting candidates for in vivo immunogenicity studies.

Discussion of Examples 1-4

The preceding Examples demonstrate the in vitro selection of multivalent glycopeptides from diverse libraries (10$^{13}$ sequences). It has been shown that the use of higher temperature in the target binding step of selection favors glycopeptides with lower multivalency, an effect which parallels that which was observed in the SELMA selection of glycosylated DNAs (MacPherson et al., *Angew. Chem. Int. Ed.* 50:11238-11242 (2011); Temme et al., *Chem. Eur. J.* 19:17291-17295 (2013); and Temme et al., *J. Am. Chem. Soc.* 136:1726-1729 (2014), which are hereby incorporated by reference in their entirety). This approach can be used to design multivalent carbohydrate vaccines targeting additional HIV or cancer epitopes, as well as multivalent carbohydrate ligands for other lectins. The glycopeptides and other conjugates thus obtained will be useful tools in biological studies and for therapeutic applications.

Example 5—Mutational Analysis of 2G12-Binding Clones

One or more point mutations or truncations were introduced into several of the clones to assess their effects on 2G12 binding. The mutated sequences, generated according to the procedures described in the preceding Material & Methods section, are shown in Table 6 below.

TABLE 6

Results of Mutational Analysis

| Name | Sequence[a] | SEQ ID NO: | $K_D$ [nM][b] | $F_{max}$ [%][c] |
|---|---|---|---|---|
| 10F5-C10,25S | X̲SPHLPVLLSKX̲VLNDGRRWQX̲SSELPX̲VRRS | 52 | 2.5 nM + 0.5 | 94 |
| 10V1-C7S[d] | X̲ATKTNSKREKTX̲DNHVTIX̲RSIPWYTYRWLPN | 53 | 5.6 nM + 0.5 | NA[d] |

TABLE 6-continued

Results of Mutational Analysis

| Name | Sequence[a] | SEQ ID NO: | $K_D$ [nM][b] | $F_{max}$ [%][c] |
|---|---|---|---|---|
| 10V1-C7A[d] | XATKTNAKREKTXDNHVTIXRSIPWYTYRWLPN | 54 | 4.4 nM + 0.3 | NA[d] |
| 10V1-Δ9 | XRSIPWYTYRWLPN | 55 | ~7.5 nM + 3.4 | 20 |
| 10F2-Δ11 | XXAALKXQVTDXYALALFHRIL | 56 | 0.89 nM + 0.12 | 70 |
| 10F3-Δ11 | XPNCITQQDVRXTSIPYTYTWP | 57 | 25 nM + 4.4 | 32 |
| 10F5-Δ11 | XVLNDGRRIVQXSCELPXVRRS | 58 | >200 nM | 17 |
| 10F12-C2,21S | XSYVTVIPAXNXPEARLGWSHXPGIRRGKALY | 59 | 186 nM + 102 | 90 |
| 10F3 -C15S | XDTLHLKQIGGXPNSITQQDVRXTSIPYTYTWP | 62 | 2.91 nM + 0.18 | 63 |

[a] All peptide sequences used in the 2G12-binding assay were preceded by an N-terminal formyl group and followed by a linker, a His6-tag and a FLAG-tag (GSGSLGHHHHHHRDYKDDDDK, SEQ ID NO: 1) for purification and radiolabeling purposes. "X" denotes potential Man9-glycosylation sites encoded by the AUG codon.
[b,c] In the assay, the peptides were radiolabeled with either $^{35}$S-cysteine or $^{3}$H-histidine as noted above, and incubated with various concentrations of 2G12, and 2G12-peptide complexes were isolated with magnetic protein G beads. Percentages of the fractions bound were calculated from radioactivity measured by liquid scintillation counting as described above. $K_D$ and $F_{max}$ were calculated by fitting $F_{bound} = (F_{max} [2G12])/(K_D + [2G12])$ to average data points. Errors reported are the standard error of the curve fit.
[d] 10V1-C7s and 10V1-C7A sequences were evaluated by a biolayer interferometry (BLI) assay, rather than the radioactive binding assay, and the material used was prepared synthetically rather than by ribosomal translation.

Based on these results, Cys residues can be mutated to Ser or Ala when the Cys residue is not involved in disulfide bond formation with a second Cys residue. Thus, Cys substitution is sequence dependent. This is confirmed by 10F12 as compared to 10F5 and 10F3, where Cys substitutions were tolerated in the latter but not the former.

Truncation is also feasible where the truncation either does not involve residues involved in forming the glycosylated epitope recognized by 2G12 or residues involved in stabilizing the structure of the glycopolypeptide. This is confirmed by 10F2-A11 and 10V1-A19, which still exhibit tight binding to 2G12.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for selecting a glycopolypeptide that binds to a target protein comprising:
   providing a pool of glycopolypeptides fused via puromycin linker to an encoding mRNA-cDNA duplex;
   combining the pool with a target protein to form a mixture;
   incubating the mixture for a period of time sufficient to allow any target protein to bind to one or more of the glycopolypeptides, thereby forming glycopolypeptide-target protein complexes; and
   isolating from the mixture the glycopolypeptide-target protein complexes, thereby identifying a plurality of selected glycopolypeptides.

2. The method according to claim 1, wherein the provided pool comprises greater than $10^{10}$ glycopolypeptides fused via puromycin linker to an encoding mRNA-cDNA duplex.

3. The method according to claim 1, wherein said incubating is carried out at a temperature of about 18 to 27° C.

4. The method according to claim 1, wherein said incubating is carried out at a temperature of greater than 27° C.

5. The method according to claim 1, wherein said isolating comprises:
   exposing the mixture to magnetic beads labeled with an affinity reagent that binds to a portion of the target protein; and
   recovering magnetic beads bound to glycopolypeptide-target protein complexes.

6. The method according to claim 1, further comprising:
   amplifying cDNA from the plurality of selected glycopolypeptides fused via puromycin linker to an encoding mRNA-cDNA duplex, thereby forming a plurality of DNA duplexes; and
   regenerating a second pool of glycopolypeptides fused via puromycin linker to an encoding mRNA-cDNA duplex using the DNA duplexes.

7. The method according to claim 6, wherein said regenerating comprises:
   transcribing mRNA using the DNA duplexes as templates;
   attaching a puromycin linker to the 3' region of the mRNA strand;
   translating the mRNA strand using one or more modified amino acids comprising a reactive side chain, whereby the translated polypeptide remains fused to the mRNA strand via the puromycin linker;
   attaching one or more monosaccharides or oligosaccharides to the translated polypeptide via the reactive side chain; and
   reverse transcribing a cDNA strand using the mRNA strand to form an mRNA-cDNA duplex, and thereby forming the second pool.

8. The method according to claim 7, wherein said translating further comprises:
   fusing of the translated polypeptide to the mRNA strand via the puromycin linker.

9. The method according to claim 8, wherein said fusing comprises:
   exposing the mixture to KCl and $Mg(OAc)_2$ for a period of time and
   subsequent to said exposing, maintaining the mixture to a temperature below 0° C. for a second period of time.

10. The method according to claim 7, wherein one of the modified amino acids and the oligosaccharide comprise an azide group or a thiol group, and the other of the modified amino acids and the oligosaccharide comprises an alkynyl group or alkenyl group.

11. The method according to claim 7, wherein the modified amino acid is homopropargylglycine.

12. The method according to claim 7, wherein the reaction conditions for said attaching includes copper catalysis or ruthenium catalysis or strain-promoted alkyne-azide cycloaddition.

13. The method according to claim 1, further comprising repeating said combining using the second pool, said incubating, and said isolating to identify a second plurality of selected glycopolypeptides.

14. The method according to claim 13, wherein said incubating is carried out for the second pool using different conditions than said incubating for the first pool.

15. The method according to claim 14, wherein said conditions comprise one or more of target protein concentration, temperature, duration, introduction of competitor molecules, and increasing the number or condition of wash steps.

16. The method according to claim 13, wherein said repeating comprises:
   performing a negative selection step to remove polypeptides which bind to target protein without being glycosylated, or to remove polypeptides or glycopolypeptides that bind directly to a solid support.

17. The method according to claim 1, wherein the target protein is an antibody.

18. The method according to claim 17, wherein the antibody is (i) a carbohydrate-binding neutralizing monoclonal antibody that binds specifically to N-glycosylated HIV gp120, N-glycosylated HIV gp41, a combination of N-glycosylated HIV gp120 and gp41, or N-glycosylated HSV-2 gD, or (ii) a carbohydrate-binding cytotoxic monoclonal antibody that binds specifically to O-glycosylated cancer-specific human podoplanin, aberrantly O-glycosylated cancer-specific MUC1, aberrantly O-glycosylated cancer-specific Integrin α3β1, or N-glycosylated cancer-specific antigen RAAG12.

19. The method according to claim 18, wherein the carbohydrate-binding, neutralizing monoclonal antibody is 2G12, PG9, PG16, PGT121, PGT122, PGT123, PGT125, PGT126, PGT127, PGT128, PGT129, PGT130, PGT131, PGT135, PGT136, PGT137, PGT141, PGT142, PGT143, PGT144, PGT145, PGT151, PGT152, PGT153, PGT154, PGT155, PGT156, PGT157, PGT158, CH01, CH02, CH03, CH04, 10-1074, 10-996, 10-1146, 10-847, 10-1341, 10-1121, 10-1130, 10-410, 10-303, 10-259, 10-1369, or E317.

20. The method according to claim 18, wherein the carbohydrate-binding cytotoxic monoclonal antibody is LpMab-2, 237 MAb, RAV12, BCMab1, DF3, 115D8, or GOD3-2C4.

* * * * *

SEQUENCE LISTING

```
<160> NUMBER OF SEQ ID NOS: 62

<210> SEQ ID NO 1
<211> LENGTH: 21
<212> TYPE: PRT
<213> ORGANISM: artificial
<220> FEATURE:
<223> OTHER INFORMATION: Flexible Linker - His6 tag-FLAG tag

<400> SEQUENCE: 1

Gly Ser Gly Ser Leu Gly His His His His His His Arg Asp Tyr Lys
1               5                   10                  15

Asp Asp Asp Asp Lys
            20

<210> SEQ ID NO 2
<211> LENGTH: 9
<212> TYPE: PRT
<213> ORGANISM: artificial
<220> FEATURE:
<223> OTHER INFORMATION: 2G12-Binding Glycopeptide Consensus Sequence
<220> FEATURE:
```

-continued

```
<221> NAME/KEY: MISC_FEATURE
<222> LOCATION: (1)..(1)
<223> OTHER INFORMATION: Xaa is a glycosylated homopropargylglycine
<220> FEATURE:
<221> NAME/KEY: MISC_FEATURE
<222> LOCATION: (2)..(2)
<223> OTHER INFORMATION: Xaa is optional and can be any amino acid
<220> FEATURE:
<221> NAME/KEY: MISC_FEATURE
<222> LOCATION: (6)..(6)
<223> OTHER INFORMATION: Xaa is optional and can be any amino acid

<400> SEQUENCE: 2

Xaa Xaa Ser Ile Pro Xaa Tyr Thr Tyr
1               5

<210> SEQ ID NO 3
<211> LENGTH: 33
<212> TYPE: PRT
<213> ORGANISM: artificial
<220> FEATURE:
<223> OTHER INFORMATION: Clone 10F3
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 3

Xaa Asp Thr Leu His Leu Lys Gln Ile Gly Gly Xaa Pro Asn Cys Ile
1               5                   10                  15

Thr Gln Gln Asp Val Arg Xaa Thr Ser Ile Pro Tyr Thr Tyr Thr Trp
            20                  25                  30

Pro

<210> SEQ ID NO 4
<211> LENGTH: 33
<212> TYPE: PRT
<213> ORGANISM: artificial
<220> FEATURE:
<223> OTHER INFORMATION: Clone 10F8
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 4
```

```
Xaa Leu Leu Lys Xaa Val Asp Gln Ser Arg Leu Xaa Pro Val Pro Gly
1               5                   10                  15

Ile Gly Val Thr Leu His Xaa Arg Ser Ile Pro Tyr Ser Tyr Leu Pro
            20                  25                  30

Ile
```

<210> SEQ ID NO 5
<211> LENGTH: 33
<212> TYPE: PRT
<213> ORGANISM: artificial
<220> FEATURE:
<223> OTHER INFORMATION: Clone 10F9
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 5

```
Xaa Arg Ser Thr Leu Asn Ser Leu Glu Tyr Arg Xaa Gln Tyr Ala Thr
1               5                   10                  15

Glu Asp Pro Arg Ile Arg Xaa Ala Ser Ile Pro Tyr Thr Tyr Trp Trp
            20                  25                  30

Pro
```

<210> SEQ ID NO 6
<211> LENGTH: 33
<212> TYPE: PRT
<213> ORGANISM: artificial
<220> FEATURE:
<223> OTHER INFORMATION: Clone 10V1
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
      homopropargylglycine or homopropargylglycine

<400> SEQUENCE: 6

```
Xaa Ala Thr Lys Thr Asn Cys Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn
```

<210> SEQ ID NO 7
<211> LENGTH: 33
<212> TYPE: PRT

```
<213> ORGANISM: artificial
<220> FEATURE:
<223> OTHER INFORMATION: Clone 10V2
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
      homopropargylglycine or homopropargylglycine

<400> SEQUENCE: 7

Xaa Ala Thr Lys Thr Asn Phe Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn

<210> SEQ ID NO 8
<211> LENGTH: 33
<212> TYPE: PRT
<213> ORGANISM: artificial
<220> FEATURE:
<223> OTHER INFORMATION: Clone 10V6
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
      homopropargylglycine or homopropargylglycine

<400> SEQUENCE: 8

Xaa Ala Thr Arg Thr Asn Cys Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn

<210> SEQ ID NO 9
<211> LENGTH: 33
<212> TYPE: PRT
<213> ORGANISM: artificial
<220> FEATURE:
<223> OTHER INFORMATION: Clone 10V11
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
      homopropargylglycine or homopropargylglycine
```

```
<220> FEATURE:
<221> NAME/KEY: MISC_FEATURE
<222> LOCATION: (20)..(20)
<223> OTHER INFORMATION: Xaa is a glycosylated derivative of
      homopropargylglycine or homopropargylglycine

<400> SEQUENCE: 9

Xaa Ala Thr Lys Thr Ser Cys Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn

<210> SEQ ID NO 10
<211> LENGTH: 33
<212> TYPE: PRT
<213> ORGANISM: artificial
<220> FEATURE:
<223> OTHER INFORMATION: Clone 10V8
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (16)..(16)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (26)..(26)
<223> OTHER INFORMATION: Xaa is a glycosylated derivative of
      homopropargylglycine or homopropargylglycine

<400> SEQUENCE: 10

Xaa Val Leu Pro Thr Ile Ile Ser Thr Asn Val Asn Pro Phe Arg Xaa
1               5                   10                  15

Leu Ser Ile Pro Thr Tyr Thr Tyr Leu Xaa Pro Ile Thr Trp Gly Glu
            20                  25                  30

Ile

<210> SEQ ID NO 11
<211> LENGTH: 33
<212> TYPE: PRT
<213> ORGANISM: artificial
<220> FEATURE:
<223> OTHER INFORMATION: Clone 10V9
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (24)..(24)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (31)..(31)
<223> OTHER INFORMATION: Xaa is a glycosylated derivative of
      homopropargylglycine or homopropargylglycine

<400> SEQUENCE: 11

Xaa Thr Ser Ile Pro Tyr Thr Tyr Leu Asn Arg Ser Leu Trp Thr Asn
1               5                   10                  15

Tyr Arg Val Asn Ser Trp Ser Xaa Ser Lys Asn Val Asn Val Xaa Pro
            20                  25                  30
```

Leu

<210> SEQ ID NO 12
<211> LENGTH: 33
<212> TYPE: PRT
<213> ORGANISM: artificial
<220> FEATURE:
<223> OTHER INFORMATION: Clone 10F24
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (7)..(7)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 12

Xaa Glu Arg Pro Ser Leu Xaa Cys Gly Leu Ser Xaa Leu Thr Ser Gly
1               5                   10                  15

Gly Thr Gln Ser Ser Val Xaa Arg Ser Ile Pro Phe Tyr Thr Tyr Trp
            20                  25                  30

Trp

<210> SEQ ID NO 13
<211> LENGTH: 33
<212> TYPE: PRT
<213> ORGANISM: artificial
<220> FEATURE:
<223> OTHER INFORMATION: Clone 10F2
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (18)..(18)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 13

Xaa His Pro Tyr Asn Thr Ser Arg Thr Ser Ala Xaa Xaa Ala Ala Leu
1               5                   10                  15

Lys Xaa Gln Val Thr Asp Xaa Tyr Ala Leu Ala Leu Phe His Arg Ile
            20                  25                  30

Leu

```
<210> SEQ ID NO 14
<211> LENGTH: 33
<212> TYPE: PRT
<213> ORGANISM: artificial
<220> FEATURE:
<223> OTHER INFORMATION: Clone 10F5
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (29)..(29)
<223> OTHER INFORMATION: Xaa is a glycosylated derivative of
      homopropargylglycine or homopropargylglycine

<400> SEQUENCE: 14

Xaa Ser Pro His Leu Pro Val Leu Leu Cys Lys Xaa Val Leu Asn Asp
1               5                   10                  15

Gly Arg Arg Ile Val Gln Xaa Ser Cys Glu Leu Pro Xaa Val Arg Arg
            20                  25                  30

Ser

<210> SEQ ID NO 15
<211> LENGTH: 33
<212> TYPE: PRT
<213> ORGANISM: artificial
<220> FEATURE:
<223> OTHER INFORMATION: Clone 10F6
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (3)..(3)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (26)..(26)
<223> OTHER INFORMATION: Xaa is a glycosylated derivative of
      homopropargylglycine or homopropargylglycine

<400> SEQUENCE: 15

Xaa Leu Xaa Phe Ile Arg Ile Tyr Pro Thr Arg Xaa Gln Tyr Val Tyr
1               5                   10                  15

His Ala Pro Leu Leu Thr Xaa Val Arg Xaa Ser Pro Thr Gly Pro Leu
            20                  25                  30
```

Ile

```
<210> SEQ ID NO 16
<211> LENGTH: 33
<212> TYPE: PRT
<213> ORGANISM: artificial
<220> FEATURE:
<223> OTHER INFORMATION: Clone 10F12
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (10)..(10)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 16

Xaa Cys Tyr Val Thr Val Ile Pro Ala Xaa Asn Xaa Pro Glu Ala Arg
1               5                   10                  15

Leu Gly Ile Val Cys His Xaa Pro Gly Ile Arg Arg Gly Lys Ala Leu
            20                  25                  30

Tyr

<210> SEQ ID NO 17
<211> LENGTH: 198
<212> TYPE: DNA
<213> ORGANISM: artificial
<220> FEATURE:
<223> OTHER INFORMATION: Antisense strands of synthetic fixed library
      DNA
<220> FEATURE:
<221> NAME/KEY: misc_feature
<222> LOCATION: (54)..(83)
<223> OTHER INFORMATION: N can be A, T, C, or G
<220> FEATURE:
<221> NAME/KEY: misc_feature
<222> LOCATION: (87)..(116)
<223> OTHER INFORMATION: N can be A, T, C, or G
<220> FEATURE:
<221> NAME/KEY: misc_feature
<222> LOCATION: (120)..(149)
<223> OTHER INFORMATION: N can be A, T, C, or G

<400> SEQUENCE: 17
ctagctacct atagccggtg gtgatggtgg tgatgaccca gagaaccgga gccnnnnnnn      60
nnnnnnnnnn nnnnnnnnnn nnncatnnnn nnnnnnnnnn nnnnnnnnnn nnnnnncatn    120
nnnnnnnnnn nnnnnnnnnn nnnnnnnnnc atttagctgt cctccttact aaagttaacc    180
ctatagtgag tcgtatta                                                  198

<210> SEQ ID NO 18
<211> LENGTH: 198
<212> TYPE: DNA
<213> ORGANISM: Artificial
<220> FEATURE:
<223> OTHER INFORMATION: Antisense strand of variable library DNA
<220> FEATURE:
```

```
<221> NAME/KEY: misc_feature
<222> LOCATION: (55)..(55)
<223> OTHER INFORMATION: N can be A, T, C, or G
<220> FEATURE:
<221> NAME/KEY: misc_feature
<222> LOCATION: (56)..(56)
<223> OTHER INFORMATION: N is T, A, G, or C at a ratio of 40:20:20:20
<220> FEATURE:
<221> NAME/KEY: misc_feature
<222> LOCATION: (58)..(58)
<223> OTHER INFORMATION: N can be A, T, C, or G
<220> FEATURE:
<221> NAME/KEY: misc_feature
<222> LOCATION: (59)..(59)
<223> OTHER INFORMATION: N is T, A, G, or C at a ratio of 40:20:20:20
<220> FEATURE:
<221> NAME/KEY: misc_feature
<222> LOCATION: (61)..(61)
<223> OTHER INFORMATION: N can be A, T, C, or G
<220> FEATURE:
<221> NAME/KEY: misc_feature
<222> LOCATION: (62)..(62)
<223> OTHER INFORMATION: N is T, A, G, or C at a ratio of 40:20:20:20
<220> FEATURE:
<221> NAME/KEY: misc_feature
<222> LOCATION: (64)..(64)
<223> OTHER INFORMATION: N can be A, T, C, or G
<220> FEATURE:
<221> NAME/KEY: misc_feature
<222> LOCATION: (65)..(65)
<223> OTHER INFORMATION: N is T, A, G, or C at a ratio of 40:20:20:20
<220> FEATURE:
<221> NAME/KEY: misc_feature
<222> LOCATION: (67)..(67)
<223> OTHER INFORMATION: N can be A, T, C, or G
<220> FEATURE:
<221> NAME/KEY: misc_feature
<222> LOCATION: (68)..(68)
<223> OTHER INFORMATION: N is T, A, G, or C at a ratio of 40:20:20:20
<220> FEATURE:
<221> NAME/KEY: misc_feature
<222> LOCATION: (70)..(70)
<223> OTHER INFORMATION: N can be A, T, C, or G
<220> FEATURE:
<221> NAME/KEY: misc_feature
<222> LOCATION: (71)..(71)
<223> OTHER INFORMATION: N is T, A, G, or C at a ratio of 40:20:20:20
<220> FEATURE:
<221> NAME/KEY: misc_feature
<222> LOCATION: (73)..(73)
<223> OTHER INFORMATION: N can be A, T, C, or G
<220> FEATURE:
<221> NAME/KEY: misc_feature
<222> LOCATION: (74)..(74)
<223> OTHER INFORMATION: N is T, A, G, or C at a ratio of 40:20:20:20
<220> FEATURE:
<221> NAME/KEY: misc_feature
<222> LOCATION: (76)..(76)
<223> OTHER INFORMATION: N can be A, T, C, or G
<220> FEATURE:
<221> NAME/KEY: misc_feature
<222> LOCATION: (77)..(77)
<223> OTHER INFORMATION: N is T, A, G, or C at a ratio of 40:20:20:20
<220> FEATURE:
<221> NAME/KEY: misc_feature
<222> LOCATION: (79)..(79)
<223> OTHER INFORMATION: N can be A, T, C, or G
<220> FEATURE:
<221> NAME/KEY: misc_feature
<222> LOCATION: (80)..(80)
<223> OTHER INFORMATION: N is T, A, G, or C at a ratio of 40:20:20:20
<220> FEATURE:
<221> NAME/KEY: misc_feature
<222> LOCATION: (82)..(82)
<223> OTHER INFORMATION: N can be A, T, C, or G
<220> FEATURE:
<221> NAME/KEY: misc_feature
<222> LOCATION: (83)..(83)
<223> OTHER INFORMATION: N is T, A, G, or C at a ratio of 40:20:20:20
```

-continued

```
<220> FEATURE:
<221> NAME/KEY: misc_feature
<222> LOCATION: (85)..(85)
<223> OTHER INFORMATION: N can be A, T, C, or G
<220> FEATURE:
<221> NAME/KEY: misc_feature
<222> LOCATION: (86)..(86)
<223> OTHER INFORMATION: N is T, A, G, or C at a ratio of 40:20:20:20
<220> FEATURE:
<221> NAME/KEY: misc_feature
<222> LOCATION: (88)..(88)
<223> OTHER INFORMATION: N can be A, T, C, or G
<220> FEATURE:
<221> NAME/KEY: misc_feature
<222> LOCATION: (89)..(89)
<223> OTHER INFORMATION: N is T, A, G, or C at a ratio of 40:20:20:20
<220> FEATURE:
<221> NAME/KEY: misc_feature
<222> LOCATION: (91)..(91)
<223> OTHER INFORMATION: N can be A, T, C, or G
<220> FEATURE:
<221> NAME/KEY: misc_feature
<222> LOCATION: (92)..(92)
<223> OTHER INFORMATION: N is T, A, G, or C at a ratio of 40:20:20:20
<220> FEATURE:
<221> NAME/KEY: misc_feature
<222> LOCATION: (94)..(94)
<223> OTHER INFORMATION: N can be A, T, C, or G
<220> FEATURE:
<221> NAME/KEY: misc_feature
<222> LOCATION: (95)..(95)
<223> OTHER INFORMATION: N is T, A, G, or C at a ratio of 40:20:20:20
<220> FEATURE:
<221> NAME/KEY: misc_feature
<222> LOCATION: (97)..(97)
<223> OTHER INFORMATION: N can be A, T, C, or G
<220> FEATURE:
<221> NAME/KEY: misc_feature
<222> LOCATION: (98)..(98)
<223> OTHER INFORMATION: N is T, A, G, or C at a ratio of 40:20:20:20
<220> FEATURE:
<221> NAME/KEY: misc_feature
<222> LOCATION: (100)..(100)
<223> OTHER INFORMATION: N can be A, T, C, or G
<220> FEATURE:
<221> NAME/KEY: misc_feature
<222> LOCATION: (101)..(101)
<223> OTHER INFORMATION: N is T, A, G, or C at a ratio of 40:20:20:20
<220> FEATURE:
<221> NAME/KEY: misc_feature
<222> LOCATION: (103)..(103)
<223> OTHER INFORMATION: N can be A, T, C, or G
<220> FEATURE:
<221> NAME/KEY: misc_feature
<222> LOCATION: (104)..(104)
<223> OTHER INFORMATION: N is T, A, G, or C at a ratio of 40:20:20:20
<220> FEATURE:
<221> NAME/KEY: misc_feature
<222> LOCATION: (106)..(106)
<223> OTHER INFORMATION: N can be A, T, C, or G
<220> FEATURE:
<221> NAME/KEY: misc_feature
<222> LOCATION: (107)..(107)
<223> OTHER INFORMATION: N is T, A, G, or C at a ratio of 40:20:20:20
<220> FEATURE:
<221> NAME/KEY: misc_feature
<222> LOCATION: (109)..(109)
<223> OTHER INFORMATION: N can be A, T, C, or G
<220> FEATURE:
<221> NAME/KEY: misc_feature
<222> LOCATION: (110)..(110)
<223> OTHER INFORMATION: N is T, A, G, or C at a ratio of 40:20:20:20
<220> FEATURE:
<221> NAME/KEY: misc_feature
<222> LOCATION: (112)..(112)
<223> OTHER INFORMATION: N can be A, T, C, or G
<220> FEATURE:
<221> NAME/KEY: misc_feature
<222> LOCATION: (113)..(113)
```

```
<223> OTHER INFORMATION: N is T, A, G, or C at a ratio of 40:20:20:20
<220> FEATURE:
<221> NAME/KEY: misc_feature
<222> LOCATION: (115)..(115)
<223> OTHER INFORMATION: N can be A, T, C, or G
<220> FEATURE:
<221> NAME/KEY: misc_feature
<222> LOCATION: (116)..(116)
<223> OTHER INFORMATION: N is T, A, G, or C at a ratio of 40:20:20:20
<220> FEATURE:
<221> NAME/KEY: misc_feature
<222> LOCATION: (118)..(118)
<223> OTHER INFORMATION: N can be A, T, C, or G
<220> FEATURE:
<221> NAME/KEY: misc_feature
<222> LOCATION: (119)..(119)
<223> OTHER INFORMATION: N is T, A, G, or C at a ratio of 40:20:20:20
<220> FEATURE:
<221> NAME/KEY: misc_feature
<222> LOCATION: (121)..(121)
<223> OTHER INFORMATION: N can be A, T, C, or G
<220> FEATURE:
<221> NAME/KEY: misc_feature
<222> LOCATION: (122)..(122)
<223> OTHER INFORMATION: N is T, A, G, or C at a ratio of 40:20:20:20
<220> FEATURE:
<221> NAME/KEY: misc_feature
<222> LOCATION: (124)..(124)
<223> OTHER INFORMATION: N can be A, T, C, or G
<220> FEATURE:
<221> NAME/KEY: misc_feature
<222> LOCATION: (125)..(125)
<223> OTHER INFORMATION: N is T, A, G, or C at a ratio of 40:20:20:20
<220> FEATURE:
<221> NAME/KEY: misc_feature
<222> LOCATION: (127)..(127)
<223> OTHER INFORMATION: N can be A, T, C, or G
<220> FEATURE:
<221> NAME/KEY: misc_feature
<222> LOCATION: (128)..(128)
<223> OTHER INFORMATION: N is T, A, G, or C at a ratio of 40:20:20:20
<220> FEATURE:
<221> NAME/KEY: misc_feature
<222> LOCATION: (130)..(130)
<223> OTHER INFORMATION: N can be A, T, C, or G
<220> FEATURE:
<221> NAME/KEY: misc_feature
<222> LOCATION: (131)..(131)
<223> OTHER INFORMATION: N is T, A, G, or C at a ratio of 40:20:20:20
<220> FEATURE:
<221> NAME/KEY: misc_feature
<222> LOCATION: (133)..(133)
<223> OTHER INFORMATION: N can be A, T, C, or G
<220> FEATURE:
<221> NAME/KEY: misc_feature
<222> LOCATION: (134)..(134)
<223> OTHER INFORMATION: N is T, A, G, or C at a ratio of 40:20:20:20
<220> FEATURE:
<221> NAME/KEY: misc_feature
<222> LOCATION: (136)..(136)
<223> OTHER INFORMATION: N can be A, T, C, or G
<220> FEATURE:
<221> NAME/KEY: misc_feature
<222> LOCATION: (137)..(137)
<223> OTHER INFORMATION: N is T, A, G, or C at a ratio of 40:20:20:20
<220> FEATURE:
<221> NAME/KEY: misc_feature
<222> LOCATION: (139)..(139)
<223> OTHER INFORMATION: N can be A, T, C, or G
<220> FEATURE:
<221> NAME/KEY: misc_feature
<222> LOCATION: (140)..(140)
<223> OTHER INFORMATION: N is T, A, G, or C at a ratio of 40:20:20:20
<220> FEATURE:
<221> NAME/KEY: misc_feature
<222> LOCATION: (142)..(142)
<223> OTHER INFORMATION: N can be A, T, C, or G
<220> FEATURE:
<221> NAME/KEY: misc_feature
```

```
<222> LOCATION: (143)..(143)
<223> OTHER INFORMATION: N is T, A, G, or C at a ratio of 40:20:20:20
<220> FEATURE:
<221> NAME/KEY: misc_feature
<222> LOCATION: (145)..(145)
<223> OTHER INFORMATION: N can be A, T, C, or G
<220> FEATURE:
<221> NAME/KEY: misc_feature
<222> LOCATION: (146)..(146)
<223> OTHER INFORMATION: N is T, A, G, or C at a ratio of 40:20:20:20
<220> FEATURE:
<221> NAME/KEY: misc_feature
<222> LOCATION: (148)..(148)
<223> OTHER INFORMATION: N can be A, T, C, or G
<220> FEATURE:
<221> NAME/KEY: misc_feature
<222> LOCATION: (149)..(149)
<223> OTHER INFORMATION: N is T, A, G, or C at a ratio of 40:20:20:20

<400> SEQUENCE: 18
ctagctacct atagccggtg gtgatggtga tggtggccta agctaccgga gccsnnsnns      60
nnsnnsnnsn nsnnsnnsnn snnsnnsnns nnsnnsnnsn nsnnsnnsnn snnsnnsnns     120
nnsnnsnnsn nsnnsnnsnn snnsnnsnnc atttagctgt cctccttact aaagttaacc     180
ctatagtgag tcgtatta                                                    198

<210> SEQ ID NO 19
<211> LENGTH: 30
<212> TYPE: DNA
<213> ORGANISM: artificial
<220> FEATURE:
<223> OTHER INFORMATION: T7 Promoter Sequence

<400> SEQUENCE: 19
taatacgact cactataggg ttaactttag                                        30

<210> SEQ ID NO 20
<211> LENGTH: 38
<212> TYPE: DNA
<213> ORGANISM: artificial
<220> FEATURE:
<223> OTHER INFORMATION: Fixed Library Reverse Transcriptase Primer

<400> SEQUENCE: 20
tttttttttt tttttgtgat ggtggtgatg acccagag                               38

<210> SEQ ID NO 21
<211> LENGTH: 38
<212> TYPE: DNA
<213> ORGANISM: artificial
<220> FEATURE:
<223> OTHER INFORMATION: Variable library Reverse Transcriptase Primer

<400> SEQUENCE: 21
tttttttttt tttttgtgat ggtgatggtg gcctaagc                               38

<210> SEQ ID NO 22
<211> LENGTH: 38
<212> TYPE: DNA
<213> ORGANISM: artificial
<220> FEATURE:
<223> OTHER INFORMATION: Library FP1 Forward PCR Primer

<400> SEQUENCE: 22
taatacgact cactataggg ttaactttag taaggagg                               38

<210> SEQ ID NO 23
```

-continued

```
<211> LENGTH: 43
<212> TYPE: DNA
<213> ORGANISM: artificial
<220> FEATURE:
<223> OTHER INFORMATION: Fixed Library Reverse PCR Primer

<400> SEQUENCE: 23
ctagctacct atagccggtg gtgatggtgg tgatgaccca gag            43

<210> SEQ ID NO 24
<211> LENGTH: 43
<212> TYPE: DNA
<213> ORGANISM: artificial
<220> FEATURE:
<223> OTHER INFORMATION: Variable Library Reverse PCR Primer

<400> SEQUENCE: 24
ctagctacct atagccggtg gtgatggtga tggtggccta agc            43

<210> SEQ ID NO 25
<211> LENGTH: 62
<212> TYPE: DNA
<213> ORGANISM: artificial
<220> FEATURE:
<223> OTHER INFORMATION: Fixed Library Primer

<400> SEQUENCE: 25
ctagctacct atttgtcatc gtcgtcttta taatcccggt ggtgatggtg gtgatgaccc    60
ag                                                                   62

<210> SEQ ID NO 26
<211> LENGTH: 62
<212> TYPE: DNA
<213> ORGANISM: artificial
<220> FEATURE:
<223> OTHER INFORMATION: Variable Library Primer

<400> SEQUENCE: 26
ctagctacct atttgtcatc gtcgtcttta taatcccggt ggtgatggtg atggtggcct    60
aa                                                                   62

<210> SEQ ID NO 27
<211> LENGTH: 33
<212> TYPE: PRT
<213> ORGANISM: artificial
<220> FEATURE:
<223> OTHER INFORMATION: Clone 7F1
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 27

Xaa Tyr Tyr Leu Ser Val Tyr Pro Ser Tyr Ser Xaa Tyr Phe Ser Ser
1               5                   10                  15

Ser Tyr Val Val Trp Pro Xaa Pro Gly His Arg Leu Leu Ile Gly Leu
```

Glu

```
<210> SEQ ID NO 28
<211> LENGTH: 33
<212> TYPE: PRT
<213> ORGANISM: artificial
<220> FEATURE:
<223> OTHER INFORMATION: Clone 7F10
<220> FEATURE:
<221> NAME/KEY: MISC_FEATURE
<222> LOCATION: (1)..(2)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (8)..(8)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (22)..(23)
<223> OTHER INFORMATION: Xaa is a glycosylated derivative of
      homopropargylglycine or homopropargylglycine

<400> SEQUENCE: 28

Xaa Xaa Glu His Lys Leu Thr Xaa Leu Pro Leu Xaa Ser Thr Asp Ile
1               5                   10                  15

Phe Leu Val Leu Leu Xaa Xaa Phe Gly Thr Thr Ile Thr Gln Val Ser
            20                  25                  30
```

Leu

```
<210> SEQ ID NO 29
<211> LENGTH: 33
<212> TYPE: PRT
<213> ORGANISM: artificial
<220> FEATURE:
<223> OTHER INFORMATION: Clone 7F6
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (7)..(7)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (21)..(21)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (27)..(27)
<223> OTHER INFORMATION: Xaa is a glycosylated derivative of
      homopropargylglycine or homopropargylglycine
```

-continued

```
<220> FEATURE:
<221> NAME/KEY: MISC_FEATURE
<222> LOCATION: (32)..(32)
<223> OTHER INFORMATION: Xaa is a glycosylated derivative of
      homopropargylglycine or homopropargylglycine

<400> SEQUENCE: 29

Xaa Tyr Leu Pro Asp Trp Xaa Leu Lys Ser Leu Xaa Leu Ser Lys Trp
1               5                   10                  15

Arg Leu Pro Glu Xaa Phe Xaa Ser Pro Phe Xaa Leu Glu Leu His Xaa
            20                  25                  30

Ser

<210> SEQ ID NO 30
<211> LENGTH: 33
<212> TYPE: PRT
<213> ORGANISM: artificial
<220> FEATURE:
<223> OTHER INFORMATION: Clone 7F8
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (9)..(9)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (19)..(19)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(24)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (30)..(30)
<223> OTHER INFORMATION: Xaa is a glycosylated derivative of
      homopropargylglycine or homopropargylglycine

<400> SEQUENCE: 30

Xaa Leu Thr Asn Ile Thr Leu Gln Xaa Ser Arg Xaa His Leu Leu Trp
1               5                   10                  15

Leu His Xaa His Asp Leu Xaa Xaa Asp Leu Cys Arg Ile Xaa Leu Arg
            20                  25                  30

Ser

<210> SEQ ID NO 31
<211> LENGTH: 33
<212> TYPE: PRT
<213> ORGANISM: artificial
<220> FEATURE:
<223> OTHER INFORMATION: Clone 7F5
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (9)..(10)
```

<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (16)..(16)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (19)..(19)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (27)..(27)
<223> OTHER INFORMATION: Xaa is a glycosylated derivative of
      homopropargylglycine or homopropargylglycine

<400> SEQUENCE: 31

Xaa Val Leu Thr Pro Thr Thr Lys Xaa Xaa Val Xaa Gln Ser Pro Xaa
1               5                   10                  15

Tyr Phe Xaa Arg Ser Asn Xaa Leu Ser Lys Xaa Tyr Asp Tyr Gln Arg
            20                  25                  30

Leu

<210> SEQ ID NO 32
<211> LENGTH: 33
<212> TYPE: PRT
<213> ORGANISM: artificial
<220> FEATURE:
<223> OTHER INFORMATION: Clone 7F11
<220> FEATURE:
<221> NAME/KEY: MISC_FEATURE
<222> LOCATION: (1)..(2)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (4)..(4)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (7)..(7)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (29)..(29)
<223> OTHER INFORMATION: Xaa is a glycosylated derivative of
      homopropargylglycine or homopropargylglycine

<400> SEQUENCE: 32

Xaa Xaa Ile Xaa Asn Ser Xaa Arg Ile Asp Val Xaa Xaa Ser Asn Phe

```
                1               5                   10                  15
Val His Ala Lys Ser Thr Xaa Val Gly Gln Arg His Xaa Gly Gly Val
                20                  25                  30

Gly

<210> SEQ ID NO 33
<211> LENGTH: 33
<212> TYPE: PRT
<213> ORGANISM: artificial
<220> FEATURE:
<223> OTHER INFORMATION: Clone 7F12
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (3)..(3)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (15)..(15)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (19)..(19)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (28)..(28)
<223> OTHER INFORMATION: Xaa is a glycosylated derivative of
      homopropargylglycine or homopropargylglycine

<400> SEQUENCE: 33

Xaa Ser Xaa Thr Xaa Gln Phe Ser His Phe Trp Xaa Arg His Xaa Trp
1               5                   10                  15

Glu Ser Xaa Asn Arg Trp Xaa Leu Ala Arg Thr Xaa Asp Thr Pro Ile
                20                  25                  30

Asp

<210> SEQ ID NO 34
<211> LENGTH: 33
<212> TYPE: PRT
<213> ORGANISM: artificial
<220> FEATURE:
<223> OTHER INFORMATION: Clone 7F16
<220> FEATURE:
<221> NAME/KEY: MISC_FEATURE
<222> LOCATION: (1)..(2)
<223> OTHER INFORMATION: Xaa is a glycosylated derivative of
      homopropargylglycine or homopropargylglycine
<220> FEATURE:
<221> NAME/KEY: MISC_FEATURE
```

<222> LOCATION: (11)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (18)..(18)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (25)..(25)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (30)..(30)
<223> OTHER INFORMATION: Xaa is a glycosylated derivative of
      homopropargylglycine or homopropargylglycine

<400> SEQUENCE: 34

Xaa Xaa Cys His Cys Leu Pro Ser His Tyr Xaa Xaa Leu Arg Phe Cys
1               5                   10                  15

Pro Xaa Thr Gly Ser Val Xaa Asp Xaa Gly Leu Lys Arg Xaa Val Tyr
            20                  25                  30

His

<210> SEQ ID NO 35
<211> LENGTH: 31
<212> TYPE: PRT
<213> ORGANISM: artificial
<220> FEATURE:
<223> OTHER INFORMATION: Clone 7F2
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (7)..(8)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (10)..(10)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (16)..(16)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (21)..(22)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (24)..(24)
<223> OTHER INFORMATION: Xaa is a glycosylated derivative of
      homopropargylglycine or homopropargylglycine

<400> SEQUENCE: 35

```
Xaa Ala Lys Phe Asp Glu Xaa Xaa Ala Xaa Leu Asn Xaa Ser Arg Xaa
1               5                  10                  15

Ser Ser Tyr Leu Xaa Xaa Leu Xaa Thr Gly Arg Thr Trp Pro His
            20                  25                  30

<210> SEQ ID NO 36
<211> LENGTH: 33
<212> TYPE: PRT
<213> ORGANISM: artificial
<220> FEATURE:
<223> OTHER INFORMATION: Clone 7F15
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (14)..(14)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (17)..(17)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (19)..(20)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (25)..(25)
<223> OTHER INFORMATION: Xaa is a glycosylated derivative of
      homopropargylglycine or homopropargylglycine

<400> SEQUENCE: 36

Xaa Thr Phe Glu Xaa Leu Pro Arg Ser Asp Ser Xaa Arg Xaa Leu Thr
1               5                  10                  15

Xaa Pro Xaa Xaa His Arg Xaa Tyr Xaa Ile Tyr Arg Gly Tyr Ser Asn
            20                  25                  30

Arg

<210> SEQ ID NO 37
<211> LENGTH: 33
<212> TYPE: PRT
<213> ORGANISM: artificial
<220> FEATURE:
<223> OTHER INFORMATION: Clone 7F17
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
```

```
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(13)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (18)..(18)
<223> OTHER INFORMATION: Xaa is a glycosylated derivative of
      homopropargylglycine or homopropargylglycine
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (33)..(33)
<223> OTHER INFORMATION: Xaa is a glycosylated derivative of
      homopropargylglycine or homopropargylglycine

<400> SEQUENCE: 37

Xaa Ser Tyr Ser Xaa Ser Pro Arg Asp Pro Asn Xaa Xaa Ile Lys Phe
1               5                   10                  15

Leu Xaa Ser Arg Thr Xaa Xaa Arg Asn Pro Xaa Asn Val Ile Gly Ser
            20                  25                  30

Xaa

<210> SEQ ID NO 38
<211> LENGTH: 33
<212> TYPE: PRT
<213> ORGANISM: artificial
<220> FEATURE:
<223> OTHER INFORMATION: Clone 7V12
<220> FEATURE:
<221> NAME/KEY: MISC_FEATURE
<222> LOCATION: (1)..(1)
<223> OTHER INFORMATION: Xaa is a glycosylated homopropargylglycine
<220> FEATURE:
<221> NAME/KEY: MISC_FEATURE
<222> LOCATION: (8)..(8)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (18)..(19)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (28)..(29)
<223> OTHER INFORMATION: Xaa is a glycosylated derivative of
      homopropargylglycine or homopropargylglycine

<400> SEQUENCE: 38

Xaa His Ile Ser Thr Asn Cys Xaa Pro Trp Arg Tyr Trp Ser Ile Ile
1               5                   10                  15

Cys Xaa Xaa Pro Thr Trp Lys Thr Val His Gln Xaa Xaa Lys Thr Lys
            20                  25                  30

Asp

<210> SEQ ID NO 39
<211> LENGTH: 33
<212> TYPE: PRT
<213> ORGANISM: artificial
```

-continued

```
<220> FEATURE:
<223> OTHER INFORMATION: Clone 7V6
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (6)..(6)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (15)..(15)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (17)..(17)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (20)..(21)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (25)..(25)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (27)..(27)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (33)..(33)
<223> OTHER INFORMATION: Xaa is a glycosylated derivative of
      homopropargylglycine or homopropargylglycine

<400> SEQUENCE: 39

Xaa Cys Ser Arg Lys Xaa Ala Cys Leu Ser Arg Ala Asn Leu Xaa Arg
1               5                   10                  15

Xaa Arg Ser Xaa Xaa Lys Arg Arg Xaa Thr Xaa Asn Thr Ser Phe Thr
            20                  25                  30

Xaa

<210> SEQ ID NO 40
<211> LENGTH: 33
<212> TYPE: PRT
<213> ORGANISM: artificial
<220> FEATURE:
<223> OTHER INFORMATION: Clone 7V8
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (4)..(4)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (15)..(15)
<223> OTHER INFORMATION: Xaa is a glycosylated derivative of
```

```
       homopropargylglycine or homopropargylglycine
<220> FEATURE:
<221> NAME/KEY: MISC_FEATURE
<222> LOCATION: (18)..(18)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (22)..(22)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (25)..(25)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (32)..(32)
<223> OTHER INFORMATION: Xaa is a glycosylated derivative of
       homopropargylglycine or homopropargylglycine

<400> SEQUENCE: 40

Xaa Ile Arg Xaa Arg Thr Pro Thr Ser Arg Leu Xaa Ser Thr Xaa Arg
1               5                   10                  15

Gly Xaa Thr Xaa Asn Xaa Thr Ser Xaa Ile Thr Pro Arg Asn Asp Xaa
            20                  25                  30

Ile

<210> SEQ ID NO 41
<211> LENGTH: 33
<212> TYPE: PRT
<213> ORGANISM: artificial
<220> FEATURE:
<223> OTHER INFORMATION: Clone 7V10
<220> FEATURE:
<221> NAME/KEY: MISC_FEATURE
<222> LOCATION: (1)..(1)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (6)..(6)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (9)..(9)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (15)..(16)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
       homopropargylglycine or homopropargylglycine
<220> FEATURE:
<221> NAME/KEY: MISC_FEATURE
<222> LOCATION: (30)..(31)
<223> OTHER INFORMATION: Xaa is a glycosylated derivative of
       homopropargylglycine or homopropargylglycine
```

```
<400> SEQUENCE: 41

Xaa Thr Pro Phe Thr Xaa Ala Tyr Xaa Thr Arg Arg Lys Pro Xaa Xaa
1               5                   10                  15

Phe Pro Ile Xaa His Arg Xaa Lys Ser Arg Thr Pro Leu Xaa Xaa Gly
            20                  25                  30

Lys

<210> SEQ ID NO 42
<211> LENGTH: 33
<212> TYPE: PRT
<213> ORGANISM: artificial
<220> FEATURE:
<223> OTHER INFORMATION: Clone 7V3
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (3)..(3)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (11)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (17)..(17)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (22)..(22)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (26)..(26)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (29)..(29)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (32)..(33)
<223> OTHER INFORMATION: Xaa is a glycosylated derivative of
      homopropargylglycine or homopropargylglycine

<400> SEQUENCE: 42

Xaa Lys Xaa Asn Xaa Arg Ile Trp Asn Pro Xaa Xaa Asn Asn Trp Ser
1               5                   10                  15

Xaa Asp Thr Ala Ser Xaa Leu Arg Leu Xaa Ser Trp Xaa Leu Asn Xaa
            20                  25                  30

Xaa

<210> SEQ ID NO 43
<211> LENGTH: 33
<212> TYPE: PRT
<213> ORGANISM: artificial
```

```
<220> FEATURE:
<223> OTHER INFORMATION: Clone 7V4
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (9)..(10)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (15)..(15)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (18)..(18)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (25)..(28)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (30)..(30)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (33)..(33)
<223> OTHER INFORMATION: Xaa is a glycosylated derivative of
      homopropargylglycine or homopropargylglycine

<400> SEQUENCE: 43

Xaa Thr Ser Ile Xaa Asp Asn Thr Xaa Xaa Leu Ser Val Asn Xaa Asn
1               5                   10                  15

Arg Xaa Lys Ile Asn Arg Thr Leu Xaa Xaa Xaa Xaa His Xaa Ser Thr
            20                  25                  30

Xaa

<210> SEQ ID NO 44
<211> LENGTH: 33
<212> TYPE: PRT
<213> ORGANISM: artificial
<220> FEATURE:
<223> OTHER INFORMATION: Clone 7V9
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (3)..(3)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (5)..(5)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (10)..(10)
<223> OTHER INFORMATION: Xaa is a glycosylated derivative of
```

```
      homopropargylglycine or homopropargylglycine
<220> FEATURE:
<221> NAME/KEY: MISC_FEATURE
<222> LOCATION: (14)..(14)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (16)..(16)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (18)..(18)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (21)..(21)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (26)..(26)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (29)..(29)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (31)..(31)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (33)..(33)
<223> OTHER INFORMATION: Xaa is a glycosylated derivative of
      homopropargylglycine or homopropargylglycine

<400> SEQUENCE: 44

Xaa Cys Xaa Lys Xaa Tyr Ala Pro Asn Xaa Tyr Asp Leu Xaa Pro Xaa
1               5                   10                  15

Arg Xaa His Trp Xaa Pro Asn Val Leu Xaa Pro Leu Xaa Ser Xaa Arg
            20                  25                  30

Xaa

<210> SEQ ID NO 45
<211> LENGTH: 33
<212> TYPE: PRT
<213> ORGANISM: artificial
<220> FEATURE:
<223> OTHER INFORMATION: Clone 6E
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 45

Xaa Gln Thr Ala Cys Pro Ser Pro Ala Phe Leu Xaa Leu Ser Arg Ser
1               5                   10                  15
```

Ala His Tyr Phe His Ala Xaa His Pro Thr Ser Ala Ala Pro Asp Ile
        20                  25                  30

Ser

<210> SEQ ID NO 46
<211> LENGTH: 33
<212> TYPE: PRT
<213> ORGANISM: artificial
<220> FEATURE:
<223> OTHER INFORMATION: Clone 12G
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (10)..(10)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (17)..(17)
<223> OTHER INFORMATION: Xaa is a glycosylated derivative of
      homopropargylglycine or homopropargylglycine

<400> SEQUENCE: 46

Xaa Tyr Lys Asn Ile Pro Ser Thr Thr Xaa Asn Leu Tyr Ser Lys Pro
1               5                   10                  15

Xaa Ala Thr Val Thr Thr Leu Lys Cys Lys Leu Asn Gly Asn Arg Ile
        20                  25                  30

Ser

<210> SEQ ID NO 47
<211> LENGTH: 33
<212> TYPE: PRT
<213> ORGANISM: artificial
<220> FEATURE:
<223> OTHER INFORMATION: Clone 10F16
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 47

Xaa Val Arg Ser Ala Ala Val Asp Thr Ser Pro Xaa Thr Ser Ser Ser
1               5                   10                  15

Gln Asn Ala Ile Leu Leu Xaa Phe Ser Tyr Asp Val Cys Leu Phe Asp
        20                  25                  30

Leu

<210> SEQ ID NO 48
<211> LENGTH: 33
<212> TYPE: PRT
<213> ORGANISM: artificial
<220> FEATURE:
<223> OTHER INFORMATION: Clone 10F20

```
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine

<400> SEQUENCE: 48

Xaa Ile Ala Leu Thr Ser Asn Cys Tyr Leu Asn Xaa Gly Pro Arg Ile
1               5                   10                  15

Phe Arg Tyr Asp Val Gly Leu Thr Gln Leu Cys Gln Gly Arg Arg Arg
            20                  25                  30

Ser

<210> SEQ ID NO 49
<211> LENGTH: 33
<212> TYPE: PRT
<213> ORGANISM: artificial
<220> FEATURE:
<223> OTHER INFORMATION: Clone 10F23
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 49

Xaa Asp Thr Leu His Leu Lys Gln Ile Gly Val Xaa Pro Asn Cys Ile
1               5                   10                  15

Thr Gln Gln Asp Val Arg Xaa Thr Ser Ile Pro Tyr Thr Tyr Thr Trp
            20                  25                  30

Pro

<210> SEQ ID NO 50
<211> LENGTH: 33
<212> TYPE: PRT
<213> ORGANISM: artificial
<220> FEATURE:
<223> OTHER INFORMATION: Clone 10F18
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (16)..(16)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
```

<223> OTHER INFORMATION: Xaa is a glycosylated derivative of
    homopropargylglycine or homopropargylglycine

<400> SEQUENCE: 50

Xaa Phe Ser Thr Ala Asn Ile Tyr Gly Ala Pro Xaa Asn Thr Asp Xaa
1               5                   10                  15

Arg Leu Glu His Arg Gln Xaa Lys Ser Ile Pro Tyr Thr Tyr Tyr Trp
            20                  25                  30

Ser

<210> SEQ ID NO 51
<211> LENGTH: 33
<212> TYPE: PRT
<213> ORGANISM: artificial
<220> FEATURE:
<223> OTHER INFORMATION: Clone 10V14
<220> FEATURE:
<221> NAME/KEY: MISC_FEATURE
<222> LOCATION: (1)..(1)
<223> OTHER INFORMATION: Xaa is a glycosylated derivative of
    homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
    homopropargylglycine or homopropargylglycine

<400> SEQUENCE: 51

Xaa Ala Thr Lys Thr Asn Cys Lys Arg Glu Lys Thr Ile Asp Asn His
1               5                   10                  15

Val Thr Ile Xaa Arg Ser Ile Pro Trp Tyr Thr Tyr Arg Trp Leu Pro
            20                  25                  30

Asn

<210> SEQ ID NO 52
<211> LENGTH: 33
<212> TYPE: PRT
<213> ORGANISM: Artificial
<220> FEATURE:
<223> OTHER INFORMATION: Clone 10F5-C10,25S
<220> FEATURE:
<221> NAME/KEY: MISC_FEATURE
<222> LOCATION: (1)..(1)
<223> OTHER INFORMATION: Xaa is a glycosylated derivative of
    homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
    homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
    homopropargylglycine or homopropargylglycine
<220> FEATURE:
<221> NAME/KEY: MISC_FEATURE
<222> LOCATION: (29)..(29)
<223> OTHER INFORMATION: Xaa is a glycosylated derivative of
    homopropargylglycine or homopropargylglycine

<400> SEQUENCE: 52

Xaa Ser Pro His Leu Pro Val Leu Leu Ser Lys Xaa Val Leu Asn Asp
1               5                   10                  15

Gly Arg Arg Ile Val Gln Xaa Ser Ser Glu Leu Pro Xaa Val Arg Arg
            20                  25                  30

Ser

<210> SEQ ID NO 53
<211> LENGTH: 33
<212> TYPE: PRT
<213> ORGANISM: Artificial
<220> FEATURE:
<223> OTHER INFORMATION: Clone 10V1-C7S
<220> FEATURE:
<221> NAME/KEY: MISC_FEATURE
<222> LOCATION: (1)..(1)
<223> OTHER INFORMATION: Xaa is a glycosylated derivative of
     homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
     homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
     homopropargylglycine or homopropargylglycine

<400> SEQUENCE: 53

Xaa Ala Thr Lys Thr Asn Ser Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn

<210> SEQ ID NO 54
<211> LENGTH: 33
<212> TYPE: PRT
<213> ORGANISM: Artificial
<220> FEATURE:
<223> OTHER INFORMATION: Clone 10V1-C7A
<220> FEATURE:
<221> NAME/KEY: MISC_FEATURE
<222> LOCATION: (1)..(1)
<223> OTHER INFORMATION: Xaa is a glycosylated derivative of
     homopropargylglycine or homopropargylglycine
<220> FEATURE:
<221> NAME/KEY: MISC_FEATURE
<222> LOCATION: (13)..(13)
<223> OTHER INFORMATION: Xaa is a glycosylated derivative of
     homopropargylglycine or homopropargylglycine
<220> FEATURE:
<221> NAME/KEY: MISC_FEATURE
<222> LOCATION: (20)..(20)
<223> OTHER INFORMATION: Xaa is a glycosylated derivative of
     homopropargylglycine or homopropargylglycine

<400> SEQUENCE: 54

Xaa Ala Thr Lys Thr Asn Ala Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn

<210> SEQ ID NO 55
<211> LENGTH: 14
<212> TYPE: PRT
<213> ORGANISM: Artificial
<220> FEATURE:
<223> OTHER INFORMATION: Clone 10V1-Delta 19
<220> FEATURE:
<221> NAME/KEY: MISC_FEATURE
<222> LOCATION: (1)..(1)
<223> OTHER INFORMATION: Xaa is a glycosylated derivative of
     homopropargylglycine or homopropargylglycine

```
<400> SEQUENCE: 55

Xaa Arg Ser Ile Pro Trp Tyr Thr Tyr Arg Trp Leu Pro Asn
1               5                   10

<210> SEQ ID NO 56
<211> LENGTH: 22
<212> TYPE: PRT
<213> ORGANISM: Artificial
<220> FEATURE:
<223> OTHER INFORMATION: Clone 10F2-Delta 11
<220> FEATURE:
<221> NAME/KEY: MISC_FEATURE
<222> LOCATION: (1)..(2)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (7)..(7)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine

<400> SEQUENCE: 56

Xaa Xaa Ala Ala Leu Lys Xaa Gln Val Thr Asp Xaa Tyr Ala Leu Ala
1               5                   10                  15

Leu Phe His Arg Ile Leu
            20

<210> SEQ ID NO 57
<211> LENGTH: 22
<212> TYPE: PRT
<213> ORGANISM: Artificial
<220> FEATURE:
<223> OTHER INFORMATION: Clone 10F3-Delta 11
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine

<400> SEQUENCE: 57

Xaa Pro Asn Cys Ile Thr Gln Gln Asp Val Arg Xaa Thr Ser Ile Pro
1               5                   10                  15

Tyr Thr Tyr Thr Trp Pro
            20

<210> SEQ ID NO 58
<211> LENGTH: 22
<212> TYPE: PRT
<213> ORGANISM: Artificial
<220> FEATURE:
<223> OTHER INFORMATION: Clone 10F5-Delta 11
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
```

<220> FEATURE:
<221> NAME/KEY: MISC_FEATURE
<222> LOCATION: (18)..(18)
<223> OTHER INFORMATION: Xaa is a glycosylated derivative of
      homopropargylglycine or homopropargylglycine

<400> SEQUENCE: 58

Xaa Val Leu Asn Asp Gly Arg Arg Ile Val Gln Xaa Ser Cys Glu Leu
1               5                   10                  15

Pro Xaa Val Arg Arg Ser
            20

<210> SEQ ID NO 59
<211> LENGTH: 33
<212> TYPE: PRT
<213> ORGANISM: Artificial
<220> FEATURE:
<223> OTHER INFORMATION: Clone 10F12-C2, 21S
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (10)..(10)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 59

Xaa Ser Tyr Val Thr Val Ile Pro Ala Xaa Asn Xaa Pro Glu Ala Arg
1               5                   10                  15

Leu Gly Ile Val Ser His Xaa Pro Gly Ile Arg Arg Gly Lys Ala Leu
            20                  25                  30

Tyr

<210> SEQ ID NO 60
<211> LENGTH: 40
<212> TYPE: PRT
<213> ORGANISM: Artificial
<220> FEATURE:
<223> OTHER INFORMATION: Clone 10F2, unglycosylated
<220> FEATURE:
<221> NAME/KEY: MISC_FEATURE
<222> LOCATION: (1)..(1)
<223> OTHER INFORMATION: Xaa is homopropargylglycine
<220> FEATURE:
<221> NAME/KEY: MISC_FEATURE
<222> LOCATION: (12)..(13)
<223> OTHER INFORMATION: Xaa is homopropargylglycine
<220> FEATURE:
<221> NAME/KEY: MISC_FEATURE
<222> LOCATION: (18)..(18)
<223> OTHER INFORMATION: Xaa is homopropargylglycine
<220> FEATURE:
<221> NAME/KEY: MISC_FEATURE
<222> LOCATION: (23)..(23)
<223> OTHER INFORMATION: Xaa is homopropargylglycine
<220> FEATURE:
<221> NAME/KEY: MISC_FEATURE
<222> LOCATION: (39)..(39)
<223> OTHER INFORMATION: Xaa is St-butyl protected cysteine

```
<400> SEQUENCE: 60

Xaa His Pro Tyr Asn Thr Ser Arg Thr Ser Ala Xaa Xaa Ala Ala Leu
1               5                   10                  15

Lys Xaa Gln Val Thr Asp Xaa Tyr Ala Leu Ala Leu Phe His Arg Ile
            20                  25                  30

Leu Gly Ser Gly Ser Gly Xaa Ala
        35                  40

<210> SEQ ID NO 61
<211> LENGTH: 33
<212> TYPE: PRT
<213> ORGANISM: Artificial
<220> FEATURE:
<223> OTHER INFORMATION: Clone 8E
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (8)..(8)
<223> OTHER INFORMATION: Xaa is a glycosylated derivative of
      homopropargylglycine or homopropargylglycine

<400> SEQUENCE: 61

Xaa Arg Glu Trp Gln Arg Lys Xaa Thr Gln Lys Glu Tyr Thr Arg Lys
1               5                   10                  15

Thr Cys Lys Pro Thr Arg Cys Trp Leu Asp Lys Ser Asp Arg Thr Ser
            20                  25                  30

Lys

<210> SEQ ID NO 62
<211> LENGTH: 33
<212> TYPE: PRT
<213> ORGANISM: Artificial
<220> FEATURE:
<223> OTHER INFORMATION: Clone 10F3-C15S
<220> FEATURE:
<221> NAME/KEY: MISC_FEATURE
<222> LOCATION: (1)..(1)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (12)..(12)
<223> OTHER INFORMATION: Xaa is a glycosylated derivative of
      homopropargylglycine or homopropargylglycine
<220> FEATURE:
<221> NAME/KEY: MISC_FEATURE
<222> LOCATION: (23)..(23)
<223> OTHER INFORMATION: Xaa is a glycosylated derivative of
      homopropargylglycine or homopropargylglycine

<400> SEQUENCE: 62

Xaa Asp Thr Leu His Leu Lys Gln Ile Gly Gly Xaa Pro Asn Ser Ile
1               5                   10                  15

Thr Gln Gln Asp Val Arg Xaa Thr Ser Ile Pro Tyr Thr Tyr Thr Trp
            20                  25                  30

Pro
```